(12) United States Patent
Li et al.

(10) Patent No.: US 10,822,334 B2
(45) Date of Patent: Nov. 3, 2020

(54) ERBB RECEPTOR INHIBITORS

(71) Applicant: Dizal (Jiangsu) Pharmaceutical Co., Ltd., Shanghai (CN)

(72) Inventors: Zhengtao Li, Shanghai (CN); Wei Zhong, Corona, CA (US); Jiabing Wang, Chalfont, PA (US); Qingbei Zeng, Shanghai (CN); Honchung Tsui, Shanghai (CN); Zhenfan Yang, Shanghai (CN); Xiaolin Zhang, Shanghai (CN)

(*) Notice: Subject to any disclaimer, the term of this patent is extended or adjusted under 35 U.S.C. 154(b) by 0 days.

(21) Appl. No.: 16/910,267

(22) Filed: Jun. 24, 2020

(65) Prior Publication Data

US 2020/0317669 A1 Oct. 8, 2020

Related U.S. Application Data

(63) Continuation of application No. PCT/CN2019/085949, filed on May 8, 2019.

(30) Foreign Application Priority Data

May 8, 2018 (WO) ................ PCT/CN2018/085998

(51) Int. Cl.
C07D 471/04 (2006.01)
C07K 16/32 (2006.01)
A61K 45/06 (2006.01)

(52) U.S. Cl.
CPC ............ *C07D 471/04* (2013.01); *C07K 16/32* (2013.01); *A61K 45/06* (2013.01); *C07B 2200/13* (2013.01)

(58) Field of Classification Search
CPC .......................... C07D 471/04; A61K 31/517
USPC ........................................ 544/293; 514/266.1
See application file for complete search history.

(56) References Cited

FOREIGN PATENT DOCUMENTS

| WO | 03040109 A2 | 5/2003 |
|---|---|---|
| WO | 2006092573 A1 | 9/2006 |
| WO | 2007034144 A1 | 3/2007 |

OTHER PUBLICATIONS

Bernard Barlaam et al., "Neutral 5-substituted 4-indazolylaminoquinazolines as potent, orally active inhibitors of erbB2 receptor tyrosine kinase", Bioorganic & Medicinal Chemistry Letters, No. 18, Feb. 16, 2008 (Feb. 16, 2008),1799-1803.
International Search Report of PCT Application No. PCT/CN2019/085949, dated Aug. 22, 2019.
Written Opinion of the International Searching Authority of PCT Application No. PCT/CN2019/085949, dated Aug. 22, 2019.

*Primary Examiner* — Jeffrey H Murray
(74) *Attorney, Agent, or Firm* — Jun He Law Offices P.C.; Zhaohui Wang

(57) ABSTRACT

Disclosed are compounds inhibiting ErbBs (e.g. HER2), pharmaceutically acceptable salts, hydrates, solvates or stereoisomers thereof and pharmaceutical compositions comprising the compounds. The compound and the pharmaceutical composition can effectively treat diseases associated ErbBs (especially HER2), including cancer.

6 Claims, No Drawings

ERBB RECEPTOR INHIBITORS

CROSS-REFERENCE TO RELATED APPLICATIONS

This application is a Continuation of PCT Patent Application No. PCT/CN2019/085949, filed on May 8, 2019, which claims foreign priority of PCT Patent Application No. PCT/2018/085998, filed on May 8, 2018, now abandoned. Each of these applications is hereby incorporated by reference herein in its entirety.

FIELD OF THE DISCLOSURE

The present disclosure relates to compounds that inhibit ErbBs (e.g. HER2). The present disclosure also relates to a pharmaceutical composition comprising one or more of the compounds as an active ingredient, and use of the compounds in the manufacture of medicaments for treating diseases associated with ErbBs (e.g. HER2).

BACKGROUND

The ErbB receptor tyrosine kinase family consists of four closely related receptors: EGFR (ErbB1 or HER1), ErbB2 (HER2), ErbB3 (HER3), and ErbB4 (HER4) (Reviewed in Riese and Stern, Bioessays (1998) 20:41-48; Olayioye et al, EMBO Journal (2000) 19:3159-3167; and Schlessinger, Cell (2002) 110:669-672). These receptors act to transmit signals from the outside of a cell to the inside by activating secondary messenging effectors via a phosphorylation event at their tyrosine phosphorylation residues. A variety of cellular processes are modulated by these signals, including proliferation, carbohydrate utilization, protein synthesis, angiogenesis, cell growth, and cell survival. Deregulation of ErbB family signalling modulates proliferation, invasion, metastasis, angiogenesis, and tumour cell survival and may be associated with many human cancers, including those of the lung, head and neck and breast cancers. Detailed reviews of ErbB receptor signalling and its involvement in tumourigenesis are provided in New England Journal of Medicine, 2008, Vol. 358:1160-74 and Biochemical and Biophysical Research Communications, 2004, Vol. 319: 1-11.

Several investigators have demonstrated the role of EGFR and ErbB2 in development of cancer (reviewed in Salomon, et al., Crit. Rev. Oncol. Hematol. (1995) 19:183-232; Klapper, et al, Adv. Cancer Res. (2000) 77:25-79; and Hynes and Stern, Biochim. Biophys. Acta (1994) 1198:165-184). Squamous carcinomas of the head, neck and lung express high levels of EGFR. Also, constitutively active EGFR has been found in gliomas, breast cancer and lung cancer. ErbB2 overexpression occurs in approximately 30% of all breast cancer, and has been implicated in various other cancer types such as ovarian, colon, bladder, stomach, esophagus, lung, uterus and prostate cancers. ErbB2 overexpression has also been correlated with poor prognosis in human cancer, including metastasis and early relapse.

Several inhibitors of the EGFR and the ErbB2 signaling pathway have demonstrated clinical efficacy in cancer treatment. Gefitinib (IRESSA), erlotinib (TARCEVA), lapatinib (TYKERB, TYVERB), panitumumab (VECTIBIX), cetuximab (ERBITUX), osimertinib (TAGRISSO, AZD9291) and afatinib (GIOTRIF) are clinincally available EGFR inhibitors. Clinically available anticancer drugs targeting HER2 include Trastuzumab (also known as Herceptin), Trastuzumab emantasine (T-DM1), Pertuzumab (Perjeta), Lapatinib (Tyverb), and Neratinib (Nerlynx). Although two thirds of breast cancer patients respond well to herceptin trastuzumab, some HER2-positive breast cancer patients do not respond to the drug.

Accordingly, there remains a need to develop novel ErbB (especially HER2) inhibitors.

SUMMARY

In one aspect, the present disclosure provides a compound represented by Formula (I):

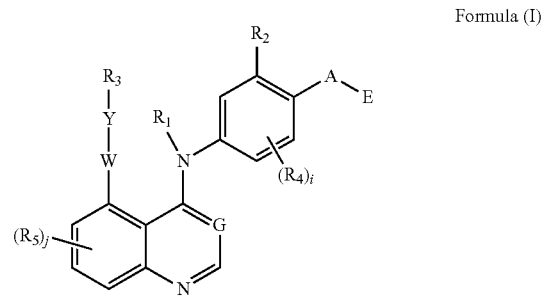

Formula (I)

or a pharmaceutically acceptable salt, ester, hydrate, solvate or stereoisomer thereof.

In another aspect, the present disclosure provides a pharmaceutical composition comprising one or more compounds of Formula (I), pharmaceutically acceptable salts, ester, hydrates, solvates or stereoisomers thereof and a pharmaceutically acceptable diluent, excipient or carrier.

In yet another aspect, the present disclosure provides a compound of Formula (I), or a pharmaceutically acceptable salt, ester, hydrate, solvate or stereoisomer thereof, or a pharmaceutical composition of one or more of the foregoing for use as a medicament for inhibiting ErbB (e.g. HER2).

In another aspect, the present disclosure provides a method of inhibiting ErbB (e.g. HER2) by using one or more compounds of Formula (I), pharmaceutically acceptable salts, ester, hydrates, solvates or stereoisomers thereof, or a pharmaceutical composition of one or more of the foregoing.

In another aspect, the present disclosure provides a method of treating diseases associated with HER2 in a subject, comprising administering to the subject an effective amount of one or more compounds of Formula (I), pharmaceutically acceptable salts, esters, hydrates, solvates or stereoisomers thereof, or a pharmaceutical composition of one or more of the foregoing.

In a further aspect, the present disclosure provides a compound of Formula (I) or a pharmaceutically acceptable salt, ester, hydrate, solvate or stereoisomer thereof, in combination with a second therapeutic agent, preferably an anti-tumor agent, such as a chemotherapeutics (capecitabine, docetaxel, vinorelbine), or a HER2 targeted antibody (trasutzumab (Herceptin), trastuzumab emantasine (T-DM1), pertuzumab (Perjeta)).

In another aspect, the present disclosure provides use of a compound of Formula (I) or a pharmaceutically acceptable salt, ester, hydrate, solvate or stereoisomer thereof, in the manufacture of a medicament for treating diseases associated with ErbB (e.g. HER2) in a subj ect.

DETAILED DESCRIPTION

Compounds

In one aspect, the present disclosure provides compounds of Formula (I):

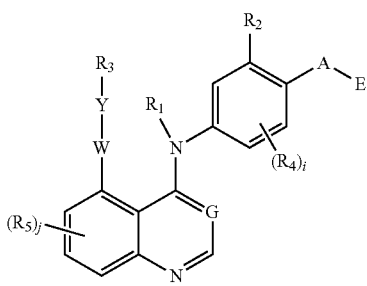

Formula (I)

or a pharmaceutically acceptable salt, ester, hydrate, solvate or stereoisomer thereof,
wherein, $R_1$ is hydrogen;

$R_2$ is hydrogen, halogen, hydroxyl, $C_{1-12}$ alkyl, $C_{1-12}$ alkoxyl, $C_{1-12}$ alky-OH, or $C_{1-12}$ haloalkyl;

G is N or C—CN;

W is O, C(=O), S, SO, or $SO_2$;

Y is bond or $C_{1-12}$ alkylene, $R_3$ is 3-10 membered saturated or unsaturated carbocyclyl, or 3-10 membered saturated or unsaturated heterocyclyl which can be optionally mono- or independently multi-substituted by halogen, hydroxyl, amino, $C_{1-12}$ alkyl, $C_{1-12}$ alkoxyl, $C_{1-12}$ alky-OH, $C_{1-12}$ haloalkyl, substituted $C_{1-12}$ alkyl;

i is 0, 1, 2 or 3, and each $R_4$ is independently halogen, amino, hydroxyl, $C_{1-12}$ alkyl, $C_{1-12}$ alkoxyl, $C_{1-12}$ alky-OH, or $C_{1-12}$ haloalkyl;

j is 0, 1, 2 or 3, and each $R_5$ is independently halogen, amino, hydroxyl, $C_{1-12}$ alkyl, $C_{1-12}$ alkoxyl, $C_{1-12}$ alky-OH, $C_{1-12}$ haloalkyl or $OR_6$, wherein $R_6$ is 3-10 membered saturated or unsaturated carbocyclyl, or 3-10 membered saturated or unsaturated heterocyclyl optionally mono- or independently multi-substituted by hydroxyl, halogen, cyano, $C_{1-12}$ alkyl, or $C_{1-12}$ haloalkyl;

A is O, C(=O), S, SO, or $SO_2$;

E is

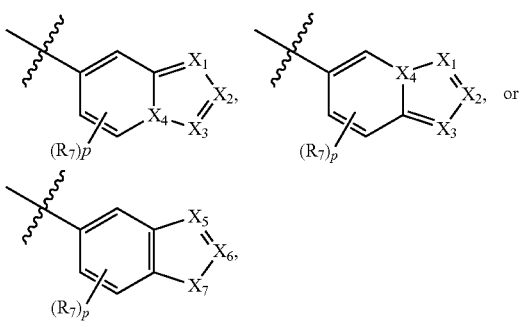

$X_1$, $X_2$, $X_3$, and $X_4$ are each independently N or $CR_8$;

$X_5$ and $X_6$ are each independently N or $CR_8$, and $X_7$ is O, S, $NR_9$ or $CR_{10}R_{11}$, wherein at least one of $X_5$ and $X_6$ is N; $R_8$, $R_9$, $R_{10}$, and $R_{11}$ are each independently hydrogen, halogen, $C_{1-12}$ alkyl, cyano, amino, hydroxyl, $C_{1-12}$ alkoxyl, $C_{1-12}$ alky-OH, or $C_{1-12}$ haloalkyl;

p is 0, 1, 2 or 3, and each $R_7$ is independently halogen, amino, hydroxyl, $C_{1-12}$ alkyl, $C_{1-12}$ alkoxyl, $C_{1-12}$ alky-OH, or $C_{1-12}$ haloalkyl.

In some embodiments, $R_2$ in Formula (I) is halogen, hydroxyl, $C_{1-12}$ alkyl, or $C_{1-12}$ alkoxyl.

In some embodiments, i=0. In some embodiments, i=1, and $R_4$ in Formula (I) is halogen.

In some embodiments, j=1 or 2, each $R_5$ is independently amino, $C_{1-12}$ alkoxyl, or $OR_6$; wherein $R_6$ is 3-10 membered saturated or unsaturated carbocyclyl, or 3-10 membered saturated or unsaturated heterocyclyl optionally mono- or independently multi-substituted by hydroxyl, halogen, cyano, $C_{1-12}$ alkyl, or $C_{1-12}$ haloalkyl.

In some embodiments, $R_5$ in Formula (I) is independently halogen, amino, hydroxyl, $C_{1-12}$ alkyl, $C_{1-12}$ alkoxyl, $C_{1-12}$ alky-OH, $C_{1-12}$ haloalkyl or $OR_6$, which is mono- or multi-substituted by deuterium.

In some embodiments, W in Formula (I) is O.

In some embodiments, A in Formula (I) is O.

In some embodiments, $R_3$ in Formula (I) is 3-10 membered saturated or unsaturated heterocyclyl which is mono- or multi-substituted by deuterium.

In some embodiments, $R_3$ in Formula (I) is 3-10 membered saturated heterocyclyl, which can be optionally mono- or independently multi- substituted by halogen, hydroxyl, amino, $C_{1-12}$ alkyl, $C_{1-12}$ alkoxyl, $C_{1-12}$ alky-OH, $C_{1-12}$ haloalkyl, $C_{1-12}$ alkyl.

In some embodiments, $R_3$ in Formula (I) is 3-10 membered saturated heterocyclyl, mono- or independently multi-substituted by deuterium substituted $C_{1-12}$ alkyl.

In some embodiments, $R_3$ in Formula (I) is 5-10 membered saturated heterocyclyl containing one or two N atoms, which can be optionally mono- or independently multi-substituted by halogen, deuterium, hydroxyl, amino, $C_{1-12}$ alkyl, $C_{1-12}$ alkoxyl, $C_{1-12}$ alky-OH, $C_{1-12}$ haloalkyl, or deuterium substituted $C_{1-12}$ alkyl. In certain embodiments, $R_3$ in Formula (I) contains at least one halogen substituent, preferably the halogen is F. In certain embodiments, $R_3$ in Formula (I) contains two, three or more halogen substituents, preferably the halogen is F.

In some embodiments, $R_3$ in Formula (I) is

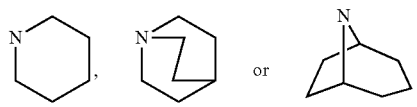

which can be optionally mono- or independently multi-substituted by halogen, deuterium, hydroxyl, amino, $C_{1-12}$ alkyl, $C_{1-12}$ alkoxyl, $C_{1-12}$ alky-OH, $C_{1-12}$ haloalkyl, or deuterium substituted $C_{1-12}$ alkyl.

In some embodiments, $R_3$ in Formula (I) is

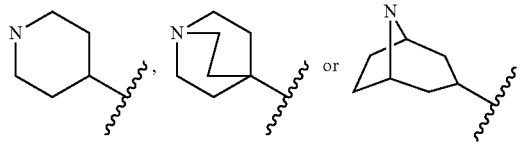

which can be optionally mono- or independently multi-substituted by halogen, deuterium, hydroxyl, amino, $C_{1-12}$ alkyl, $C_{1-12}$ alkoxyl, $C_{1-12}$ alky-OH, $C_{1-12}$ haloalkyl, or deuterium substituted $C_{1-12}$ alkyl.

In some embodiments, Y in Formula (I) is bond or $C_{1-3}$ alkylene.

In some embodiments, E in Formula (I) is

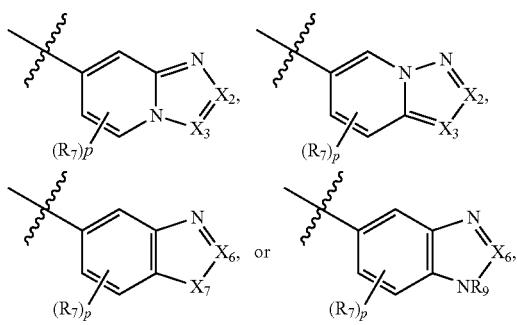

wherein,
$X_2$ and $X_3$ are each independently N or $CR_8$;
$X_6$ is N or $CR_8$, and $X_7$ is O, S, $NR_9$ or $CR_{10}R_{11}$;
p is 0, 1, 2 or 3, and
each $R_7$ is independently halogen, amino, hydroxyl, $C_{1-12}$ alkyl, $C_{1-12}$ alkoxyl, $C_{1-12}$ alky-OH, or $C_{1-12}$ haloalkyl;
$R_8$, $R_9$, $R_{10}$, and $R_{11}$ are each independently hydrogen, halogen, $C_{1-12}$ alkyl, cyano, amino, hydroxyl, $C_{1-12}$ alkoxyl, $C_{1-12}$ alky-OH, or $C_{1-12}$ haloalkyl.

In some embodiments, E in Formula (I) is

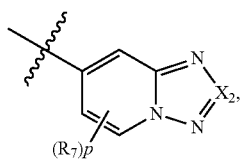

wherein $X_2$ is N or $CR_8$.

In some embodiments, the compounds of the present disclosure are represented by Formula (Ia):

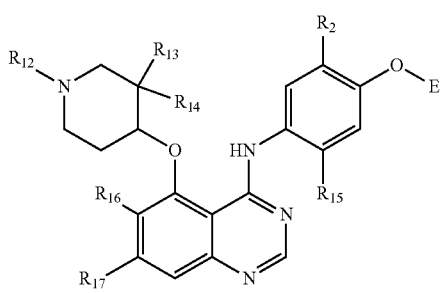

Formula (Ia)

or a pharmaceutically acceptable salt, ester, hydrate, solvate or stereoisomer thereof, wherein,
$R_2$ is hydrogen, halogen, hydroxyl, $C_{1-12}$ alkyl, $C_{1-12}$ alkoxyl, $C_{1-12}$ alky-OH, or $C_{1-12}$ haloalkyl;
$R_{12}$, $R_{13}$, $R_{14}$ and $R_{15}$ are each independently hydrogen, halogen, deuterium, hydroxyl, amino, $C_{1-12}$ alkyl, $C_{1-12}$ alkoxyl, $C_{1-12}$ alky-OH, $C_{1-12}$ haloalkyl, deuterium substituted $C_{1-12}$ alkyl;

$R_{16}$ and $R_{17}$ are each independently hydrogen, halogen, amino, hydroxyl, $C_{1-12}$ alkyl, $C_{1-12}$ alkoxyl, $C_{1-12}$ alky-OH, $C_{1-12}$ haloalkyl or $OR_6$; wherein $R_6$ is 3-10 membered saturated or unsaturated carbocyclyl, or 3-10 membered saturated or unsaturated heterocyclyl optionally mono- or independently multi-substituted by hydroxyl, halogen, cyano, $C_{1-12}$ alkyl, or $C_{1-12}$ haloalkyl;
wherein E is

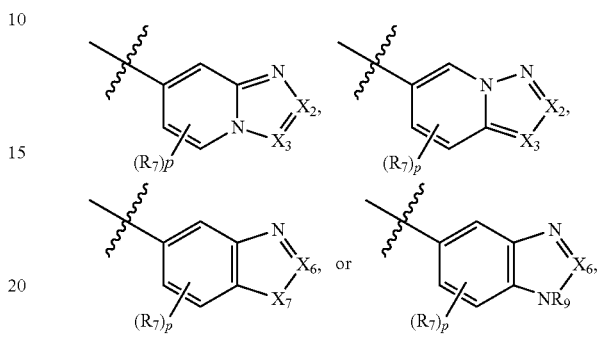

wherein
$X_2$ and $X_3$ are each independently N or $CR_8$;
$X_6$ is each independently N or $CR_8$, and $X_7$ is O, S, $NR_9$ or $CR_{10}R_{11}$;
p is 0, 1, 2 or 3, and
each $R_7$ is independently halogen, amino, hydroxyl, $C_{1-12}$ alkyl, $C_{1-12}$ alkoxyl, $C_{1-12}$ alky-OH, or $C_{1-12}$ haloalkyl;
$R_8$, $R_9$, $R_{10}$, and $R_{11}$ are each independently hydrogen, halogen, $C_{1-12}$ alkyl, cyano, amino, hydroxyl, $C_{1-12}$ alkoxyl, $C_{1-12}$ alky-OH, or $C_{1-12}$ haloalkyl.

In some embodiments, $R_2$ in Formula (Ia) is halogen, hydroxyl, $C_{1-12}$ alkyl, or $C_{1-12}$ alkoxyl.

In some embodiments, $R_{12}$, $R_{13}$, $R_{14}$ and $R_{15}$ in Formula (Ia) are each independently hydrogen, halogen, deuterium, hydroxyl, amino, $C_{1-12}$ alkyl, or $C_{1-12}$ alkoxyl.

In some embodiments, at least one of $R_{13}$ and $R_{14}$ in Formula (Ia) is halogen. In some embodiments, both of $R_{13}$ and $R_{14}$ in Formula (Ia) are halogen. In some embodiments, at least one of $R_{13}$ and $R_{14}$ in Formula (Ia) is F. In some embodiments, both of $R_{13}$ and $R_{14}$ in Formula (Ia) are F. In some embodiments, $R_{15}$ in Formula (Ia) is hydrogen. In some embodiments, $R_{15}$ in Formula (Ia) is halogen.

In some embodiments, $R_{16}$ and $R_{17}$ in Formula (Ia) are each independently hydrogen, halogen, amino, $C_{1-12}$ alkoxyl, or $OR_6$, which can be optionally mono- or independently multi-substituted by deuterium; wherein $R_6$ is 3-10 membered saturated or unsaturated carbocyclyl, or 3-10 membered saturated or unsaturated heterocyclyl optionally mono- or independently multi-substituted by hydroxyl, halogen, cyano, $C_{1-12}$ alkyl, or $C_{1-12}$ haloalkyl. In some embodiments, $R_{16}$ and $R_{17}$ in Formula (Ia) are each independently hydrogen, amino, or $C_{1-12}$ alkoxyl.

In some embodiments, E in Formula (Ia) contains at least two or three N atoms.

In some embodiments, E in Formula (Ia) is

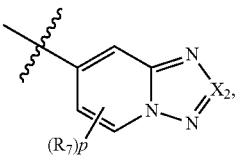

wherein $X_2$ is $CR_8$ and $R_8$ is hydrogen, halogen, $C_{1-12}$ alkyl, cyano, amino, hydroxyl, or $C_{1-12}$ alkoxyl.

In some embodiments, E in Formula (Ia) is

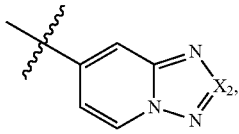

wherein $X_2$ is $CR_8$ and $R_8$ is hydrogen, halogen, $C_{1-12}$ alkyl, cyano, amino, hydroxyl, or $C_{1-12}$ alkoxyl. In some embodiments, E in Formula (Ia) is

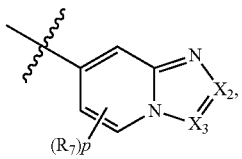

wherein $X_2$ and $X_3$ are each independently $CR_8$ and $R_8$ is hydrogen, halogen, $C_{1-12}$ alkyl, cyano, amino, hydroxyl, or $C_{1-12}$ alkoxyl.

Exemplary compounds 1-46 of Formula (I) are set forth in Table 1 below.

TABLE 1

Exemplary Compounds 1-56

| Compound No. | Compound Structure and Nomenclature |
|---|---|
| 1/1' | *enantiomerically pure enantiomer<br><br>N-(4-([1,2,4]triazolo[1,5-a]pyridin-7-yloxy)-3-methylphenyl)-5-((3,3-difluoro-1-methylpiperidin-4-yl)oxy)quinazolin-4-amine |
| 2 | N-(4-([1,2,4]triazolo[1,5-a]pyridin-7-yloxy)-3-methylphenyl)-5-(((1R,3r,5S)-8-(2,2-difluoroethyl)-8-azabicyclo[3.2.1]octan-3-yl)oxy)quinazolin-4-amine |
| 3 | *enantiomerically pure cis isomer<br><br>N-(4-([1,2,4]triazolo[1,5-a]pyridin-7-yloxy)-3-methylphenyl)-5-((3-fluoro-1-methylpiperidin-4-yl)oxy)-6-methoxyquinazolin-4-amine |

TABLE 1-continued

Exemplary Compounds 1-56

| Compound No. | Compound Structure and Nomenclature |
|---|---|
| 4 | 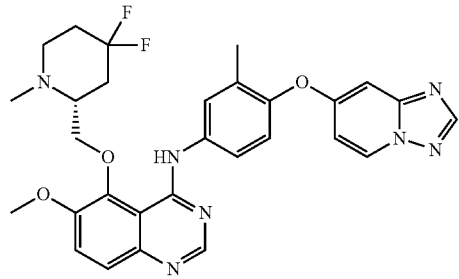 [SMILES: COc1ccc2ncnc(Nc3ccc(Oc4ccn5ncnc5c4)c(C)c3)c2c1OC[C@H]1CC(F)(F)CCN1C]<br>(R)-N-(4-([1,2,4]triazolo[1,5-a]pyridin-7-yloxy)-3-methylphenyl)-5-((4,4-difluoro-1-methylpiperidin-2-yl)methoxy)-6-methoxyquinazolin-4-amine |
| 5 | 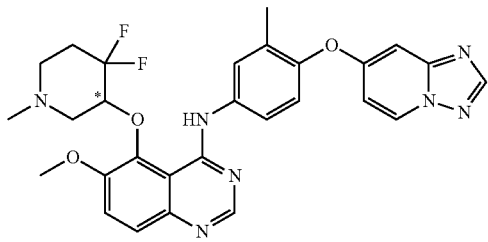 [SMILES: COc1ccc2ncnc(Nc3ccc(Oc4ccn5ncnc5c4)c(C)c3)c2c1OC1CN(C)CCC1(F)F]<br>*enantiomerically pure isomer<br>N-(4-([1,2,4]triazolo[1,5-a]pyridin-7-yloxy)-3-methylphenyl)-5-((4,4-difluoro-1-methylpiperidin-3-yl)oxy)-6-methoxyquinazolin-4-amine |
| 6 | 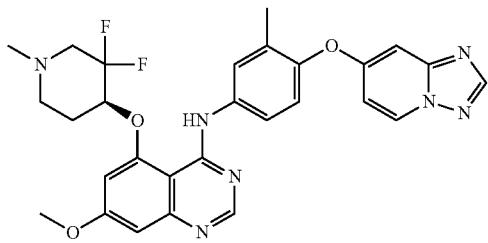 [SMILES: COc1cc(O[C@H]2CCN(C)CC2(F)F)c2c(Nc3ccc(Oc4ccn5ncnc5c4)c(C)c3)ncnc2c1]<br>enantiomer-1<br>(S)-N-(4-([1,2,4]triazolo[1,5-a]pyridin-7-yloxy)-3-methylphenyl)-5-((3,3-difluoro-1-methylpiperidin-4-yl)oxy)-7-methoxyquinazolin-4-amine |
| 6' | 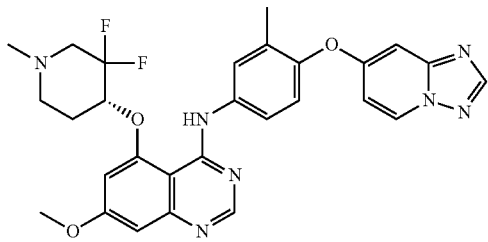 [SMILES: COc1cc(O[C@@H]2CCN(C)CC2(F)F)c2c(Nc3ccc(Oc4ccn5ncnc5c4)c(C)c3)ncnc2c1]<br>enantiomer-2<br>(R)-N-(4-([1,2,4]triazolo[1,5-a]pyridin-7-yloxy)-3-methylphenyl)-5-((3,3-difluoro-1-methylpiperidin-4-yl)oxy)-7-methoxyquinazolin-4-amine |

TABLE 1-continued

Exemplary Compounds 1-56

| Compound No. | Compound Structure and Nomenclature |
|---|---|
| 7 | 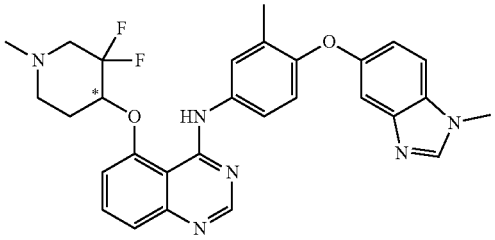<br>*enantiomerically pure isomer<br><br>5-((3,3-difluoro-1-methylpiperidin-4-yl)oxy)-N-(3-methyl-4-((1-methyl-1H-benzo[d]imidazol-5-yl)oxy)phenyl)quinazolin-4-amine |
| 8 | 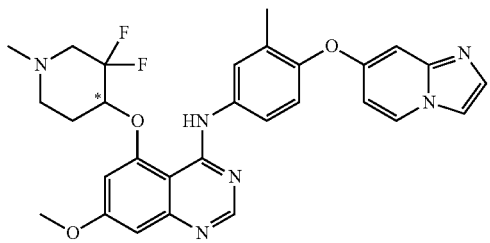 [SMILES: COc1cc(OC2CCN(C)CC2(F)F)c2c(Nc3ccc(Oc4ccn5ccnc5c4)c(C)c3)ncnc2c1]<br>*enantiomerically pure isomer<br><br>5-((3,3-difluoro-1-methylpiperidin-4-yl)oxy)-N-(4-(imidazo[1,2-a]pyridin-7-yloxy)-3-methylphenyl)-7-methoxyquinazolin-4-amine |
| 9 | 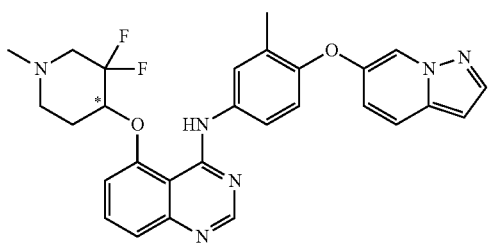 [SMILES: Cc1cc(Nc2ncnc3cccc(OC4CCN(C)CC4(F)F)c23)ccc1Oc1ccc2ccnn2c1]<br>*enantiomerically pure isomer<br><br>5-((3,3-difluoro-1-methylpiperidin-4-yl)oxy)-N-(3-methyl-4-(pyrazolo[1,5-a]pyridin-6-yloxy)phenyl)quinazolin-4-amine |
| 10 | 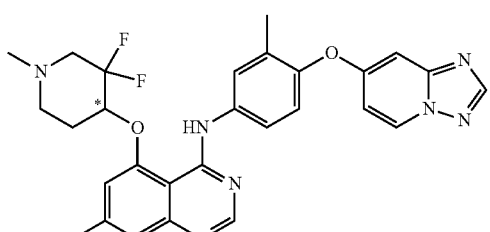<br>*enantiomerically pure isomer<br><br>$N^4$-(4-([1,2,4]triazolo[1,5-a]pyridin-7-yloxy)-3-methylphenyl)-5-((3,3-difluoro-1-methylpiperidin-4-yl)oxy)quinazoline-4,7-diamine |

TABLE 1-continued

Exemplary Compounds 1-56

| Compound No. | Compound Structure and Nomenclature |
|---|---|
| 11 | 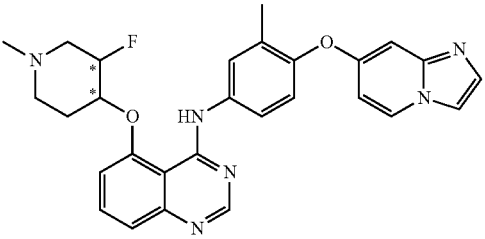 [SMILES: Cc1cc(Nc2ncnc3cccc(OC4CCN(C)CC4F)c23)ccc1Oc1ccn2ccnc2c1]<br>*enantiomerically pure cis-isomer<br><br>5-(((3S,4R)-3-fluoro-1-methylpiperidin-4-yl)oxy)-N-(4-(imidazo[1,2-a]pyridin-7-yloxy)-3-methylphenyl)quinazolin-4-amine |
| 12/12' | 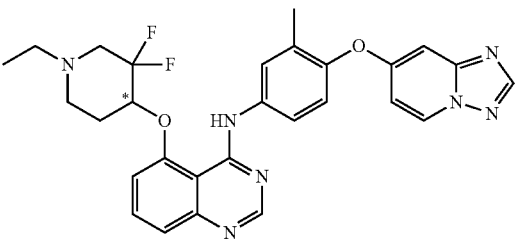 [SMILES: CCN1CCC(Oc2cccc3ncnc(Nc4ccc(Oc5ccn6ncnc6c5)c(C)c4)c23)C(F)(F)C1]<br>*12 = enantiomer-1; 12' = enantiomer-2<br><br>(S)-N-(4-([1,2,4]triazolo[1,5-a]pyridin-7-yloxy)-3-methylphenyl)-5-((1-ethyl-3,3-difluoropiperidin-4-yl)oxy)quinazolin-4-amine<br>And<br>(R)-N-(4-([1,2,4]triazolo[1,5-a]pyridin-7-yloxy)-3-methylphenyl)-5-((1-ethyl-3,3-difluoropiperidin-4-yl)oxy)quinazolin-4-amine |
| 13 | 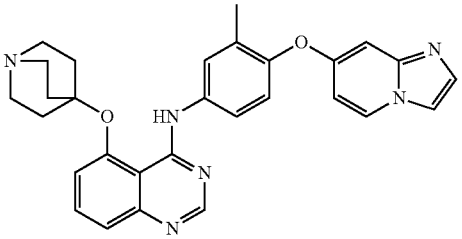 [SMILES: Cc1cc(Nc2ncnc3cccc(OC45CCN(CC4)CC5)c23)ccc1Oc1ccn2ccnc2c1]<br>N-(4-(imidazo[1,2-a]pyridin-7-yloxy)-3-methylphenyl)-5-(quinuclidin-4-yloxy)quinazolin-4-amine |
| 14/14' | 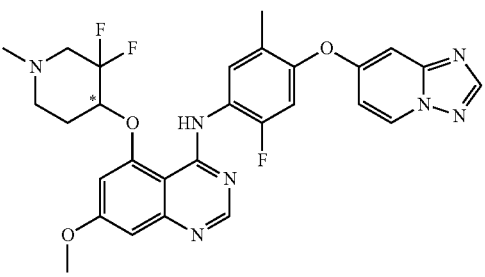 [SMILES: COc1cc(OC2CCN(C)CC2(F)F)c2c(Nc3cc(C)c(Oc4ccn5ncnc5c4)cc3F)ncnc2c1]<br>*14 = enantiomer-1; 14' = enantiomer-2<br><br>(S)-N-(4-([1,2,4]triazolo[1,5-a]pyridin-7-yloxy)-2-fluoro-5-methylphenyl)-5-((3,3-difluoro-1-methylpiperidin-4-yl)oxy)-7-methoxyquinazolin-4-amine<br>And<br>(R)-N-(4-([1,2,4]triazolo[1,5-a]pyridin-7-yloxy)-2-fluoro-5-methylphenyl)-5-((3,3-difluoro-1-methylpiperidin-4-yl)oxy)-7-methoxyquinazolin-4-amine |

TABLE 1-continued

Exemplary Compounds 1-56

| Compound No. | Compound Structure and Nomenclature |
|---|---|
| 15/15' | 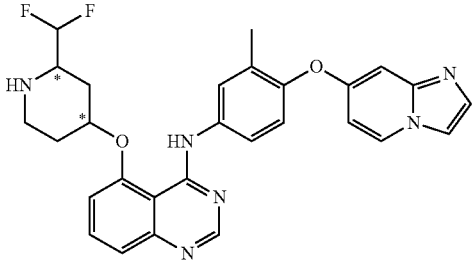 [SMILES: Cc1cc(Nc2ncnc3cccc(OC4CCNC(C(F)F)C4)c23)ccc1Oc1ccn2ccnc2c1]<br>*15 = racemic trans isomer; 15' = racemic cis isomer<br><br>(±)-(5-(((2S,4S)-2-(difluoromethyl)piperidin-4-yl)oxy)-N-(4-(imidazo[1,2-a]pyridin-7-yloxy)-3-methylphenyl)quinazolin-4-amine<br>And<br>(±)-(5-(((2R,4S)-2-(difluoromethyl)piperidin-4-yl)oxy)-N-(4-(imidazo[1,2-a]pyridin-7-yloxy)-3-methylphenyl)quinazolin-4-amine |
| 16 | 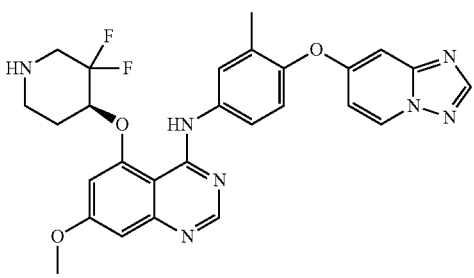 [SMILES: COc1cc(O[C@H]2CCNCC2(F)F)c2c(Nc3ccc(Oc4ccn5ncnc5c4)c(C)c3)ncnc2c1]<br><br>(S)-N-(4-([1,2,4]triazolo[1,5-a]pyridin-7-yloxy)-3-methylphenyl)-5-((3,3-difluoropiperidin-4-yl)oxy)-7-methoxyquinazolin-4-amine |
| 17/17' | 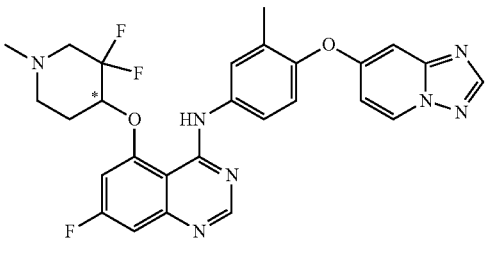 [SMILES: Cc1cc(Nc2ncnc3cc(F)cc(OC4CCN(C)CC4(F)F)c23)ccc1Oc1ccn2ncnc2c1]<br>*17 = enantiomer-1; 17' = enantiomer-2<br><br>(S)-N-(4-([1,2,4]triazolo[1,5-a]pyridin-7-yloxy)-3-methylphenyl)-5-((3,3-difluoro-1-methylpiperidin-4-yl)oxy)-7-fluoroquinazolin-4-amine<br>And<br>(R)-N-(4-([1,2,4]triazolo[1,5-a]pyridin-7-yloxy)-3-methylphenyl)-5-((3,3-difluoro-1-methylpiperidin-4-yl)oxy)-7-fluoroquinazolin-4-amine |
| 18 | 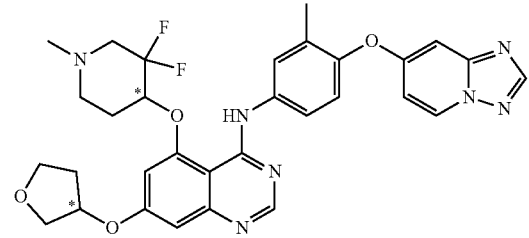 [SMILES: Cc1cc(Nc2ncnc3cc(OC4CCOC4)cc(OC4CCN(C)CC4(F)F)c23)ccc1Oc1ccn2ncnc2c1]<br>*enantiomerically pure isomer<br><br>N-(4-([1,2,4]triazolo[1,5-a]pyridin-7-yloxy)-3-methylphenyl)-5-((3,3-difluoro-1-methylpiperidin-4-yl)oxy)-7-((tetrahydrofuran-3-yl)oxy)quinazolin-4-amine |

TABLE 1-continued

Exemplary Compounds 1-56

| Compound No. | Compound Structure and Nomenclature |
|---|---|
| 19/19' | 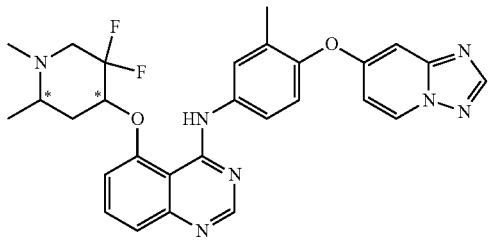 [SMILES: Cc1cc(Nc2ncnc3cccc(OC4CC(C)N(C)CC4(F)F)c23)ccc1Oc1ccn2ncnc2c1]<br>*19 = trans enantiomer-1; 19' = cis enantiomer-2<br><br>N-(4-([1,2,4]triazolo[1,5-a]pyridin-7-yloxy)-3-methylphenyl)-5-(((2S,4S)-5,5-difluoro-1,2-dimethylpiperidin-4-yl)oxy)quinazolin-4-amine<br>And<br>N-(4-([1,2,4]triazolo[1,5-a]pyridin-7-yloxy)-3-methylphenyl)-5-(((2R,4R)-5,5-difluoro-1,2-dimethylpiperidin-4-yl)oxy)quinazolin-4-amine |
| 20 | 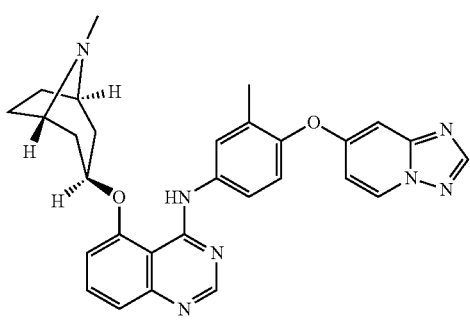 [SMILES: Cc1cc(Nc2ncnc3cccc(O[C@@H]4C[C@H]5CC[C@@H](C4)N5C)c23)ccc1Oc1ccn2ncnc2c1]<br>N-(4-([1,2,4]triazolo[1,5-a]pyridin-7-yloxy)-3-methylphenyl)-5-(((1R,3s,5S)-8-methyl-8-azabicyclo[3.2.1]octan-3-yl)oxy)quinazolin-4-amine |
| 21 | 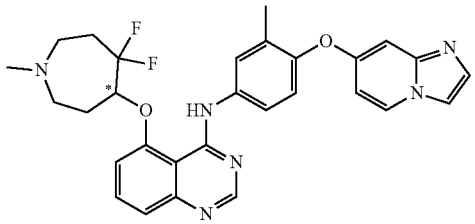 [SMILES: Cc1cc(Nc2ncnc3cccc(OC4CCN(C)CCC4(F)F)c23)ccc1Oc1ccn2ccnc2c1]<br>*enantiomerically pure isomer<br><br>5-((5,5-difluoro-1-methylazepan-4-yl)oxy)-N-(4-(imidazo[1,2-a]pyridin-7-yloxy)-3-methylphenyl)quinazolin-4-amine |
| 22 | 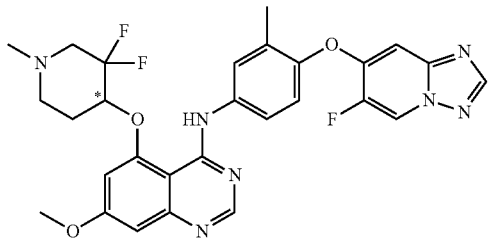 [SMILES: COc1cc(OC2CCN(C)CC2(F)F)c2c(Nc3ccc(Oc4cc5ncnn5cc4F)c(C)c3)ncnc2c1]<br>*enantiomerically pure isomer<br><br>5-((3,3-difluoro-1-methylpiperidin-4-yl)oxy)-N-(4-((6-fluoro-[1,2,4]triazolo[1,5-a]pyridin-7-yl)oxy)-3-methylphenyl)-7-methoxyquinazolin-4-amine |

TABLE 1-continued

Exemplary Compounds 1-56

| Compound No. | Compound Structure and Nomenclature |
|---|---|
| 23 | 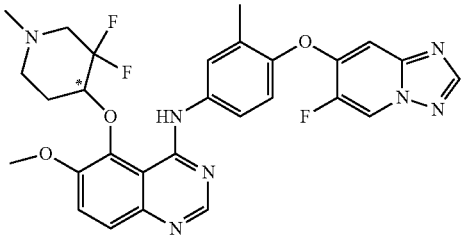 [SMILES: COc1ccc2ncnc(Nc3ccc(Oc4cc5ncnn5cc4F)c(C)c3)c2c1OC1CCN(C)CC1(F)F]<br>*enantiomerically pure isomer<br><br>5-((3,3-difluoro-1-methylpiperidin-4-yl)oxy)-N-(4-((6-fluoro-[1,2,4]triazolo[1,5-a]pyridin-7-yl)oxy)-3-methylphenyl)-6-methoxyquinazolin-4-amine |
| 24 | 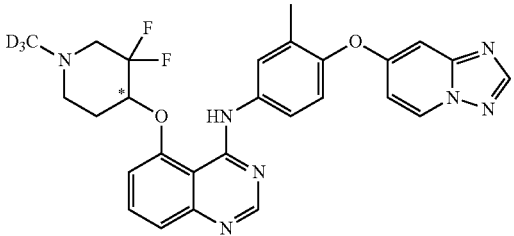 [SMILES: [2H]C([2H])([2H])N1CCC(Oc2cccc3ncnc(Nc4ccc(Oc5ccn6ncnc6c5)c(C)c4)c23)C(F)(F)C1]<br>*enantiomerically pure isomer<br><br>N-(4-([1,2,4]triazolo[1,5-a]pyridin-7-yloxy)-3-methylphenyl)-5-((3,3-difluoro-1-(methyl-d3)piperidin-4-yl)oxy)quinazolin-4-amine |
| 25 | 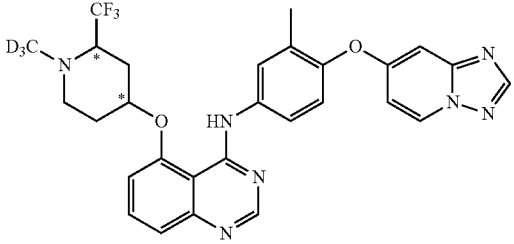 [SMILES: [2H]C([2H])([2H])N1CCC(Oc2cccc3ncnc(Nc4ccc(Oc5ccn6ncnc6c5)c(C)c4)c23)CC1C(F)(F)F]<br>*racemic cis isomer<br><br>(±)-N-(4-([1,2,4]triazolo[1,5-a]pyridin-7-yloxy)-3-methylphenyl)-5-(((2R,4S)-1-(methyl-d$_3$)-2-(trifluoromethyl)piperidin-4-yl)oxy)quinazolin-4-amine |
| 26 | 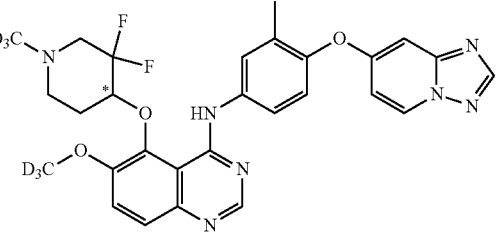<br>*racemic<br><br>(±)-N-(4-([1,2,4]triazolo[1,5-a]pyridin-7-yloxy)-3-methylphenyl)-5-((3,3-difluoro-1-(methyl-d$_3$)piperidin-4-yl)oxy)-6-(methoxy-d$_3$)quinazolin-4-amine |

TABLE 1-continued

Exemplary Compounds 1-56

| Compound No. | Compound Structure and Nomenclature |
|---|---|
| 27 | 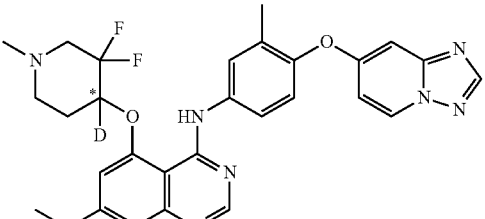<br>*racemic<br><br>(±)-N-(4-([1,2,4]triazolo[1,5-a]pyridin-7-yloxy)-3-methylphenyl)-5-((3,3-difluoro-1-methylpiperidin-4-yl-4-d)oxy)-7-methoxyquinazolin-4-amine |
| 28/28' | 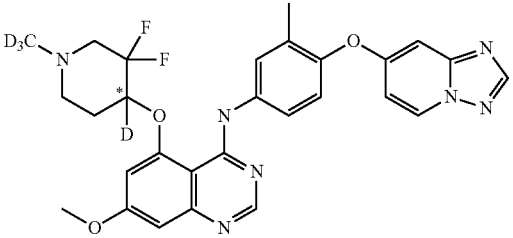 [SMILES: [2H]C([2H])([2H])N1CCC([2H])(Oc2cc(OC)cc3ncnc(Nc4ccc(Oc5ccn6ncnc6c5)c(C)c4)c23)C(F)(F)C1]<br>*28 = enantiomer-1; 28' = enantiomer-2<br><br>(S)-N-(4-([1,2,4]triazolo[1,5-a]pyridin-7-yloxy)-3-methylphenyl)-5-((3,3-difluoro-1-(methyl-d$_3$)piperidin-4-yl-4-d)oxy)-7-methoxyquinazolin-4-amine<br>And<br>(R)-N-(4-([1,2,4]triazolo[1,5-a]pyridin-7-yloxy)-3-methylphenyl)-5-((3,3-difluoro-1-(methyl-d$_3$)piperidin-4-yl-4-d)oxy)-7-methoxyquinazolin-4-amine |
| 29 | 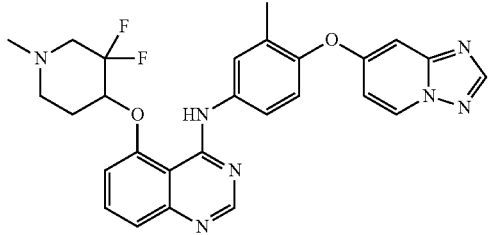 [SMILES: Cc1cc(Nc2ncnc3cccc(OC4CCN(C)CC4(F)F)c23)ccc1Oc1ccn2ncnc2c1]<br><br>N-(4-([1,2,4]triazolo[1,5-a]pyridin-7-yloxy)-3-methylphenyl)-5-((3,3-difluoro-1-methylpiperidin-4-yl)oxy)quinazolin-4-amine |
| 30 | 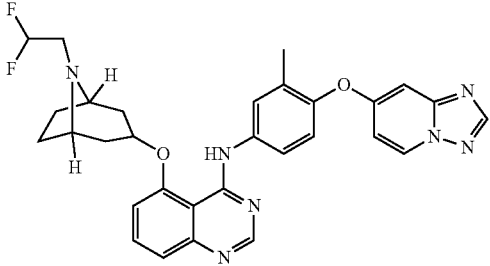 [SMILES: Cc1cc(Nc2ncnc3cccc(OC4CC5CCC(C4)N5CC(F)F)c23)ccc1Oc1ccn2ncnc2c1]<br><br>N-(4-([1,2,4]triazolo[1,5-a]pyridin-7-yloxy)-3-methylphenyl)-5-((8-(2,2-difluoroethyl)-8-azabicyclo[3.2.1]octan-3-yl)oxy)quinazolin-4-amine |

TABLE 1-continued

Exemplary Compounds 1-56

| Compound No. | Compound Structure and Nomenclature |
|---|---|
| 31 | 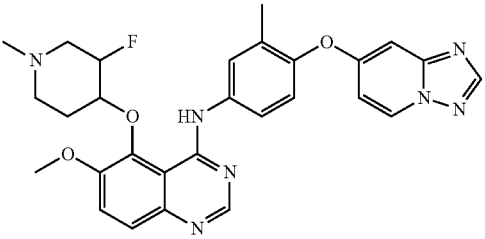 [SMILES: COc1ccc2ncnc(Nc3ccc(Oc4ccn5ncnc5c4)c(C)c3)c2c1OC1CCN(C)CC1F]<br>N-(4-([1,2,4]triazolo[1,5-a]pyridin-7-yloxy)-3-methylphenyl)-5-((3-fluoro-1-methylpiperidin-4-yl)oxy)-6-methoxyquinazolin-4-amine |
| 32 | 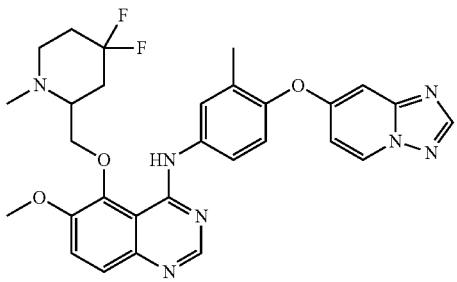 [SMILES: COc1ccc2ncnc(Nc3ccc(Oc4ccn5ncnc5c4)c(C)c3)c2c1OCC1CC(F)(F)CCN1C]<br>N-(4-([1,2,4]triazolo[1,5-a]pyridin-7-yloxy)-3-methylphenyl)-5-((4,4-difluoro-1-methylpiperidin-2-yl)methoxy)-6-methoxyquinazolin-4-amine |
| 33 | 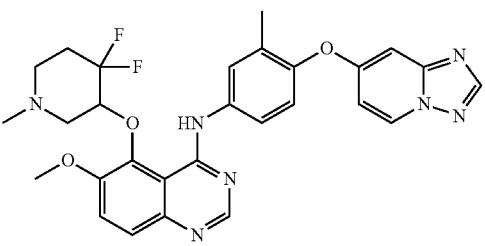 [SMILES: COc1ccc2ncnc(Nc3ccc(Oc4ccn5ncnc5c4)c(C)c3)c2c1OC1CN(C)CCC1(F)F]<br>N-(4-([1,2,4]triazolo[1,5-a]pyridin-7-yloxy)-3-methylphenyl)-5-((4,4-difluoro-1-methylpiperidin-3-yl)oxy)-6-methoxyquinazolin-4-amine |
| 34 | 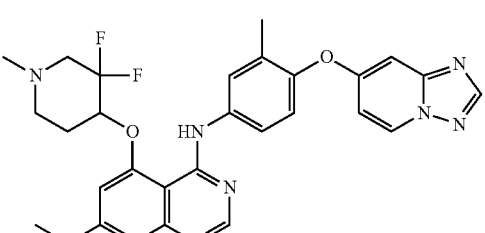<br>N-(4-([1,2,4]triazolo[1,5-a]pyridin-7-yloxy)-3-methylphenyl)-5-((3,3-difluoro-1-methylpiperidin-4-yl)oxy)-7-methoxyquinazolin-4-amine |
| 35 | 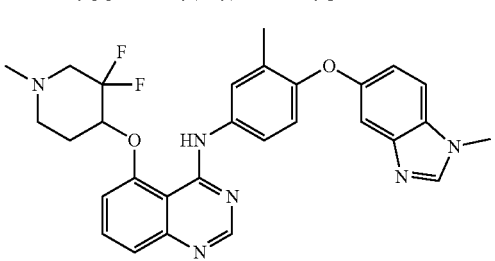 |

TABLE 1-continued

Exemplary Compounds 1-56

| Compound No. | Compound Structure and Nomenclature |
|---|---|

5-((3,3-difluoro-1-methylpiperidin-4-yl)oxy)-N-(3-methyl-4-((1-methyl-1H-benzo[d]imidazol-5-yl)oxy)phenyl)quinazolin-4-amine 36 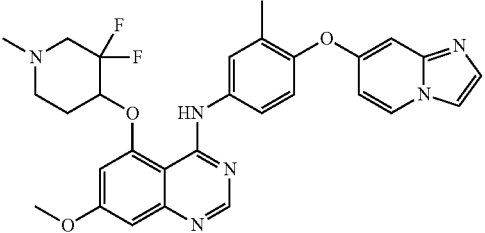 [SMILES: COc1cc(OC2CCN(C)CC2(F)F)c2c(Nc3ccc(Oc4ccn5ccnc5c4)c(C)c3)ncnc2c1]

5-((3,3-difluoro-1-methylpiperidin-4-yl)oxy)-N-(4-(imidazo[1,2-a]pyridin-7-yloxy)-3-methylphenyl)-7-methoxyquinazolin-4-amine 37 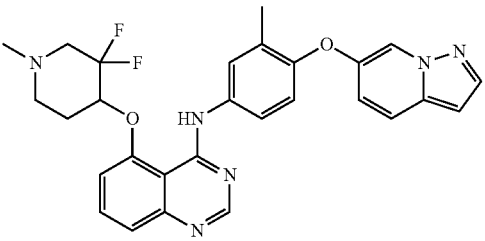 [SMILES: Cc1cc(Nc2ncnc3cccc(OC4CCN(C)CC4(F)F)c23)ccc1Oc1ccc2ccnn2c1]

5-((3,3-difluoro-1-methylpiperidin-4-yl)oxy)-N-(3-methyl-4-(pyrazolo[1,5-a]pyridin-6-yloxy)phenyl)quinazolin-4-amine 38 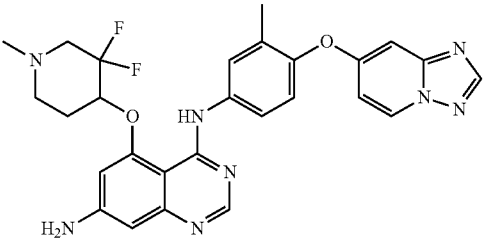 [SMILES: Cc1cc(Nc2ncnc3cc(N)cc(OC4CCN(C)CC4(F)F)c23)ccc1Oc1ccn2ncnc2c1]

$N^4$-(4-([1,2,4]triazolo[1,5-a]pyridin-7-yloxy)-3-methylphenyl)-5-((3,3-difluoro-1-methylpiperidin-4-yl)oxy)quinazoline-4,7-diamine 39 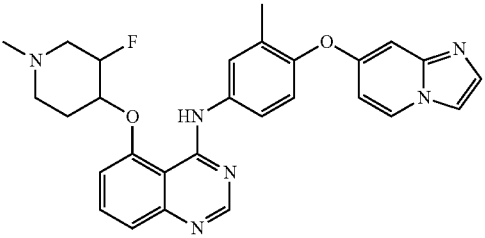 [SMILES: Cc1cc(Nc2ncnc3cccc(OC4CCN(C)CC4F)c23)ccc1Oc1ccn2ccnc2c1]

5-((3-fluoro-1-methylpiperidin-4-yl)oxy)-N-(4-(imidazo[1,2-a]pyridin-7-yloxy)-3-methylphenyl)quinazolin-4-amine TABLE 1-continued Exemplary Compounds 1-56

| Compound No. | Compound Structure and Nomenclature |
|---|---|
| 40 | 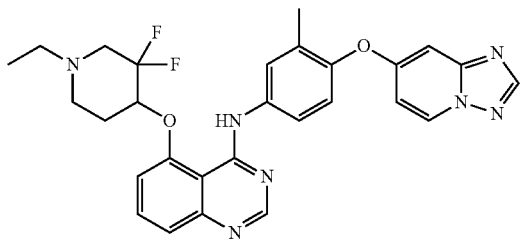 [SMILES: CCN1CCC(Oc2cccc3ncnc(Nc4ccc(Oc5ccn6ncnc6c5)c(C)c4)c23)C(F)(F)C1]<br>N-(4-([1,2,4]triazolo[1,5-a]pyridin-7-yloxy)-3-methylphenyl)-5-((1-ethyl-3,3-difluoropiperidin-4-yl)oxy)quinazolin-4-amine |
| 41 | 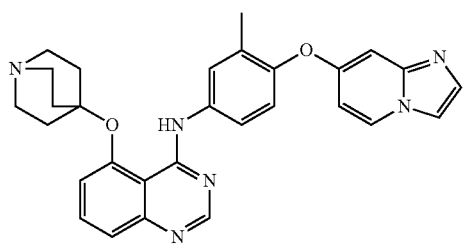 [SMILES: Cc1cc(Nc2ncnc3cccc(OC45CCN(CC4)CC5)c23)ccc1Oc1ccn2ccnc2c1]<br>N-(4-(imidazo[1,2-a]pyridin-7-yloxy)-3-methylphenyl)-5-(quinuclidin-4-yloxy)quinazolin-4-amine |
| 42 | 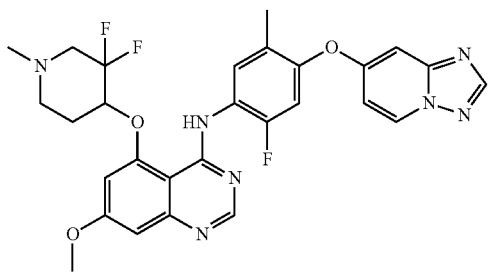 [SMILES: COc1cc(OC2CCN(C)CC2(F)F)c2c(Nc3cc(C)c(Oc4ccn5ncnc5c4)cc3F)ncnc2c1]<br>N-(4-([1,2,4]triazolo[1,5-a]pyridin-7-yloxy)-2-fluoro-5-methylphenyl)-5-((3,3-difluoro-1-methylpiperidin-4-yl)oxy)-7-methoxyquinazolin-4-amine |
| 43 | 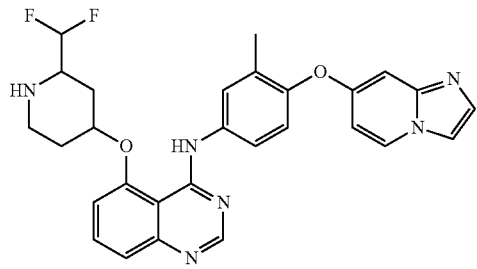 [SMILES: Cc1cc(Nc2ncnc3cccc(OC4CCNC(C(F)F)C4)c23)ccc1Oc1ccn2ccnc2c1]<br>(5-((2-(difluoromethyl)piperidin-4-yl)oxy)-N-(4-(imidazo[1,2-a]pyridin-7-yloxy)-3-methylphenyl)quinazolin-4-amine |

TABLE 1-continued

Exemplary Compounds 1-56

| Compound No. | Compound Structure and Nomenclature |
|---|---|
| 44 | 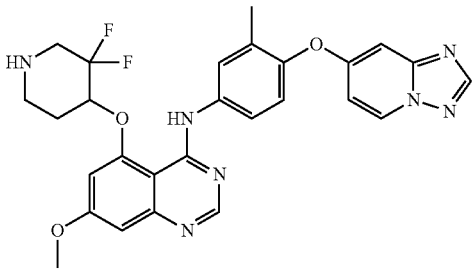 [SMILES: COc1cc(OC2CCNCC2(F)F)c2c(Nc3ccc(Oc4ccn5ncnc5c4)c(C)c3)ncnc2c1]<br>N-(4-([1,2,4]triazolo[1,5-a]pyridin-7-yloxy)-3-methylphenyl)-5-((3,3-difluoropiperidin-4-yl)oxy)-7-methoxyquinazolin-4-amine |
| 45 | 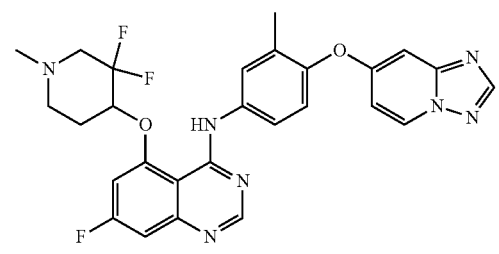 [SMILES: Cc1cc(Nc2ncnc3cc(F)cc(OC4CCN(C)CC4(F)F)c23)ccc1Oc1ccn2ncnc2c1]<br>N-(4-([1,2,4]triazolo[1,5-a]pyridin-7-yloxy)-3-methylphenyl)-5-((3,3-difluoro-1-methylpiperidin-4-yl)oxy)-7-fluoroquinazolin-4-amine |
| 46 | 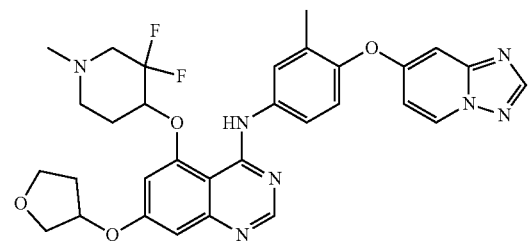 [SMILES: Cc1cc(Nc2ncnc3cc(OC4CCOC4)cc(OC4CCN(C)CC4(F)F)c23)ccc1Oc1ccn2ncnc2c1]<br>N-(4-([1,2,4]triazolo[1,5-a]pyridin-7-yloxy)-3-methylphenyl)-5-((3,3-difluoro-1-methylpiperidin-4-yl)oxy)-7-((tetrahydrofuran-3-yl)oxy)quinazolin-4-amine |
| 47 | 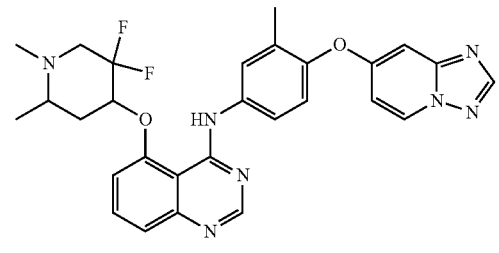 [SMILES: Cc1cc(Nc2ncnc3cccc(OC4CC(C)N(C)CC4(F)F)c23)ccc1Oc1ccn2ncnc2c1]<br>N-(4-([1,2,4]triazolo[1,5-a]pyridin-7-yloxy)-3-methylphenyl)-5-(((2R,4R)-5,5-difluoro-1,2-dimethylpiperidin-4-yl)oxy)quinazolin-4-amine |

TABLE 1-continued

Exemplary Compounds 1-56

| Compound No. | Compound Structure and Nomenclature |
|---|---|
| 48 | 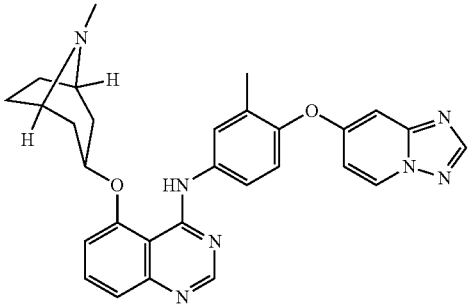 [SMILES: Cc1cc(Nc2ncnc3cccc(OC4CC5CCC(C4)N5C)c23)ccc1Oc1ccn2ncnc2c1]<br>N-(4-([1,2,4]triazolo[1,5-a]pyridin-7-yloxy)-3-methylphenyl)-5-((8-methyl-8-azabicyclo[3.2.1]octan-3-yl)oxy)quinazolin-4-amine |
| 49 | 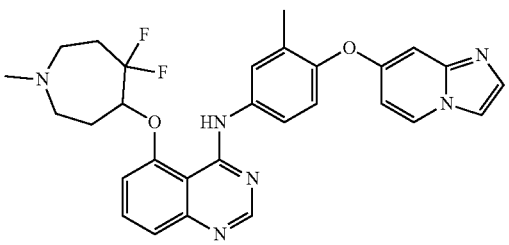 [SMILES: Cc1cc(Nc2ncnc3cccc(OC4CCN(C)CCC4(F)F)c23)ccc1Oc1ccn2ccnc2c1]<br>5-((5,5-difluoro-1-methylazepan-4-yl)oxy)-N-(4-(imidazo[1,2-a]pyridin-7-yloxy)-3-methylphenyl)quinazolin-4-amine |
| 50 | 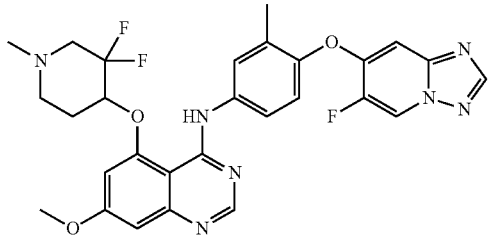 [SMILES: COc1cc(OC2CCN(C)CC2(F)F)c2c(Nc3ccc(Oc4cc5ncnn5cc4F)c(C)c3)ncnc2c1]<br>5-((3,3-difluoro-1-methylpiperidin-4-yl)oxy)-N-(4-((6-fluoro-[1,2,4]triazolo[1,5-a]pyridin-7-yl)oxy)-3-methylphenyl)-7-methoxyquinazolin-4-amine |
| 51 | 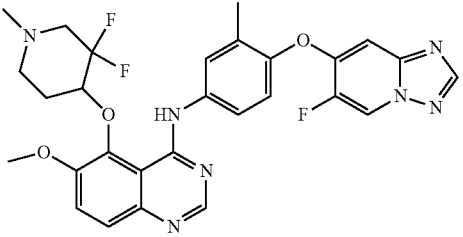 [SMILES: COc1ccc2ncnc(Nc3ccc(Oc4cc5ncnn5cc4F)c(C)c3)c2c1OC1CCN(C)CC1(F)F]<br>5-((3,3-difluoro-1-methylpiperidin-4-yl)oxy)-N-(4-((6-fluoro-[1,2,4]triazolo[1,5-a]pyridin-7-yl)oxy)-3-methylphenyl)-6-methoxyquinazolin-4-amine |

TABLE 1-continued

Exemplary Compounds 1-56

| Compound No. | Compound Structure and Nomenclature |
|---|---|
| 52 | 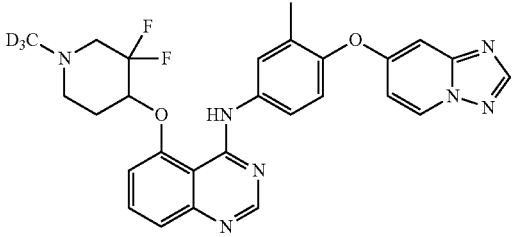 [SMILES: [2H]C([2H])([2H])N1CCC(Oc2cccc3ncnc(Nc4ccc(Oc5ccn6ncnc6c5)c(C)c4)c23)C(F)(F)C1]  N-(4-([1,2,4]triazolo[1,5-a]pyridin-7-yloxy)-3-methylphenyl)-5-((3,3-difluoro-1-(methyl-d3)piperidin-4-yl)oxy)quinazolin-4-amine |
| 53 | 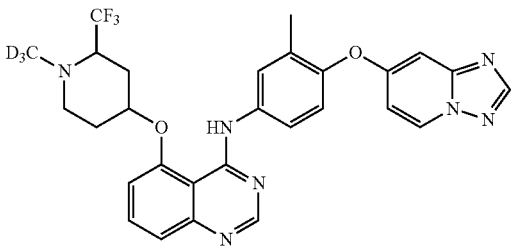 [SMILES: [2H]C([2H])([2H])N1CCC(Oc2cccc3ncnc(Nc4ccc(Oc5ccn6ncnc6c5)c(C)c4)c23)CC1C(F)(F)F]  N-(4-([1,2,4]triazolo[1,5-a]pyridin-7-yloxy)-3-methylphenyl)-5-((1-(methyl-d$_3$)-2-(trifluoromethyl)piperidin-4-yl)oxy)quinazolin-4-amine |
| 54 | 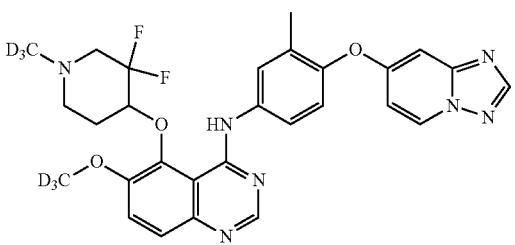 [SMILES: [2H]C([2H])([2H])Oc1ccc2ncnc(Nc3ccc(Oc4ccn5ncnc5c4)c(C)c3)c2c1OC1CCN(C([2H])([2H])[2H])CC1(F)F]  N-(4-([1,2,4]triazolo[1,5-a]pyridin-7-yloxy)-3-methylphenyl)-5-((3,3-difluoro-1-(methyl-d$_3$)piperidin-4-yl)oxy)-6-(methoxy-d$_3$)quinazolin-4-amine |
| 55 | 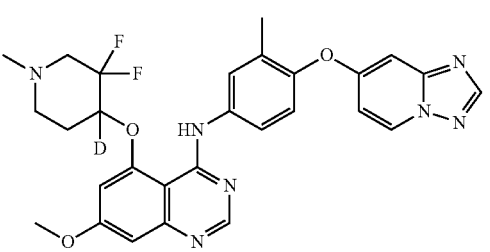 [SMILES: [2H]C1(Oc2cc(OC)cc3ncnc(Nc4ccc(Oc5ccn6ncnc6c5)c(C)c4)c23)CCN(C)CC1(F)F]  N-(4-([1,2,4]triazolo[1,5-a]pyridin-7-yloxy)-3-methylphenyl)-5-((3,3-difluoro-1-methylpiperidin-4-yl-4-d)oxy)-7-methoxyquinazolin-4-amine |

TABLE 1-continued

Exemplary Compounds 1-56

| Compound No. | Compound Structure and Nomenclature |
|---|---|
| 56 | 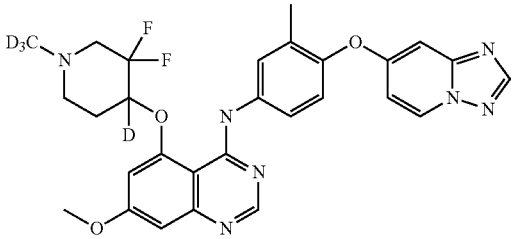 [SMILES: [2H]C([2H])([2H])N1CCC([2H])(Oc2cc(OC)cc3ncnc(Nc4ccc(Oc5ccn6ncnc6c5)c(C)c4)c23)C(F)(F)C1]<br>N-(4-([1,2,4]triazolo[1,5-a]pyridin-7-yloxy)-3-methylphenyl)-5-((3,3-difluoro-1-(methyl-d$_3$)piperidin-4-yl-4-d)oxy)-7-methoxyquinazolin-4-amine |

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable subcombination.

At various places in the present disclosure, linking substituents are described. Where the structure clearly requires a linking group, the markush variables listed for that group are understood to be linking groups. For example, if the structure requires a linking group and the markush group definition for that variable lists "alkyl", then it is understood that the "alkyl" represents a linking alkylene group.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate, fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{i\text{-}j}$" indicates a range of the carbon atoms numbers, wherein i and j are integers and the range of the carbon atoms numbers includes the endpoints (i.e. i and j) and each integer point in between, and wherein i∈{1, 2, 3, 4, 5, 6, 7, 8, 9, or 10}, j is greater than i, j∈{2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40}. For examples, $C_{1\text{-}6}$ indicates a range of one to six carbon atoms, including one carbon atom, two carbon atoms, three carbon atoms, four carbon atoms, five carbon atoms and six carbon atoms.

As used herein, the term "alkyl", whether as part of another term or used independently, refers to a saturated or unsaturated hydrocarbon chain, while the latter may be further subdivided into hydrocarbon chain having at least one double or triple bonds (alkenyl or alkynyl). The hydrocarbon chain mentioned above may be straight-chain or branched-chain. The term "$C_{i\text{-}j}$ alkyl" refers to an alkyl having i to j carbon atoms. In some embodiments, the alkyl group contains 1 to 12, 1 to 8, 1 to 6, 1 to 4, 1 to 3, or 1 to 2 carbon atoms. Examples of saturated alkyl group include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. Examples of unsaturated alkyl groups include, but are not limited to, ethenyl, n-propenyl, isopropenyl, n-butenyl, sec-butenyl, ethynyl, propyn-1-yl, propyn-2-yl, and the like.

As used herein the terms "halo" and "halogen" refer to an atom selected from fluorine, chlorine, bromine and iodine.

As used herein the terms "cyano" refers to a group of formula —CN.

As used herein, the term "hydroxyl" refers to a group of formula —OH.

As used herein, the term "alkoxy", whether as part of another term or used independently, refers to a group of formula —O-alkyl. The term "$C_{i\text{-}j}$ alkoxy" means that the alkyl moiety of the alkoxy group has i to j carbon atoms. In some embodiments, the alkyl moiety has 1 to 12, 1 to 10, 1 to 8, 1 to 6, 1 to 5, 1 to 4, 1 to 3 or 1 to 2 carbon atoms. Examples of alkoxy groups include, but are not limted to, methoxy, ethoxy, propoxy (e.g., n-propoxy and isopropoxy), t-butoxy, and the like.

As used herein, the term "$C_{i\text{-}j}$ alky-OH", refers to a group of formula "—$C_{1\text{-}12}$ alkyl-OH" wherein the alkyl moiety of the group has i to j carbon atoms, and the hydroxyl group may be linked to any carbon atoms in the alkyl moiety. In some embodiments, the alkyl moiety has 1 to 12, 1 to 10, 1 to 8, 1 to 6, 1 to 5, 1 to 4, 1 to 3 or 1 to 2 carbon atoms.

As used herein, the term "$C_{i\text{-}j}$ haloalkyl", refers to a halogen substituted (mono- or multi-substituted) $C_{i\text{-}j}$ alkyl group.

As used herein, the term "carbocyclyl", whether as part of another term or used independently, refers to any ring in which all the ring atoms are carbon and which contains at least three ring forming carbon atoms. In some embodiments, the carbocyclyl may contain 3 to 12 ring forming carbon atoms, 3 to 10 ring forming carbon atoms, 3 to 9 ring forming carbon atoms or 4 to 8 ring forming carbon atoms. Carbocyclyl groups may be saturated or partially unsaturated. In some embodiments, the carbocyclyl group may be a saturated cyclic alkyl group. In some embodiments, the carbocyclyl group may be an unsaturated cyclic alkyl group that contains at least one double bond in its ring system. In some embodiments, an unsaturated carbocyclyl group may contains one or more aromatic rings.

Carbocyclyl groups can include mono- or poly-cyclic ring(s) (e.g., having 2, 3 or 4 fused, bridged or spiro rings).

Examples of monocyclic carbocyclyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, and the like. As used herein, the term "spiro rings" refers to ring sytems having two rings connected through one single common atom; the term "fused rings" refers to ring systems having two rings sharing two adjacent atoms; and the term "bridged rings" refers to ring systems with two rings sharing three or more atoms. Examples of spiro carbocyclyl include, but are not limited to, spiro[5.5]undecane, spiro-pentadiene, spiro[3.6]-decan, and the like. Examples of fused carbocyclyl include, but are not limited to, naphthalene, benzopyrene, anthracene, acenaphthene, fluorene, nene and the like. Examples of bridged carbocyclyl include, but are not limited to, bicyclo[1,1,1]pentenyl, bicyclo[2,2,1]heptenyl,bicyclo[2.2.1]heptane, bicyclo[2.2.2]octane, bicyclo[3.3.1]nonane, bicyclo[3.3.3]undecane, and the like.

As used herein, the term "heterocyclyl" refers to a carbocyclyl group wherein one or more (e.g. 1, 2 or 3) ring atoms are replaced by heteroatoms which include, but are not limited to, oxygen, sulfur, nitrogen, phosphorus, and the like. In some embodiments, the heterocyclyl is a saturated heterocyclyl. In some embodiments, the heterocyclyl is an unsaturated heterocyclyl having one or more double bonds in its ring system. In some embodiments, an unsaturated heterocyclyl group may contain one or more aromatic rings.

Heterocyclyl groups can include mono- or poly-cyclic ring(s) (e.g., having 2, 3 or 4 fused, bridged or spiro rings). Exemplary monocyclic heterocyclyl groups include, but are not limited to, piperidyl, pyrrolidyl, tetrahydrofuran, piperidyl, piperazinyl, morpholinyl, and the like. Examples of spiro heterocyclyl include, but are not limited to, spiropyrans, spirooxazines, and the like. Examples of fused heterocyclyl include, but are not limited to, quinoline, isoquinoline, quinolizine, quinazoline, pteridine, chromene, isochromene, indole, isoindole, indolizine, indazole, purine, benzofuran, isobenzofuran, benzimidazole, benzothienyl, carbazole, phenazine, phenothiazine, phenanthridine groups, and the like. Examples of bridged heterocyclyl include, but are not limited to, morphan, hexamethylenetetramine, 8-aza-bicyclo[3.2.1]octane, 1-aza-bicyclo[2.2.2]octane, 1,4-diazabicyclo[2.2.2]octane (DABCO), and the like.

As used herein, the term "i-j membered" refers to carbocyclyl or heterocyclyl groups having i to j ring-forming atoms. For example, "3-8 membered carbocyclyl" refers to carbocyclyl groups having 3 to 10 (e.g., 3, 4, 5, 6, 7, 8, 9 or 10) ring-forming members; "3-10 membered heterocyclyl" refers to heterocyclyl having 3 to 10 (e.g., 3, 4, 5, 6, 7, 8, 9 or 10) ring-forming members. In some embodiments, carbocyclyl or heterocyclyl groups are 3-10 membered, 3-8 membered, 3-6 membered, or 4-6 membered. For example, piperidinyl is an example of a 6 membered heterocyclyl, pyrazolyl is an example of a 5 membered heterocyclyl, pyridyl is an example of a 6 membered heterocyclyl, and 1,2,3,4-tetrahydro-naphthalene is an example of a 10 membered carbocyclyl.

As used herein, the term "aromatic group" or "aromatic ring" refers to mono- or polycyclic carbocyclyl or heterocyclyl moiety having alternating double and single bonds between ring forming atoms in at least one ring. In some embodiments, the aromatic rings have 5 to 12, 5 to 10, 5 to 8, 6 to 12, 6 to 10, or 6 to 8 ring forming atoms (i.e., 5-12, 5-10, 5-8, 6-12, 6-10, or 6-8 membered). Examples of carbocyclic aromatic groups include, but are not limited to, phenyl, naphthyl, tetrahydronaphthyl, indanyl, idenyl and the like. In some embodiments, the heterocyclic aromatic group is 5 membered or 6 membered. Exemplary 5 membered heterocyclic aromatic groups are thienyl, furyl, pyrrolyl, imidazolyl, thiazolyl, oxazolyl, pyrazolyl, isothiazolyl, isoxazolyl, 1,2,3-triazolyl, 1,2,4-triazolyl, 1,3,4-triazolyl, tetrazolyl, 1,2,3-thiadiazolyl, 1,2,4-thiadiazolyl, 1,3,4-thiadiazolyl, 1,2,3-oxadiazolyl, 1,2,4-oxadiazolyl, 1,3,4-oxadiazolyl and the like. Exemplary 6 membered heterocyclic aromatic groups are pyridyl, pyrazinyl, pyrimidinyl, triazinyl and pyridazinyl.

The "compound" of present disclosure is intended to encompass all stereoisomers, geometric isomers, and tautomers of the structures depicted unless otherwise specified.

The term "stereoisomer" refers to any of the various stereoisomeric configurations (e.g., enantiomers, diastereomers and racemates) of an asymmetric compound (e.g., those having one or more asymmetrically substituted carbon atoms-"asymmetric centers"). Compounds of the present disclosure that contain asymmetric centers can be isolated in optically active (enantiomers or diastereomers) or optically inactive (racemic) forms. The term "enantiomer" includes pairs of stereoisomers that are non-superimposable mirror images of each other. A 1:1 mixture of a pair of enantiomers is a "racemic mixture". The terms "diastereomers" or "diastereoisomers" include stereoisomers that have at least two asymmetric atoms, but which are not mirror images of each other. Certain compounds containing one or more asymmetric centers may give rise to enantiomers, diastereomers or other stereoisomeric forms that may be defined, in terms of absolute configuration, as (R)- or (S)- at each asymmetric center according to the Cahn-Ingold-Prelog R—S system. Resolved compounds whose absolute configuration is unknown can be designated using the term "or" at the asymmetric center. Methods on how to prepare optically active forms from racemic mixtures are known in the art, such as resolution by HPLC or stereoselective synthesis.

The "geometric isomers" or "cis and trans isomers" refer to compounds with same formula but their functional groups are rotated into a different orientation in three-dimensional space. The term "tautomers" include prototropic tautomers that are isomeric protonation states of compounds having the same formula and total charge. Examples of prototropic tautomers include, but are not limited to, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H- 1,2,4-triazole, 1H- and 2H- isoindole, and 1H- and 2H-pyrazole. Tautomers can be in equilibrium or sterically locked into one form by appropriate substitution. Compounds of the present disclosure identified by name or structure as one particular tautomeric form are intended to include other tautomeric forms unless otherwise specified.

The "compound" of the present disclosure is also intended to encompass all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the "compound" of present disclosure are meant to also include their isotopes such as but are not limited to: $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, 81Br, $^{127}I$ and $^{131}I$. In some embodiments, hydrogen includes protium, deuterium and tritium. In some embodiments, the term "substituted by deuterium" or "deuterium substititued" to replace the other isoform of hydrogen (e.g., protium) in the chemical group with deuterium. In some embodiments, carbon includes $^{12}C$ and $^{13}C$.

It is also to be understood that the "compound" of present disclosure can exist in solvated as well as unsolvated forms, such as, for example, hydrated forms, solid forms, and the present disclosure is intended to encompass all such solvated and unsolvated forms.

It is further to be understood that the "compound" of present disclosure can exist in forms of pharmaceutically acceptable salts or esters.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopeia (such as U.S. Pharmacopeia, China Pharmacopeia or European Pharmacopeia) for use in animals, and more particularly in humans.

As used herein, "pharmaceutically acceptable salts" refers to derivatives of the compounds of present disclosure wherein the parent compound is modified by converting an existing acidic moiety (e.g., carboxyl and the like) or base moiety (e.g., amine, alkali and the like) to its salt form. In many cases, compounds of present disclosure are capable of forming acid and/or base salts by virtue of the presence of amino and/or carboxyl groups or groups similar thereto. And the pharmaceutically acceptable salts are acid and/or base salts that retain biological effectiveness and properties of the parent compound, which typically are not biologically or otherwise undesirable. Suitable pharmaceutically acceptable salts of a compound of the present disclosure includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenyl acetic, benzoic, mandelic, methanesulfonic, napadisylic, ethanesulfonic, toluenesulfonic, trifluoroacetic, salicylic, sulfosalicylic acids and the like). In some embodiments, the pharmaceutically acceptable salt of the compound of the present disclosure is a formic acid salt. In some embodiments, the pharmaceutically acceptable salt of the compound of the present disclosure is a TFA salt.

Suitable pharmaceutically acceptable salts of a compound of the present disclosure also includes, for example, an base-addition salt, which can be derived from for example an inorganic bases (for example, sodium, potassium, ammonium salts and hydroxide, carbonate, bicarbonate salts of metals from columns Ito XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine, and tromethamine. The skilled person would appreciate that adding acids or bases for forming acid/base-addition salts other than those shown in the examples may also be possible. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

As used herein, "pharmaceutically acceptable esters" refers to esters which hydrolyze in vivo and include those that break down readily in the human body to leave the parent compound or a salt thereof. Such esters can act as a prodrug as defined herein. The esters can be formed with an amine, hydroxyl, or carboxyl side chain on the compounds described herein. For example, if a disclosed compound contains an alcohol functional group, an ester can be formed by the replacement of the hydrogen atom of the alcohol group with an acidic group such as, including, but not limited to, carboxylic acids, phosphoric acids, phosphinic acids, sulfinic acids, sulfonic acids and boronic acids groups. The procedures and specific groups to make such esters are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

The present disclosure also includes active intermediates, active metabolites and prodrugs of the compounds of present disclosure. As used herein, an "active intermediate" refer to intermediate compound in the systhetic process, which exhibits the same or essentially the same biological activity as the final synthesized compound.

As used herein, an "active metabolite" refers to a breakdown or end product of a compound of the present disclosure or its salt or prodrug produced through metabolism or biotransformation in the animal or human body, which exhibits the same or essentially the same biological activity as the specified compound. Such metabolites may result from, for example, oxidation, reduction, hydrolysis, amidation, deamidation, esterification, deesterification, enzymatic cleavage, and the like, of the administered compound or salt or prodrug.

As used herein, "prodrugs" refer to any compounds or conjugates which release the active parent drug when administered to an animal or human subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl group is bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the present disclosure. Preparation and use of prodrugs is discussed in T. Higuchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Unless otherwise specified, "Wild-Type ErbB" refers to normal ErbB family members existing in the natural environment that performs the normal function of ErbB. In one aspect, the present disclosure provides inhibitory compounds of ErbB family kinase (e.g., EGFR, HER2, Her3 and/or Her4). In some embodiment, the compounds of the present disclosure can inhibit more than one ErbB family kinases. In some other embodiments, the compounds of the present disclosure selectively inhibit ErbB2 (i.e. HER2), while do not inhibit other ErbB family kinases (e.g. EGFR).

In some embodiments, the compounds of the present disclosure can inhibit both Wild-Type (WT) and mutant forms of ErbB family kinase. As used herein, the term "mutations" refers to any mutations to the ErbB protein; "mutant" or "mutated form" refers to the protein that contains said mutation. Exemplary mutations of ErbBs, include but are not limited to, L858R, T790M, G719S, G719X, delE746-A750, A763 Y764insFQEA, V769 D770insASV, H773 V774insNPH and the like in EGFR, and Exon 20 insYVMA in HER2. In some embodiments, the compounds of the present disclosure can inhibit both wild-type (WT) HER2 and mutant forms of HER2 (e.g., Exon 20 insYVMA).

In some embodiments, compounds of the present disclosure inhibit phosphorylation of WT HER2 with an $IC_{50}$ value of 0.1-200 nM, prefereably 0.1-150 nM, 0.1-130 nM, 0.1-120 nM, 0.1-100 nM, 0.1-50 nM, 0.1-40 nM, 0.1-30 nM, 0.1-25 nM, 0.1-20 nM, 0.1-10 nM, 0.5-200 nM, 0.5-150 nM, 0.5-130 nM, 0.5-120 nM, 0.5-100 nM, 0.5-50 nM, 0.5-40 nM, 0.5-30 nM, 0.5-25 nM, 0.5-20 nM, 0.5-10 nM, 1-200 nM, 1-150 nM, 1-130 nM, 1-120 nM, 1-100 nM, 1-50 nM, 1-40 nM, 1-30 nM, 1-25 nM, 1-20 nM, 1-10 nM, 2-200 nM, 2-150 nM, 2-130 nM, 2-120 nM, 2-100 nM, 2-50 nM, 2-40 nM, 2-30 nM, 2-25 nM, 2-20 nM, or 2-10 nM, more preferably 0.1-150 nM, 0.1-130 nM, 1-150 nM, 1-130 nM, 2-130 nM, or 2-150 nM.

The proliferation inhibition effect can be represented by "50% growth inhibition concentration" ($GI_{50}$) value, which refers to the concentration of a compound where 50% of its maximal proliferation inhibition effect is observed. The $GI_{50}$ value can be measured by methods known in the art, for example, MTS, Casein and any other methods. In some embodiments, compounds of the present disclosure inhibit proliferation of WT HER2 and/or mutant HER2 bearing cells with an $GI_{50}$ value of 0.1-200 nM, prefereably 0.1-150 nM, 0.1-130 nM, 0.1-120 nM, 0.1-100 nM, 0.1-50 nM, 0.1-40 nM, 0.1-30 nM, 0.1-20 nM, 0.1-10 nM, 1-200 nM, 1-150 nM, 1-130 nM, 1-120 nM, 1-100 nM, 1-50 nM, 1-40 nM, 1-30 nM, 1-20 nM, 1-10 nM, 2-200 nM, 2-150 nM, 2-130 nM, 2-120 nM, 2-100 nM, 2-50 nM, 2-40 nM, 2-30 nM, 2-25 nM, 2-20 nM, or 2-10 nM, 4-200 nM, 4-150 nM, 4-130 nM, 4-120 nM, 4-50 nM, 4-40 nM, 4-30 nM, 4-20 nM, 4-10 nM, more preferably 0.1-150 nM, 0.1-130 nM, 1-150 nM, 1-130 nM, 2-150 nM, 2-130 nM, 4-150 nM, or 4-130 nM as measured by MTS.

As used herein, "selectively inhibit" HER2, means that a provided compound is at least 1000 times more potent, at least 500 times, at least 200 times, at least 100 times, at least 50 times, at least 45 times, at least 40 times, at least 35 times, at least 30 times, at least 25 times, at least 20 times, at least 15 times, or at least 10 times more potent as an inhibitor of WT (and/or mutant form of) HER2 as compared to other type of ErbB kinase (e.g., EGFR). In some embodiments, "selectively inhibit" HER2, means that a provided compound is up to 1500 times more potent, up to 1200 times, up to 1000 times, up to 800 times, up to 600 times, up to 400 times, up to 200 times, up to 100 times, up to 50 times, more potent as an inhibitor of HER2 (WT and/or mutant form), as compared to other type of ErbB kinase (e.g., EGFR).

In some embodiments, the term "do not inhibit" other type of ErbB kinase (e.g., EGFR) means that a provided compound inhibits other type of ErbB kinase (e.g., WT EGFR) with an $IC_{50}$ of at least 500 nM. In some embodiments, such compound inhibits other type of ErbB kinase with an $IC_{50}$ of at least 10 µM, at least 9 µM, at least 8 µM, at least 7 µM, at least 6 µM, at least 5 µM, at least 3 µM, at least 2 µM, or at least 1 µM.

In some embodiments, the $IC_{50}$ and/or $GI_{50}$ of the compounds to WT-EGFR is at least 5 times, 10 times, 20 times, 50 times, 100 times, 200 times, 500 times, 1000 times, preferably 50 times, 100 times, 200 times, 500 times, or 1000 times higher than the $IC_{50}$ and/or $GI_{50}$ of the compounds to WT HER2.

The compounds or a pharmaceutically acceptable salt, ester, hydrate, solvate or stereoisomer thereof when compared with other clinically available ErbB inhibitors, exhibit certain improved properties e.g. higher blood-brain-barrier BBB penetration (thus making them potentially useful for the treatment of cancers that have metastasized to the central nervous system (CNS), in particular brain metastases and leptomeningeal metastases); show better selectivity against certain type of ErbB (e.g. HER2) whilst maintaining equivalent or improved inhibitory activity as compared to existing drugs for said certain type of ErbB. Therefore, such compounds, or a pharmaceutically acceptable salt, ester, hydrate, solvate or stereoisomer thereof, may be especially useful in the treatment of disease states in which these HER2 are implicated, for example in the treatment of cancer, especially cancer with CNS (in particular, brain and leptomeningeal) metastases.

Synthetic Method

Synthesis of the compounds provided herein, including salts, esters, hydrates, or solvates or stereoisomers thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

Abbreviations as used herein, are defined as follows: "1×" or "×1" for once, "2×" or "×2" for twice, "3×" or "×3" for thrice, "4×" or "×4" for four times, "5×" or "×5" for five times, "° C." for degrees Celsius, "eq" or "eq." for equivalent or equivalents, "g" for gram or grams, "mg" for milligram or milligrams, "L" for liter or liters, "mL" or "ml" for milliliter or milliliters, "µL" for microliter or microliters, "Nor" for normal, "M" for molar, "mmol" for millimole or millimoles, "min" for minute or minutes, "h" or "hr" for hour or hours, "r.t." or "rt" for room temperature, "atm" for atmosphere, "psi" for pounds per square inch, "conc." for concentrate, "sat" or "sat'd" for saturated, "MS" or "Mass Spec" for mass spectrometry, "ESI" for electrospray ionization mass spectroscopy, "LCMS" for liquid chromatography mass spectrometry, "HPLC" for high pressure liquid chromatography, "RP" for reverse phase, "TLC" or "tlc" for thin layer chromatography, "SM" for starting material, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, and "Hz" for hertz. "α", "β", "R", "S", "E", and "Z" are stereochemical designations familiar to one skilled in the art.

Abbreviations for chemicals used in the synthesis of the compounds provided herein are listed below:

| | |
|---|---|
| AcOH or HOAc | acetic acid |
| MeOH | Methanol |
| EtOH | Ethanol |
| t-BuOH | tert-butyl alcohol |
| t-BuOK | Potassium tert-butoxide |
| EtOAc or EA | ethyl acetate |
| Fe | Iron |
| FA | Formic acid |
| $NH_2Boc$ | tert-butyl carbamate |
| Boc | tert-butyloxycarbonyl |
| $BH_3 \cdot Me_2S$ or $BH_3 \cdot DMS$ | borane dimethyl sulfide complex |
| $CDCl_3$ | deuterated chloroform |
| $CH_2Cl_2$ | Dichloromethane |
| $CH_3CH_2I$ | ethyl iodide |
| $CH_3CN$ or MeCN | Acetonitrile |
| $Cs_2CO_3$ | cesium carbonate |
| CuI | copper iodide |
| DCM | Dichloromethane |
| DEA | Diethylamine |
| DEAD | diethyl azodicarboxylate |
| DIAD | diisopropyl azodicarboxylate |
| DIEA or DIPEA | N,N,-diisopropylethylamine |
| DMF | dimethyl formamide |
| DMSO | dimethyl sulfoxide |
| EDC (or EDC·HCl) or EDCI (or EDCI·HCl) or EDAC | 3-ethyl-3'-(dimethylamino)propyl-carbodiimide hydrochloride or 1-(3-dimethylaminopropyl)-3-ethylcarbodiimide hydrochloride |
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| Hex | Hexane |
| HOBt or HOBT | 1-hydroxybenzotriazole monohydrate |
| LiOH | lithium hydroxide |

-continued

| | |
|---|---|
| mCPBA or m-CPBA | meta-chloroperbenzoic acid |
| Pd/C | palladium on carbon |
| PE | petroleum ether |
| $SOCl_2$ | thionyl chloride |
| TEA or $Et_3N$ | Triethylamine |
| TFA | trifluoroacetic acid |
| THF | Tetrahydrofuran |
| $BH_3$-THF | Borane tetrahydrofuran |
| TBAF | tetrabutylammonium fluoride |
| TRIS | tris(hydroxymethyl)aminomethane |
| $K_3PO_4$ | potassium phosphate |
| $K_2CO_3$ | potassium carbonate |
| KI | potassium iodide |
| KOH | potassium hydroxide |
| $MgSO_4$ | magnesium sulfate |
| NaCl | sodium chloride |
| AcONa or NaOAc | sodium acetate |
| MeONa | sodium methoxide |
| $NaClO_2$ | sodium chlorite |
| $NaH_2PO_4$ | Sodium dihydrogen phosphate |
| $NaHCO_3$ | sodium bicarbonate |
| $NaIO_4$ | sodium periodate |
| NaOH | sodium hydroxide |
| $Na_2SO_3$ | sodium sulfite |
| $Na_2SO_4$ | sodium sulfate |
| $NH_4Cl$ | ammonium chloride |
| NMO | N-methylmorpholine-N-oxide |
| $OsO_4$ | Osmium tetroxide |
| $PBr_3$ | phosphorus tribromide |
| $P(OEt)_3$ | triethyl phosphate |
| $PCl_5$ | phosphorus pentachloride |
| $POCl_3$ | phosphorus oxychloride |
| $Pd(dppf)Cl_2$ or $PdCl_2(dppf)$ | [1,1'-Bis(diphenylphosphino)ferrocene]dichloropalladium (II) |
| $Pd_2(dba)_3$ | tris(dibenzylideneacetone)dipalladium(0) |
| $PPh_3$ | Triphenylphosphine |
| $Pd(PPh_3)_4$ | tetrakis(triphenylphosphine) palladium (0) |
| Xantphos | 4,5-bis(diphenylphosphino)-9,9-dimethylxanthene |
| $N_2H_4 \cdot H_2O$ | hydrazine monohydrate |
| MTBE | methyl tert-butyl ether |
| $NH_2NH_2$ | hydrazine |

Pharmaceutical Composition

The present disclosure provides pharmaceutical compositions comprising at least one compound of the present disclosure. In some embodiments, the pharmaceutical composition comprises more than one compound of the present disclosure. In some embodiments, the pharmaceutical composition comprises one or more compounds of the present disclosure, and a pharmaceutical acceptable carrier.

The pharmaceutically acceptable carriers are conventional medicinal carriers in the art which can be prepared in a manner well known in the pharmaceutical art. In some embodiments, the compounds of the present disclosure may be admixed with pharmaceutically acceptable carrier for the preparation of pharmaceutical composition.

The term "pharmaceutically acceptable carrier" as used herein refers to a pharmaceutically acceptable material, composition or vehicle, such as a liquid or solid filler, diluent, excipient, solvent or encapsulating material, involved in carrying or transporting a compound provided herein from one location, body fluid, tissue, organ (interior or exterior), or portion of the body, to another location, body fluid, tissue, organ, or portion of the body. Pharmaceutically acceptable carriers can be vehicles, diluents, excipients, or other materials that can be used to contact the tissues of an animal without excessive toxicity or adverse effects. Exemplary pharmaceutically acceptable carriers include, sugars, starch, celluloses, malt, tragacanth, gelatin, Ringer's solution, alginic acid, isotonic saline, buffering agents, and the like. Pharmaceutically acceptable carrier that can be employed in present disclosure includes those generally known in the art, such as those disclosed in "Remington Pharmaceutical Sciences" Mack Pub. Co., New Jersey (1991), which is incorporated herein by reference.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The form of pharmaceutical compositions depends on a number of criteria, including, but not limited to, route of administration, extent of disease, or dose to be administered.

The pharmaceutical compositions can be formulated for oral, nasal, rectal, percutaneous, intravenous, or intramuscular administration. In accordance to the desired route of administration, the pharmaceutical compositions can be formulated in the form of tablets, capsule, pill, dragee, powder, granule, sachets, cachets, lozenges, suspensions, emulsions, solutions, syrups, aerosols (as a solid or in a liquid medium), spray, ornmentment, paste, cream, lotion, gel, patche, inhalant, or suppository.

The pharmaceutical compositions can be formulated to provide quick, sustained or delayed release of the active ingredient after administration to the patient by employing procedures known in the art. In some embodiments, the pharmaceutical composition is formulated in a sustained released form. As used herein, the term "sustained released form" refers to release of the active agent from the pharmaceutical composition so that it becomes available for bio-absorption in the subject, primarily in the gastrointestinal tract of the subject, over a prolonged period of time (extended release), or at a certain location (controlled release). In some embodiments, the prolonged period of time can be about 1 hour to 24 hours, 2 hours to 12 hours, 3 hours to 8 hours, 4 hours to 6 hours, 1 to 2 days or more. In certain embodiments, the prolonged period of time is at least about 4 hours, at least about 8 hours, at least about 12 hours, or at least about 24 hours. The pharmaceutical composition can be formulated in the form of tablet. For example, release rate of the active agent can not only be controlled by dissolution of the active agent in gastrointestinal fluid and subsequent diffusion out of the tablet or pills independent of pH, but can also be influenced by physical processes of disintegration and erosion of the tablet. In some embodiments, polymeric materials as disclosed in "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, N.Y. (1984); Ranger and Peppas, 1983, J Macromol. Sci. Rev. Macromol Chem. 23:61; see also Levy et al., 1985, Science 228:190; During et al., 1989, Ann. Neurol. 25:351; Howard et al., 1989, J. Neurosurg. 71:105 can be used for sustained release. The above references are incorporated herein by reference in their entirety.

In certain embodiments, the pharmaceutical compositions comprise about 0.0001 mg to about 5000 mg of the compounds of the present disclosure (e.g. about 0.0001 mg to about 10 mg, about 0.001 mg to about 10 mg, about 0.01 mg to about 10 mg, about 0.1 mg to about 10 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg, about 50 mg to about 200 mg, about 50 mg to about 300 mg, about 50 mg to about 400 mg, about 50 mg to about 500 mg, about 100 mg to about 200 mg, about 100 mg to about 300 mg, about 100 mg to about 400 mg, about 100 mg to about 500 mg, about 200 mg to about 500 mg, about 300 mg to about 500 mg, about 400 mg to about 500 mg, about 500 mg to about 1000 mg, about 600 mg to about 1000 mg, about 700 mg to about 1000 mg, about 800 mg to about 1000 mg, about 900 mg to about 1000 mg, about 1000 mg to about 2000 mg, about 2000 mg to about 3000 mg, about 3000 mg to about 4000 mg, or about 4000 mg to about 5000 mg). Suitable dosages per subject per day can be from about 5 mg to about 500 mg, prefereably about 5 mg to about 50 mg, about 50 mg to about 100 mg, or about 50 mg to about 500 mg.

In certain embodiments, the pharmaceutical compositions can be formulated in a unit dosage form, each dosage containing from about 0.0001 mg to about 10 mg, about 0.001 mg to about 10 mg, about 0.01 mg to about 10 mg, about 0.1 mg to about 10 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg, about 50 mg to about 200 mg, about 50 mg to about 300 mg, about 50 mg to about 400 mg, about 50 mg to about 500 mg, about 100 mg to about 200 mg, about 100 mg to about 300 mg, about 100 mg to about 400 mg, about 100 mg to about 500 mg, about 200 mg to about 500 mg, about 300 mg to about 500 mg, about 400 mg to about 500 mg, about 500 mg to about 1000 mg, about 600 mg to about 1000 mg, about 700 mg to about 1000 mg, about 800 mg to about 1000 mg, about 900 mg to about 1000 mg, about 1000 mg to about 2000 mg, about 2000 mg to about 3000 mg, about 3000 mg to about 4000 mg, or about 4000 mg to about 5000 mg of the compounds of the present disclosure.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical carrier. In some embodiments, the pharmaceutical compositions comprise one or more compounds of the present disclosure as a first active ingredient, and further comprise a second active ingredient. The second active ingredient can be any anticancer agent known in the art, for examples, chemotherapeutics, cell signal transduction inhibitors, cell signal transduction inhibitors, alkylating agents, topoisomerase inhibitors, immunotherapeutic agents, mitosis inhibitors, antihormonal agents, chemotherapy drugs, EGFR inhibitors, CTLA-4 inhibitors, MEK inhibitors, PD-L1 inhibitors; OX40 agonists, and the like. Representative examples of the anticancer agents for treating cancers or tumors may include, but are not limited to, trasutzumab, trastuzumab emantasine, pertuzumab, ONT380, neratinib, lapatinib, sorafenib, sunitinib, dasatinib, vorinostat, temsirolimus, everolimus, pazopanib, trastuzumab, ado-trastuzumab emtansine, pertuzumab, bevacizumab, cetuximab, ranibizumab, pegaptanib, panitumumab, tremelimumab, pembrolizumab, nivolumab, ipilimumab, atezolizumab, avelumab, durvalumab, crizotinib, ruxolitinib, capecitabine, docetaxel, vinorelbine, paclitaxel, vincristine, vinblastine, cisplatin, carboplatin, gemcitabine, tamoxifen, raloxifene, cyclophosphamide, chromabucil, carmustine, methotrexate, fluorouracil, actinomycin, doxorubicin, epirubicin, anthracycline, bleomycin, mitomycin-C, irinotecan, topotecan, teniposide interleukin, interferon, and the like. In some embodiments, the second active agent is one or more of chemotherapeutics (capecitabine, docetaxel, vinorelbine), or a HER2 targeted antibody (trasutzumab, trastuzumab emantasine, pertuzumab).

Method for Treatment

The present disclosure provides a method of treating diseases associated with ErbB (including, for example, HER2), comprising administering to a subject an therapeutically effective amount of one or more compounds, pharmaceutically acceptable salts, esters, hydrates, solvates or stereoisomers thereof or the pharmaceutical composition of the present disclosure.

As used herein, the term "diseases associated with ErbB" refers to diseases whose onset or development or both are associated with the genomic alterations, expression, overexpression or activity of ErbB. Examples include but are not limited to, immune-related diseases, proliferative disorders, cancer, and other diseases.

As used herein, the term "disease associated with HER2" refers to a disease or disorder whose onset or development or both is associated with the genomic alterations, expression, over-expression or activity of HER2, as the case may be. Examples include but are not limited to, immune-related diseases, proliferative disorders, cancer, and other diseases.

In some embodiments, the disease associated with ErbB is cancer, preferably an ErbB-expressing cancer, or ErbB-overexpressing cancer. An "ErbB-expressing cancer" is one that involves cancer cells or tumor cells having ErbB protein, such as HER2, present at their cell surface. An "ErbB-overexpressing cancer" is one which has significantly higher levels of ErbB protein, such as HER2, at the cell surface of a cancer or tumor cell, compared to a noncancerous cell of the same tissue type. Such overexpression may be caused by gene amplification or by increased transcription or translation. ErbB receptor expression or overexpression may be determined in a diagnostic or prognostic assay by evaluating increased levels of the ErbB protein present on the surface of a cell (e.g. via an immunohistochemistry assay; IHC). Alternatively, or additionally, one may measure levels of ErbB-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR). Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

In particular, the cancers include but are not limited to, leukemia, glioblastoma, melanoma, chondrosarcoma, cholangiocarcinoma, osteosarcoma, lymphoma, lung cancer, adenoma, myeloma, hepatocellular carcinoma, adrenocortical carcinoma, pancreatic cancer, breast cancer, bladder cancer, prostate cancer, liver cancer, gastric cancer, colon cancer, colorectal cancer, ovarian cancer, cervical cancer, brain cancer, esophageal cancer, bone cancer, testicular cancer, skin cancer, kidney cancer, mesothelioma, neuroblastoma, thyroid cancer, head and neck cancer, esophageal cancer, eye cancer, prostate cancer, nasopharyngeal cancer, or oral cancer. In some embodiments, the cancers are lung cancer, breast cancer, ovarian cancer, bladder cancer, or glioblastoma. In some embodiments, the cancer is breast cancer, gastric cancer, colorectal cancer, pancreatic cancer, prostate cancer, bladder cancer, ovarian cancer, or lung cancer (e.g. non-small cell lung cancer, small cell lung cancer, adenocarcinoma, squamous cell lung cancer and large cell lung cancer). In some embodiments, the diseases associated with ErbB (e.g., HER2) is cancer that has metastasised to the central nervous system (CNS), particularly the cancer with brain and leptomengingeal metastasis.

As used herein, the terms "treatment" and "treat" refer to reversing, alleviating, delaying the onset of, or inhibiting the progress of a disease or disorder, or one or more symptoms thereof, as described herein. In some embodiments, treatment may be conducted after one or more symptoms have developed. In other embodiments, treatment may be conducted in the absence of symptoms. For example, treatment may be conducted to a susceptible individual prior to the onset of symptoms (e.g., in light of a history of symptoms and/or in light of genetic or other susceptibility factors). Treatment may also be continued after symptoms have resolved, for example to present or delay their recurrence.

The therapeutically effective amount of a compound as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g. physician or veterinarian) as indicated by these and other circumstances or requirements.

As used herein, the terms "subject" and "individual" are used interchangeably and refer to a warm-blooded animal, including human or any non-human animal (e.g. mouse, rat, rabbit, dog, cat, cattle, swine, sheep, horse or primate). A human includes pre and post-natal forms. In some embodiments, a subject is a human being. A subject can be those suspected to be afflicted with a disease associated with ErbB (preferably HER2) but may or may not display symptoms of the disease.

In some embodiments, the one or more compounds, pharmaceutically acceptable salts, esters, hydrates, solvates or stereoisomers thereof or the pharmaceutical composition provided herein is administered via a parenteral route or a non-parenteral route. In some embodiments, the one or more compounds pharmaceutically acceptable salts, hydrates, solvates or stereoisomers thereof or the pharmaceutical composition is administered orally, enterally, buccally, nasally, intranasally, transmucosally, epidermally, transdermally, dermally, ophthalmically, pulmonary, sublingually, rectally, vaginally, topically, subcutaneously, intravenously, intramuscularly, intraarterially, intrathecally, intracapsularly, intraorbitally, intracardiacally, intradermally, intraperitoneally, transtracheally, subcuticularly, intra-articularly, subcapsularly, subarachnoidly, intraspinally, or intrasternally.

The compounds provided herein can be administered in pure form, in a combination with other active ingredients or in the form of pharmaceutically compositions of the present disclosure. In some embodiments, the compounds provided herein can be administered to a subject in need concurrently or sequentially in a combination with one or more anticancer agent(s) known in the art. In some embodiments, the administration is conducted once a day, twice a day, three times a day, or once every two days, once every three days, once every four days, once every five days, once every six days, once a week.

In some embodiments, the one or more compounds, pharmaceutically acceptable salts, esters, hydrates, solvates or stereoisomers thereof or the pharmaceutical composition provided herein is administered orally. For oral administration, any dose is appropriate that achieves the desired goals. In some embodiments, suitable daily dosages are between about 0.001-5000 mg, preferably between 0.1 mg and 5 g, more preferably between 5 mg and 1 g, more preferably between 10 mg and 500 mg, and the administration is conducted once a day, twice a day, three times a day, every day, or 3-5 days a week. In some embodiments, the dose of the one or more compounds, pharmaceutically acceptable salts, esters, hydrates, solvates or stereoisomers thereof or the pharmaceutical composition provided herein ranges between about 0.0001 mg, preferably, 0.001 mg, 0.01 mg, 0.1 mg, lmg, 10 mg, 50 mg, 100 mg, 200 mg, 250 mg, 500 mg, 750 mg, 1000 mg, 2000 mg, 3000 mg, 4000 mg or up to about 5000 mg per day. In some embodiments, the one or more compounds, pharmaceutically acceptable salts, esters, hydrates, solvates or stereoisomers thereof or the pharmaceutical composition provided herein after being administered to the subject, can cross blood-brain barrier (BBB) of the subject.

Use of Compounds

In certain embodiments, the present disclosure provides use of the compounds, pharmaceutically acceptable salts, esters, hydrates, solvates or stereoisomers thereof, or pharmaceutical composition of the present disclosure in the manufacture of medicaments for treating diseases associated with ErbB (e.g. HER2).

The compounds and pharmaceutical compositions thereof in the present disclosure can be used in inhibiting ErbB (expression or activity), especially inhibiting HER2 (expression or activity) both in vivo and in vitro. In some embodiments, the compounds and pharmaceutical compositions thereof in the present disclosure can be used in inhibiting ErbB (expression or activity), especially inhibiting HER2 (expression or activity) in a non-diagnostic, non-treatment methods (for example, for research purpose).

The compounds and pharmaceutical compositions thereof in the present disclosure can be used in the prevention or treatment of the onset or development of any of the diseases associated with ErbB (e.g., HER2) in warm blooded animals especially in human.

In such situation, the present disclosure also provides a method of screening patient suitable for treatment with the compounds or pharmaceutical composition of the present disclosure alone or combined with other ingredients (e.g. a second active ingredient, e.g. anticancer agent). The method includes sequencing the tumor samples from patients and detecting the accumulation of ErbB (e.g. HER2) in the patient.

EXAMPLES

The followings further explain the general methods of the present disclosure. The compounds of the present disclosure may be prepared by the methods known in the art. The following illustrates the detailed preparation methods of the preferred compounds of the present disclosure. However, they are by no means limiting the preparation methods of the compounds of the present disclosure.

Synthetic Examples

The structures of the compounds in the following examples were characterized by nuclear magnetic resonance (NMR) or/and mass spectrometry (MS). NMR shift (δ) was given in the unit of $10^{-6}$ (ppm). $^1$H-NMR spectra was recorded in dimethyl sulfoxide-$d_6$ (DMSO-$d_6$) or CDCl$_3$ or CD$_3$OD or D$_2$O (from Aldrich or Cambridge Isotope Lab., Inc.) on Bruker AVANCE NMR (400 MHz) spectrometers using ICON-NMR (under TopSpin program control), or Varian 400MR NMR or Varian VNMR400 NMR (400 MHz) spectrometers (under VnmrJ program control) with tetramethylsilane as an internal standard.

MS measurement was carried out using Shimadzu 2010 Mass Spectrometer or Agilent 6110A MSD or 1969A TOF mass spectrometer using electrospray, chemical and electron impact ionization methods from a range of instruments.

High Performance Liquid Chromatography (HPLC) measurement was carried out on Shimadzu LC-20A systems or Shimadzu LC-2010HT series, or Agilent 1200 LC or Agilent 1100 series using Ultimate XB-C18 column (3.0*50 mm, 3 um or 3.0*150 mm, 3 um), or Xbridge shieldRP18 column (5 um, 50 mm*2.1 mm), or Xtimate C18 column (3 um, 2.1*30 mm), or MERCK RP18 2.5-2 mm, or Agilent Zorbax Eclipse Plus C18 column (4.6 mm*150 mm, 5 μm) etc.

Thin layer chromatography was carried out using Yantai Huanghai HSGF254 silica gel or Anhui Liang Chen Gui Yuan plates. The silica gel plates used for thin layer chromatography (TLC) were 0.15 mm-0.2 mm. The silica gel plates used for separating and purifying products by TLC were 0.4 mm-0.5 mm.

Purified chromatographic column uses the silica gel as the carrier (100~200, 200~300 or 300~400 mesh, producted by Yantai Huanghai co., or Anhui Liang Chen Gui Yuan co., etc.), or flash column (silica-CS flash column 40-60 um, or reversed phase C18 column 20-35 um, produced by Agela Technologies, etc.) or flash column silica-CS (40-60 um) or C18 column (20-40 um) by Agela Technologies in the Teledyne ISCO combi-flash or Biotage flash system. The size of columns were adjusted according to the amount of compounds.

The known starting materials of the present disclosure can be synthesized by using or according to the known methods in the art, or can be purchased from Alia Aesar, Langcaster, TCI, Aldrich, Bepharm, and Scochem (or PharmaBlock, Bide, Amatek, Stru Chem, Firster Pharmaceutical, Titan (Adamas) etc.).

Unless otherwise specified, the reactions in the examples were all carried out under argon or nitrogen atmosphere. Argon or nitrogen atmosphere refers to that the reaction flask is connected to an argon or nitrogen ballon with a volume of about 1 L. Hydrogenation was usually carried out under pressure. Unless otherwise specified, the reaction temperature in the examples was ambient temperature, which was 20° C.-30° C.

The reaction progress in the examples was monitored by TLC. The eluent systems used for the reactions include dichloromethane-methanol system and petroleum ether-ethyl acetate system. The volume ratios of the solvents were adjusted according to the different polarities of compounds.

The elution system of column chromatography used for purifying compounds and eluent system of TLC include dichloromethane-methanol system and petroleum ether-ethyl acetate system. The volume ratios of the solvents were adjusted according to the different polarities of compounds. A small amount of alkaline or acidic agents (0.1%-1%) such as formic acid, or acetic acid, or TFA, or ammonia can be added for adjustment.

Example 1

N-(4-([1,2,4]triazolo[1,5-a]pyridin-7-yloxy)-3-methylphenyl)-5-((3,3-difluoro-1-methylpiperidin-4-yl)oxy)quinazolin-4-amine

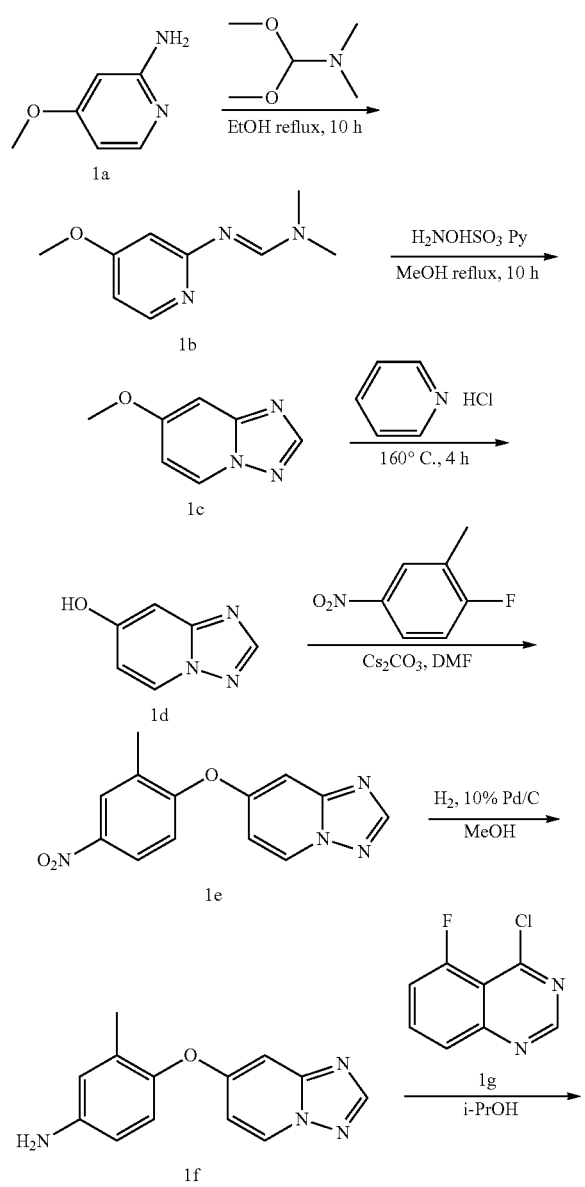

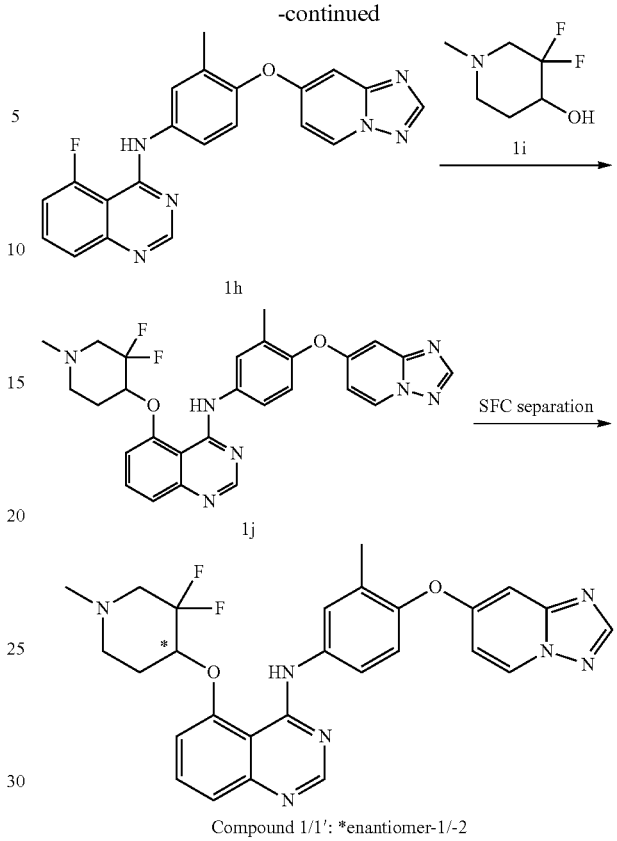

Compound 1/1': *enantiomer-1/-2

Procedure for the Preparation of Compound 1b:

To a solution of 4-methoxy-pyridin-2-ylamine (5.0 g, 40.3 mmol) in ethanol (150 mL) was added dimethoxymethyl-dimethyl-amine (4.8 g, 40.3 mmol). Then the mixture was stirred at reflux for 10 h. The mixture was concentrated to give crude product (7.8 g) which was not purified and used directly in the next step. LCMS: Rt=0.898 min in 0-60AB_220 & 254 1 cm chromatography (Xtimate C18, 2.1*30 mm, 3 um), MS (ESI) m/z=179.9 [M+H$^+$].

Procedure for the Preparation of Compound 1c:

To a solution of 1b (7.8g crude) in methanol was added hydroxylamine-o-sulfonic acid (5.42 g, 47.9 mmol), pyridine (7 g, 88.5 mmol) and the new resulting solution was stirred at reflux for 10h. The solution was concentrated and the residue was purified by silica gel (CH$_2$Cl$_2$MeOH, 100:1 to 50:1) to give product 1c (4.0 g, 61.5% yield) as a white solid. $^1$H NMR (400 MHz, DMSO-d$_6$) δ 8.76 (d, J=7.6 Hz, 1H), 8.32 (s, 1H), 7.22 (d, J=2.4 Hz, 1H), 6.84 (dd, J=7.6 Hz, 1H), 3.89 (s, 3H).

Procedure for the Preparation of Compound 1d:

A mixture of compound 1 c (900 mg, 6.03 mmol) and pyridine-hydrochloride (6 g, 51.9 mmol) in a flask was stirred at 160° C. for 4 h. The mixture was cooled down to 25° C. and the solution was neutralized by sodium hydroxide solution (1 M) to adjust the pH to 5-7. The resulting mixture was filtered to give product as a white solid. The filtrate was extracted with EtOAc (200 mL×5), the organic phase was combined, dried over sodium sulfate and concentrated under reduced pressure to give product as a white solid (700 mg, 85.9% yield). $^1$H NMR (400 MHz, DMSO-d$_6$) δ 10.87 (s, 1H), 8.70 (dd, J=7.4 Hz, 1H), 8.24 (s, 1H), 6.89 (dd, J=2.8 Hz, 1H), 6.75-72 (m, 1H).

Procedure for the Preparation of Compound 1e:

To a stirred solution of 1d (1.0 g, 7.4 mmol) and 1-fluoro-2-methyl-4-nitrobenzene (1.4 g, 8.9 mmol) in DMF (10 mL) was added $Cs_2CO_3$ (4.8 g, 14.8 mmol), the mixture was heated to 100° C. for 2 hours. The reaction mixture was concentrated under reduced pressure and the residue was dissolved in EtOAc (50 mL). The solution was washed with water and brine. The organic layer was concentrated and the residue was purified by column chromatography on silica gel (eluted with 5% to 20% ethyl acetate in petroleum ether) to give compound 1e (1.5 g, 75.0% yield) as a white solid.

Procedure for the Preparation of Compound 1f:

A solution of 1e (1.5 g, 5.6 mmol) and 10% Pd/C (150 mg) in methanol (15 mL) was heated at 45° C. for 3 hours under a hydrogen atmosphere (40 psi). The hot solution was filtered through Celite and the filtrate was concentrated under reduced pressure to provide compound 1f (1.2 g crude) as a pale gray solid which was used in the next step directly.

Procedure for the Preparation of Compound 1g:

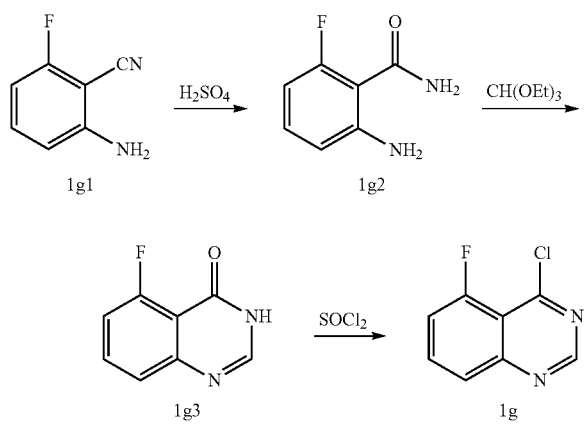

A stirred solution of compound 1g1 (100 g, 734.5 mmol) in concentrated $H_2SO_4$ (700 mL) was stirred at 65° C. for 3 hours. Then the mixture was poured into ice and adjust pH=9 by 20% NaOH aqueous solution. The mixture was extracted with EtOAc (1000 mL×3), the organic layers were combined and washed with brine, dried over $Na_2SO_4$ and then concentrated in vacuo to give compound 1g2 (100 g, 88% yield) as yellow solid. $^1H$ NMR (400 MHz, DMSO-$d_6$) δ 7.52 (d, J=12.4 Hz, 2H), 7.10-7.04 (m, 1H), 6.50 (d, J=8.0 Hz, 2H), 6.33-6.28 (m, 1H), 6.16 (s, 2H). The solution of compound 1g2 (30 g, 19.5 mmol) in $CH(OEt)_3$ (300 mL) was stirred at 140° C. for 72 hours. Then the resulting mixture was concentrated to obtain the crude residue which was re-crystallized from ethyl acetate/PE=1:2 (v/v) to afford compound 1g3 (28 g, Yield: 87.8%) as white solid. $^1H$ NMR (400 MHz, DMSO-$d_6$) δ 12.28 (s, 1H), 8.08 (s, 1H), 7.81-7.75 (m, 1H), 7.48 (d, J=8.0 Hz, 1H), 7.29-7.24 (m, 1H). A solution of compound 1g3 (20 g, 12.2 mmol) in $SOCl_2$ (400 mL) and anhydrous DMF (5 mL) was stirred at reflux for 24 h. Then, the mixture was concentrated to afford compound 1g (24 g, Yield: 99%) as yellow solid which was used for the next step without further purification. $^1H$ NMR (400 MHz, $CDCl_3$) δ 9.23 (s, 1H), 8.49 (d, J=8.4, 1H), 8.15-8.21 (m, 1H), 7.62-7.66 (m, 1H).

Procedure for the Preparation of Compound 1h:

The mixture of comound 1g (3 g, 6.48 mmol) and compound 1f (3.95 g, 16.48 mmol) in anhydrous $CH_3CN$ (30 mL) was stirred at reflux for 2 h. The solid was precipitated from the mixture. The mixture was cooled down to room temperature (25-30° C.) and the mixture was filtered to obtain the desired comound 1h (5 g, 78.1% yield) as yellow solid. LCMS: $R_t$=2.144 min in 0-60AB_4 min chromatography (Welch Xtimate C18, 2.1*30 mm, 3 um), MS (ESI) m/z=387.0 $[M+H]^+$. $^1H$ NMR (400 MHz, Methanol-$d_4$) δ 9.13-9.10 (m, 2H), 8.84 (s, 1H), 8.20-8.15 (m, 1H), 7.78-7.77 (m, 2H), 7.73-7.68 (m, 2H), 7.50 (dd, $J_1$=2.4 Hz, $J_2$=7.6 Hz, 1H), 7.40 (d, J=8.4 Hz, 1H), 7.26 (d, J=2.0 Hz, 1H), 2.32 (s, 3H).

Procedure for the Preparation of Compound 1i:

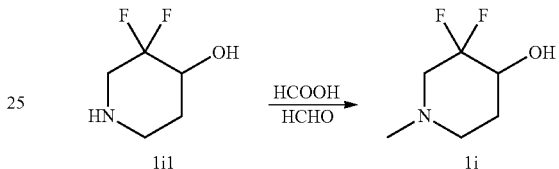

To a solution of comound 1i1 (130g, 0.948 mol) in an ice-salted cold bath was added 98% HCOOH (200 mL, 4.47 mol). The resulting mixture was warmed up to 25° C. and 40% HCHO (137 mL, 1.896 mol) was added. A lot of gas was released during the heating up to 40° C. After completion, the solution was adjust to pH=9-10 by adding concentrated NaOH and extracted with EtOAc (1.5L×3), washed with water and brine (1.6 L). The organic layer was dried over $NaSO_4$ and concentrated to give comound 1i (116.8 g, crude) as a white solid.

Procedure for the preparation of compounds of Compound 1 and Compound 1':

A solution of comound 1h (100 mg, 0.259 mmol), comound 1i (118 mg, 0.778 mmol), t-BuOK (146 mg, 1.3 mmol) in DMF (2 mL) was stirred for 16 hours at 100° C. The mixture was purified by reverse phase preparative HPLC (column: Sunfire C8 30*100 mm*5 um, gradient: 0-20% B (A=47ater/0.05% HCl, B=acetonitrile), flow rate: 30 mL/min) to afford 1j which was separated by SFC separation to give enantiomers Compound 1' (28.6 mg) & Compound 1 (26.0 mg).

Compound 1: LCMS: $R_t$=1.931 min in 0-60AB_4 min chromatography (Welch Xtimate C18, 2.1*30 mm, 3 um), MS (ESI) m/z=518.4 $[M+H]^+$. $^1H$ NMR (400 MHz, Methanol-$d_4$) δ 8.74 (d, J=7.6 Hz, 1H), 8.53 (s, 1H), 8.28 (s, 1H), 7.85 (m, 2H), 7.78 (t, J=8.4 Hz, 1H), 7.45 (d, J=8.4 Hz, 1H), 7.32 (d, J=8.4 Hz, 1H), 7.18 (d, J=8.8 Hz, 1H), 7.07 (dd, $J_1$=2.4 Hz, $J_2$=8.4 Hz, 1H), 6.81 (d, J=2.4 Hz, 1H), 5.17-5.08 (m, 1H), 3.27 (m, 1H), 2.98-2.95 (m, 1H), 2.68-2.58 (m, 1H), 2.48-2.41 (m, 2H), 2.41 (s, 3H), 2.12 (s, 3H), 2.10-2.03 (m, 1H).

Example 2

N-(4-([1,2,4]triazolo pyridin-7-yloxy)-3-methylphenyl)-5-(((1R,3r,5S)-8-(2,2-difluoroethyl)-8-azabicyclo[3.2.1]octan-3-yl)oxy)quinazolin-4-amine

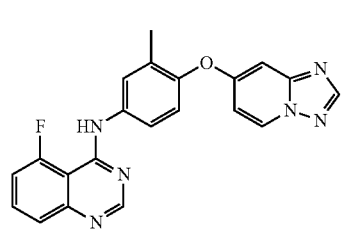

1h

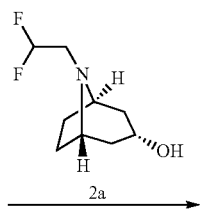
2a

Compound 2

Procedure for the Preparation of Compound 2:

To a solution of compound 1h (100 mg, 0.26 mmol) in THF (3 mL) and DMF (3 mL) was added compound 2a (99 mg, 0.52 mmol), t-BuOK (88 mg, 0.78 mmol). After addition, the mixture was stirred at 90° C. for 5 days. The mxiture was filtered, concentrated, purified by HPLC (column: ASB 150*25 mm*5 um, gradient: 5-30% B (HCl, B=acetonitrile), flow rate: 30 mL/min) to give Compound 2 (10 mg, 6.9%).

Compound 2: LCMS: $R_t$=1.865 min in 10-80AB_4 min chromatography (Xtimate C18, 2.1*30 mm, 3 um), MS (ESI) m/z=558.1 [M+H]$^+$. $^1$H NMR (400 MHz, Methanol-$d_4$) δ 9.07 (d, J=7.6 Hz, 1H), 9.01 (d, J=6.4 Hz, 1H), 8.79 (s, 1H), 8.09 (t, J=8.4 Hz, 1H), 7.87 (s, 1H), 7.76-7.69 (m, 1H), 7.51-7.40 (m, 3H), 7.37 (d, J=8.0 Hz, 1H), 7.19 (s, 1H), 6.55 (tt, $J_1$=53.6 Hz, $J_2$=3.2 Hz, 1H), 5.29 (s, 1H), 4.25 (s, 2H), 3.73-3.60 (m, 2H), 2.90-2.86 (m, 2H), 2.70-2.67 (m, 2H), 2.41 (s, 2H), 2.32-2.28 (m, 5H).

Example 3

N-(4-([1,2,4]triazolo pyridin-7-yloxy)-3-methylphenyl)-5-(((3R,4S)-3-fluoro-1-methylpiperidin-4-yl)oxy)-6-methoxyquinazolin-4-amine

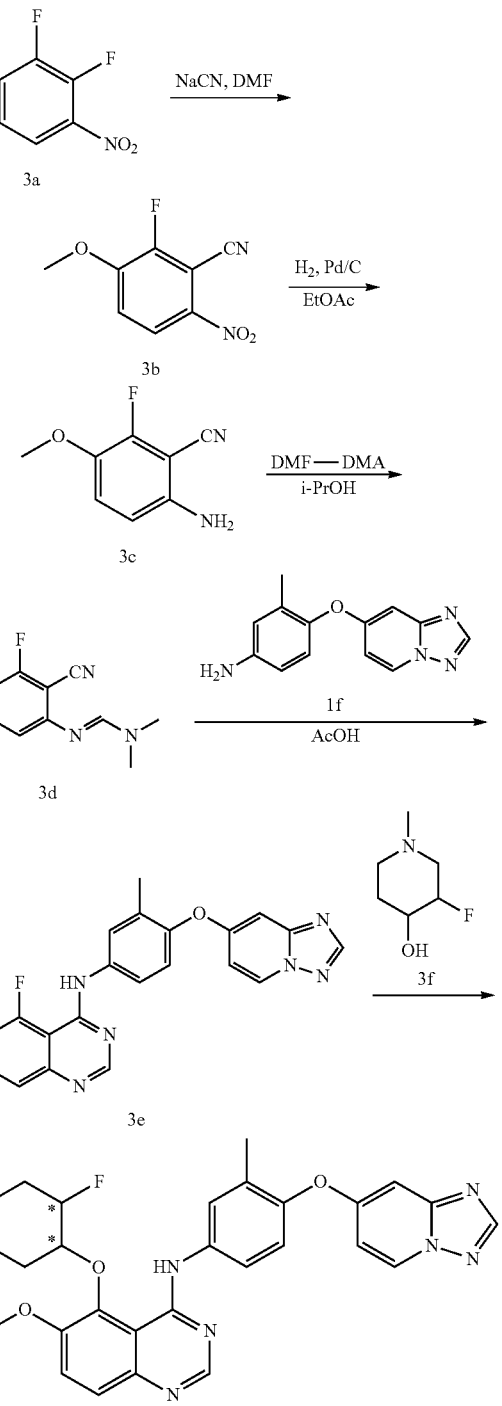

Compound 3: *enantiomercially pure cis isomer

Procedure for the Preparation of Compound 3b:

To a solution of compound 3a (5.0 g, 26.44 mmol) in DMF (50 mL) was added NaCN (1.43 g, 29.08 mmol). The reaction mixture was stirred at 20° C. for 12 hours. The mixture was concentrated to give the residue. The residue was dissolved in EtOAc (80 mL) and washed with water (20 mL×2) and saturated brine (20 mL×2). The organic layers were dried over $Na_2SO_4$, filtered and evaporated to afford crude product which was purified by flash silica chromatography (PE/EtOAc=20:1 to 5:1(v/v)) and concentrated to afford compound 3b (2.5 g, 48.1% yield) as a yellow solid. LCMS: $R_t$=0.845 min in 10-80AB_2.0 min_E chromatography (Merck RP-18e 25-2 mm, SN: UM9504/198), MS (ESI) m/z=197.1 [M+H]$^+$.

$^1$H NMR (400 MHz, $CDCl_3$) δ 8.22 (br d, J=8.80 Hz, 1H), 7.24-7.33 (m, 1H), 4.09 (s, 3H).

Procedure for the Preparation of Compound 3c:

To a solution of compound 3b (2.3 g, 11.73 mmol) in AcOH (25 mL) and water (0.3 mL) at 0° C. was added Fe (3.27 g, 58.63 mmol). The resulting mixture was stirred at 20° C. for 16 hours. The mixture was filtered and the filtrate was concentrated under reduced pressure to give the residue. The residue was dissolved in ethyl acetate (50 mL) and adjusted with saturated $NaHCO_3$ to pH=8-9. The organic phase was washed with water (20 mL), brine (20 mL), dried over $Na_2SO_4$, filtered and concentrated to yield compound 3c (2 g, crude) as a yellow solid. LCMS: $R_t$=0.689 min in 10-80AB_2 min_E chromatography (Merck RP-18e 25-2 mm, SN: UM9504/198), MS (ESI) m/z=167.1 [M+H]$^+$. $^1$H NMR (400 MHz, $CDCl_3$) δ 7.06 (t, J=9.00 Hz, 1H), 6.46 (dd, J=9.00, 1.76 Hz, 1H), 4.21 (br s, 2H), 3.71-3.91 (m, 3H).

Procedure for the Preparation of Compound 3d:

A mixture of compound 3c (1 g, 6.02 mmol) in DMF-DMA (15 mL) was stirred at 100° C. for 12 hours. The mixture was concentrated to afford crude compound 3d (1.5 g, crude) as a yellow solid. LCMS: $R_t$=0.577 min in 0-60AB_2 min_E chromatography (Merck RP-18e 25-2 mm, SN: UM9504/198), MS (ESI) m/z=222.1 [M+H]$^+$. $^1$H NMR (400 MHz, Methanol-$d_4$) δ 7.73 (s, 1H), 7.27 (t, J=9.26 Hz, 1H), 6.82 (dd, J=9.04, 1.76 Hz, 1H), 3.72-3.98 (m, 3H), 3.01-3.14 (m, 6H).

Procedure for the Preparation of Compound 3e:

A mixture of compound 3d (1.5 g, 6.78 mmol) and compound 1f (2.44 g, 10.17 mmol) in AcOH (20 mL) was stirred at 50° C. for 12 h. The mixture was concentrated under vacuum. The residue was suspended in EtOAc (15 mL) and adjusted pH to 8-9 with saturated $K_2CO_3$ (aq), filtered and the cake was washed with ethyl acetate (5 mL) to afford N-(4-([1,2,4]triazolo[1,5-a]pyridin-7-yloxy)-3-methylphenyl)-5-fluoro-6-methoxyquinazolin-4-amine (Y02, 2 g, 4.81 mmol, 90.0 mass %, 70.9% yield) as a brown solid. LCMS: $R_t$=1.022 min in 0-60AB_2 min_E chromatography (Merck RP-18e 25-2 mm, SN: UM9504/198), MS (ESI) m/z=417.2 [M+H]$^+$. $^1$H NMR (400 MHz, Methanol-$d_4$) δ 8.71-8.77 (m, 1H), 8.44 (s, 1H), 8.27-8.31 (m, 1H), 7.79-7.88 (m, 1H), 7.70-7.77 (m, 2H), 7.66 (dd, J=9.26, 1.76 Hz, 1H), 7.19 (d, J=8.60 Hz, 1H), 7.05-7.11 (m, 1H), 6.85 (d, J=2.43 Hz, 1H), 4.05 (s, 3H), 2.25 (s, 3H).

Procedure for the Preparation of Compound 3:

A mixture of compound 3e (400 mg, 537.9 umol, 56% purity) and compound 3f (214.9 mg, 1.61 mmol, 3.0 eq) and t-BuOK (211.3 mg, 1.88 mmol, 3.5 eq) in DMF (5 mL) was stirred at 130° C. for 16 hours. The mixture was adjusted to pH=7-8, filtered, the filtration was purified by neutral pre-HPLC (column: Phenomenex Gemini C18 200*25 mm*10 um, gradient: 28-58% B (A: $H_2O$, B: $CH_3CN$), flow rate: 25 mL/min) followed by SFC separation gave cis-isomer of Compound 3 (40 mg, 14% yield) as white solid.

Compound 3: LCMS: $R_t$=1.906 min in 0-60AB_4 min chromatography (Xtimate C18, 2.1*30 mm, 3 um), MS (ESI) m/z=530.1[M+H]$^+$. $^1$H NMR (400 MHz, Methanol-$d_4$) δ 8.74 (d, J=7.2 Hz, 1H), 8.40 (s, 1H), 8.28 (s, 1H), 7.84 (s, 1H), 7.84-7.81 (m, 1H), 7.76 (d, J=9.2 Hz, 1H), 7.61 (d, J=9.2 Hz, 1H), 7.15 (d, J=8.8 Hz, 1H), 7.06 (dd, J=2.4 Hz and 7.6 Hz, 1H), 6.81 (d, J=2.4 Hz, 1H), 5.20-5.07 (m, 1H), 4.98-4.89 (m, 1H), 4.04 (s, 3H), 3.25-3.23 (m, 1H), 2.91 (d, J=8.0 Hz, 1H), 2.28 (s, 3H), 2.24 (s, 3H), 2.49-2.15 (m, 3H).

Example 4

(R)—N-(4-([1,2,4]triazolo pyridin-7-yloxy)-3-methylphenyl)-5-((4,4-difluoro-1-methylpiperidin-2-yl)methoxy)-6-methoxyquinazolin-4-amine

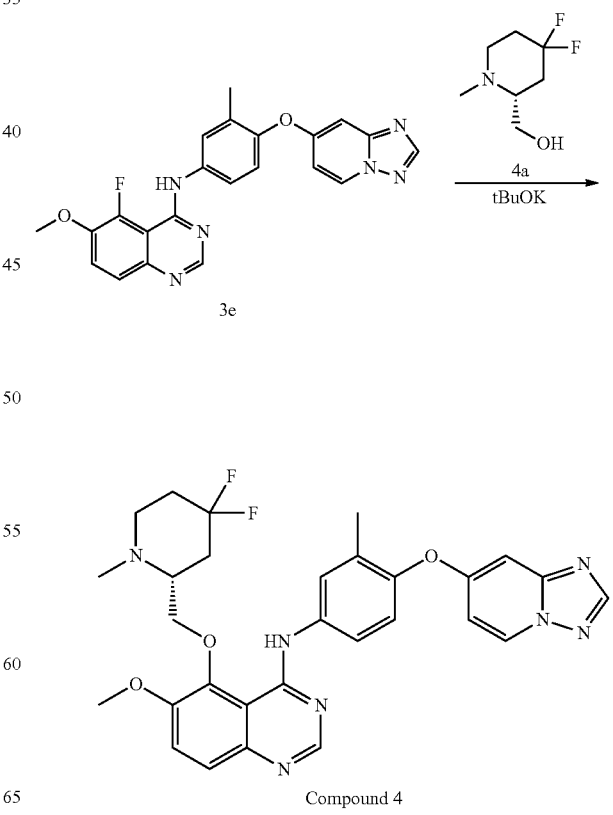

Compound 4

To a solution of compound 3e (100 mg, 0.24 mmol) in THF (6 mL) and DMF (4 mL) was added compound 4a (119 mg, 0.72 mmol), t-BuOK (94 mg, 0.84 mmol). After addition, the mixture was stirred at 80° C. for 24 hours. It was filtered, concentrated, purified by HPLC (column: Agella Venusil ASB C18 150*21.2 mm*5 um, gradient: 10-40% B (HCl, B=acetonitrile), flow rate: 25 mL/min) to give Compound 4 (80 mg, 59.3% yield). Compound 4: LCMS: $R_f$=2.079 min in 10-80AB_4 min chromatography (Xtimate C18, 2.1*30 mm, 3 um), MS (ESI) m/z=562.1 [M+H]$^+$. $^1$H NMR (400 MHz, Methanol-$d_4$) δ 9.08 (d, J=7.6 Hz, 1H), 9.04 (s, 1H), 8.71 (s, 1H), 8.07 (d, J=9.2 Hz, 1H), 7.91-7.88 (m, 2H), 7.76 (d, J=9.2 Hz, 1H), 7.45 (dd, $J_1$=7.6 Hz, $J_2$=2.4 Hz, 1H), 7.36 (d, J=8.8 Hz, 1H), 7.21 (d, J=2.4 Hz, 1H), 4.87 (m, 1H), 4.58-4.55 (m, 1H), 4.17 (s, 3H), 4.09-4.05 (m, 1H), 3.77 (m, 1H), 3.51-3.48 (m, 1H), 3.26 (s, 3H), 2.86-2.69 (m, 3H), 2.47-2.44 (m, 1H), 2.30 (s, 3H).

Example 5

N-(4-([1,2,4]triazolo[1,5-a]pyridin-7-yloxy)-3-methylphenyl)-5-((4,4-difluoro-1-methylpiperidin-3-yl)oxy)-6-methoxyquinazolin-4-amine

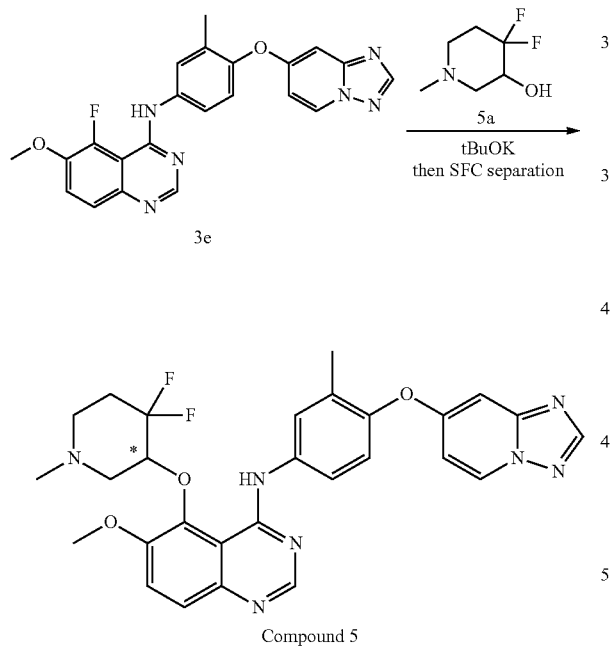

The synthesis followed a similar experimental procedure as Compound 3 to afford enantiomer Compound 5 as solid after SFC separation.

Compound 5: LCMS: $R_f$=2.065 min in 0-60AB_4 min chromatography (Welch Xtimate C18, 2.1*30 mm, 3 um), MS (ESI) m/z=548.3 [M+H]$^+$. $^1$H NMR (400 MHz, DMSO-$d_6$) δ 12.69-12.04 (m, 1H), 10.86-10.49 (m, 1H), 8.98 (d, J=7.2 Hz, 1H), 8.81 (s, 1H), 8.42 (s, 1H), 8.06 (d, J=9.6 Hz, 1H), 7.86 (d, J=8.8 Hz, 1H), 7.80 (s, 1H), 7.68 (s, 1H), 7.31 (d, J=6.0 Hz, 1H), 7.06 (dd, $J_1$=2.8 Hz, $J_2$=7.6 Hz, 1H), 6.83 (s, 1H), 5.56-4.88 (m, 1H), 4.27-4.23 (m, 6H), 4.12 (brs, 1H), 3.31 (brs, 3H), 2.91 (s, 3H), 2.58 (brs, 1H), 2.23 (s, 3H)

Example 6

Enantiomer-1

(S)—N-(4-([1,2,4]triazolo[1,5-a]pyridin-7-yloxy)-3-methylphenyl)-5-((3,3-difluoro-1-methylpiperidin-4-yl)oxy)-7-methoxyquinazolin-4-amine And Enantiomer-2

(R)—N-(4-([1,2,4]triazolo[1,5-a]pyridin-7-yloxy)-3-methylphenyl)-5-((3,3-difluoro-1-methylpiperidin-4-yl)oxy)-7-methoxyquinazolin-4-amine

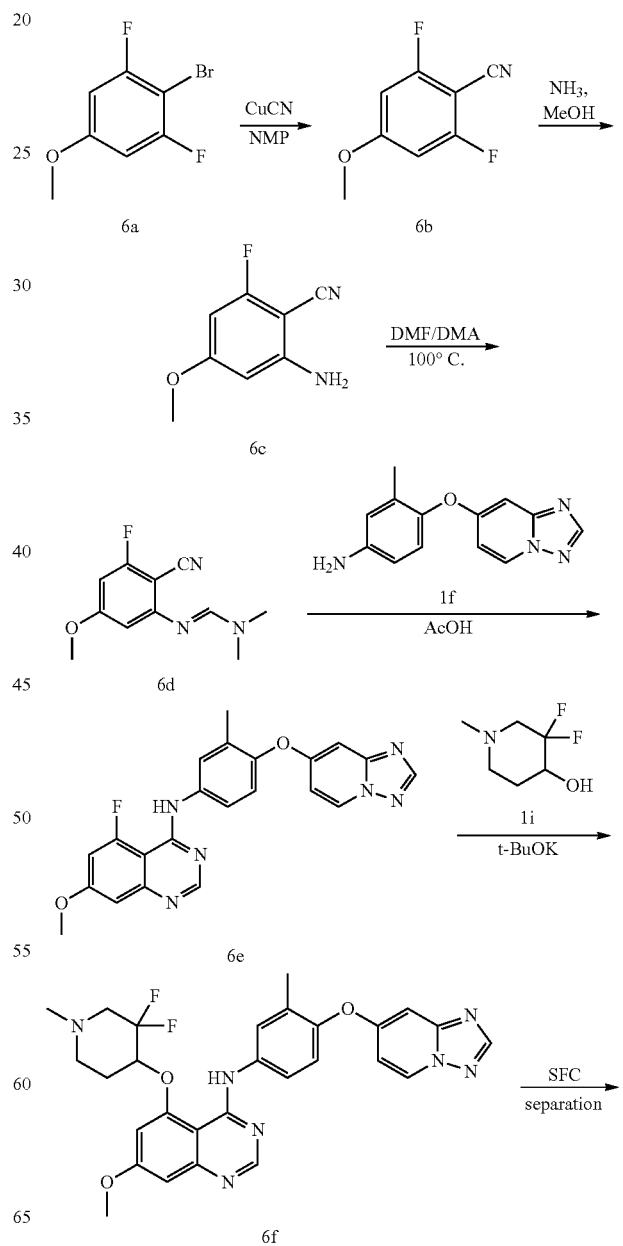

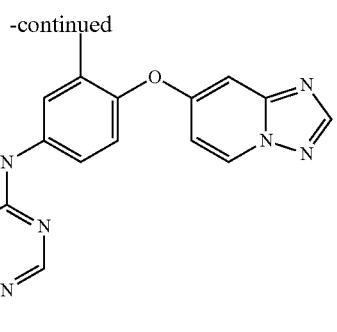

Compound 6: enantiomer-1

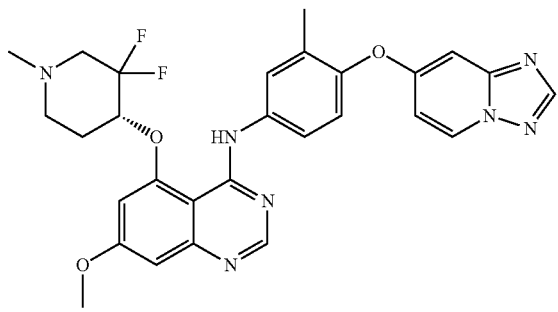

Compound 6': enantiomer-2

Procedure for the Preparation of Compound 6b:

A mixture of compound 6a (2.5 g, 11.2 mmol) and CuCN (2.9 g, 22.4 mmol) in NMP (25 mL) was stirred at 160° C. for 5 hours. After cooling to room temperature, filtered and concentrated, the crude product 6b was used directly in next step without further purification.

Procedure for the Preparation of Compound 6c:

$NH_3$ gas was pumped into 100 mL of EtOH at 0° C. for 15 minuets, and the compound 6b (3 g crude) was dissolved in 30 mL of MeOH, the mixture was stirred at 120° C. in seal tube overnight. The solution was concentrated and the residue was purified by column chromatography in silica gel (PE/EtOAc=1/1) to give compound 6c (450 mg, 24% yield for two steps) as a white solid. $^1$H NMR (400 MHz, DMSO-$d_6$) δ 6.38 (s, 2H), 6.17 (d, J=2 Hz, 1H), 6.13 (dd, $J_1$=2.0 Hz, =9.2 Hz, 1H), 3.73 (s, 3H).

Procedure for the Preparation of Compound 6d:

A mixture of compound 6c (2 g crude) in DMF-DMA (8 mL) was stirred at 100° C. for 2 hours, after cooling to room temperature, the mixture was filtered and the precipitate was washed with ethyl acetate to give compound 6d (800 mg, crude) as a yellow solid which was used in the next step directly.

Procedure for the Preparation of Compound 6e:

A mixture of compound 6d (800 mg, 3.62 mmol) and compound 1f (1.303g, 5.43 mmol) in AcOH (15 mL) was stirred at 40-60° C. overnight. Concentrated and adjusted pH to 8-9 with $K_2CO_3$ (aq), filtered and the cake was washed with ethyl acetate to give compound 6e (1.6 g, crude) as a brown solid. LCMS: $R_t$=0.702 min in 5-95AB_1.5 min chromatography (Xtimate C18 2.1*30 mm), MS (ESI) m/z 417.0 [M+H]$^+$. $^1$H NMR (400 MHz, Methanol-$d_4$) δ 8.74 (d, J=7.2 Hz, 1H), 8.46 (s, 1H), 8.29 (s, 1H), 7.71 (s, 1H), 7.67 (dd, $J_1$=2.4 Hz, $J_2$=8.4 Hz, 1H), 7.18 (d, J=8.4 Hz, 1H), 7.09-7.00 (m, 3H), 6.85 (d, J=2.4 Hz, 1H), 3.98 (s, 3H), 2.25 (s, 3H).

Procedure for the Preparation of Compound 6:

A mixture of compound 6e (1.1 g, 2.64 mmol), comound 1i (991 mg, 5.28 mmol) and t-BuOK (889 mg, 7.92 mmol) in THF/DMF (15/6 mL) was stirred at 80~100° C. overnight under $N_2$ protection. The mixture was concentrated and the residue was purified by reverse phase preparative HPLC (column: SYNERGI 250*50 10 um, gradient: 40-70% B (A=water/0.05% $NH_4HCO_3$, B=acetonitrile), flow rate: 80 mL/min) to afford compound 6f and then the compound was separated by SFC to give 170 mg of Compound 6 and 170 mg of Compound 6'.

Compound 6 (enantiomer-1): LCMS: $R_t$=2.001 min in 0-60AB_4 min chromatography (Xtimate C18, 2.1*30 mm, 3 um), MS (ESI) m/z=548.1 [M+H]$^+$. $^1$H NMR (400 MHz, Methanol-$d_4$) δ 8.89 (d, J=7.6 Hz, 1H), 8.77 (s, 1H), 8.58 (s, 1H), 7.82 (d, J=2.4 Hz, 1H), 7.77 (dd,=9.2 Hz, $J_2$=2.8 Hz, 1H), 7.31 (d, J=8.4 Hz, 1H), 7.26 (dd,=13.6 Hz, $J_2$=2.0 Hz, 2H), 6.95 (d, J=2.0 Hz, 1H), 6.92 (s, 1H), 5.67-5.59 (m, 1H), 4.28 (brs, 1H), 4.08 (s, 3H), 3.91-3.76 (m, 2H), 3.53-3.47 (m, 1H), 3.07 (s, 3H), 2.88 (d, J=13.2 Hz, 1H), 2.43-2.40 (m, 1H), 2.29 (s, 3H).

Compound 6'(enantiomer-2): LCMS: $R_t$=2.009 min in 0-60AB_4 min chromatography (Xtimate C18, 2.1*30 mm, 3 um), MS (ESI) m/z=548.0 [M+H]$^+$. $^1$H NMR (400 MHz, Methanol-$d_4$) δ 8.89 (d, J=7.2 Hz, 1H), 8.76 (s, 1H), 8.57 (s, 1H), 7.82 (d, J=2.4 Hz, 1H), 7.77 (dd,=8.4 Hz, $J_2$=2.4 Hz, 1H), 7.30 (d, J=8.8 Hz, 1H), 7.22 (dd,=7.6 Hz, $J_2$=2.4 Hz, 2H), 6.96 (d, J=2.4 Hz, 1H), 6.91 (d, J=2.4 Hz, 1H), 5.72-5.63 (m, 1H), 4.26-4.24 (m, 1H), 4.08 (s, 3H), 3.94-3.76 (m, 2H), 3.57-3.51 (m, 1H), 3.07 (s, 3H), 2.87 (d, J=14.4 Hz, 1H), 2.48-2.42 (m, 1H), 2.29 (s, 3H).

Example 7

5-((3,3-difluoro-1-methylpiperidin-4-yl)oxy)-N-(3-methyl-4-((1-methyl-1H-benzo[d]imidazol-5-yl)oxy)phenyl)quinazolin-4-amine

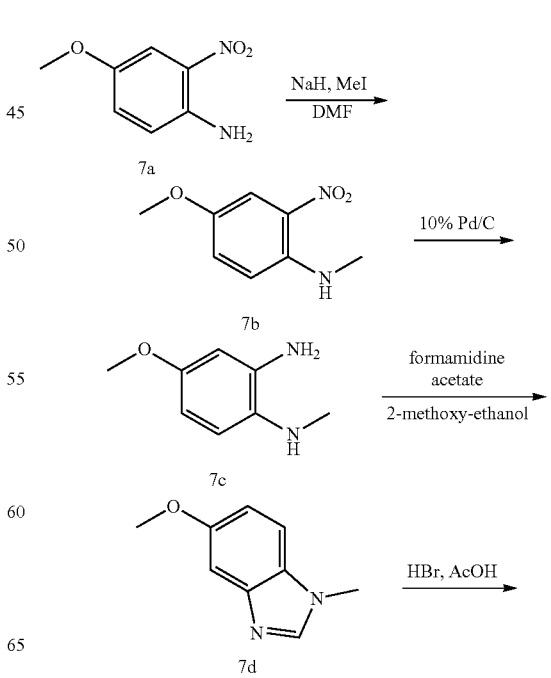

-continued

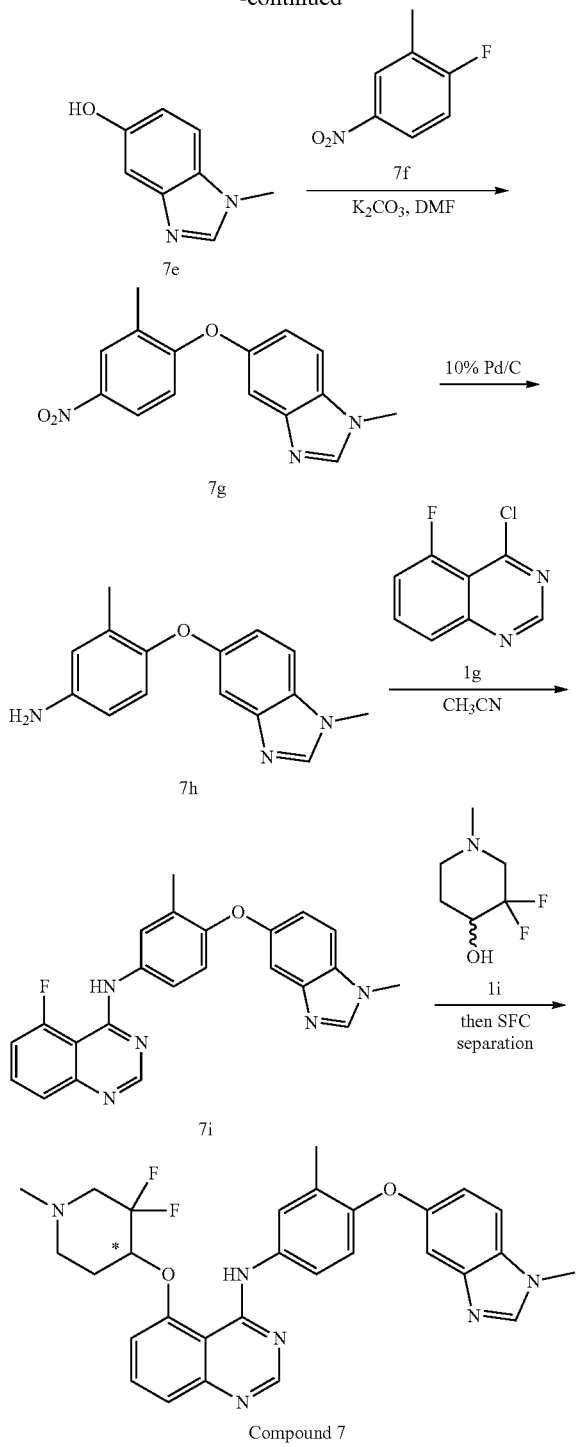

Procedure for the Preparation of Compound 7b:

To a solution of Compound 7a (5.0 g, 29.76 mmol) in DMF (50 mL) was added NaH (1.3 g, 32.74 mmol) at 0° C. and stirred for 10 minutes. MeI (6.34 g, 44.64 mmol) was added and stirred at 35° C. for 1.5 hours. TLC showed Compound 1 was consumed completely. The solution was added water (50 mL) and extracted with EtOAc (100 mL×3). The combined organic layer was washed with brine (100 mL*3), dried over $Na_2SO_4$, filtered and concentrated to give compound 7b (6.2 g, 100%) as a red solid. $^1H$ NMR (400 MHz, $CDCl_3$) δ 7.62 (d, J=2.8 Hz, 1H), 7.18 (dd, J=9.6 Hz, 3.2 Hz, 1H), 6.82 (d, J=9.6 Hz, 1H), 3.80 (s, 3H), 3.02 (d, J=5.2 Hz, 3H).

Procedure for the Preparation of Compound 7c:

To a solution of compound 7b (6.2 g, 34.06 mmol) in EtOH (147 mL) and THF (27 mL) was added Pd/C (1.0 g) and the solution was stirred under $H_2$ balloon at room temperature for 4 hours. After completion, the solution was filtered, concentrated and purified by column chromatography (PE:EtOAc=3:1(v/v)) to give compound 7c (3.5 g, 69%) as a solid. $^1H$ NMR (400 MHz, $CDCl_3$) δ 6.60 (d, J=8.4 Hz, 1H), 6.39-6.35 (m, 2H), 3.74 (s, 3H), 2.82 (s, 3H).

Procedure for the Preparation of Compound 7d:

To a solution of Compound 7c (3.5 g, 23.03 mmol) and formamidine acetate (4.8 g, 46.06 mmol) in 2-methoxyethanol (60 mL) was stirred at 120° C. for 20 hours. The mixture was then concentrated and added $H_2O$ (60 mL), extracted with $CH_2Cl_2$ (150 mL×3). The combined organic layer was washed with brine (100 mL×3), dried over $Na_2SO_4$, filtered, concentrated to give compound 7d (3.6 g, 97%) as a solid. $^1H$ NMR (400 MHz, $CDCl_3$) δ 7.83 (s, 1H), 7.29-7.26 (m, 2H), 6.97 (dd, $J_1$=2.4 Hz, $J_2$=8.8 Hz, 1H), 3.87 (s, 3H), 3.82 (s, 3H).

Procedure for the Preparation of Compound 7e:

To a solution of compound 7d (1.0 g, 6.17 mmol) in 38% HBr (30 mL) and AcOH (30 mL) was stirred at 110° C. for 48 hours. After completion, the mixture was concentrated and neutralized to pH=7 with $Na_2CO_3$. The mixture was extracted with EtOAc (100 mL×3). The combined organic layer was washed with brine (100 mL×3), dried over $Na_2SO_4$, filtered, concentrated to give compound 7e (0.2 g, 22%) as a solid. $^1H$ NMR (400 MHz, Methanol-$d_4$) δ 7.97 (s, 1H), 7.34 (d, J=8.8 Hz, 1H), 7.03 (d, J=2.4 Hz, 1H), 6.87 (dd, $J_1$=2.4 Hz, $J_2$=8.8 Hz, 1H), 3.84 (s, 3H).

Procedure for the Preparation of Compound 7g:

To a solution of compound 7e (209.0 mg, 1.35 mmol) and compound 7f (200.0 mg, 1.35 mmol) in DMF (5 mL) was added $K_2CO_3$ (209.0 mg, 1.35 mmol) and stirred at 80° C. for 20 hours. After completion, the mixture was added by water (10 mL), extracted with EtOAc (50 mL×3), and the combined organic layer was washed with brine (50 mL×3), dried over $Na_2SO_4$, filtered, concentrated to give compound 7g (0.4 g, crude) as a yellow solid. $^1H$ NMR (400 MHz, $CDCl_3$) δ 8.15 (d, J=2.0 Hz, 1H), 7.95 (d, J=2.8 Hz, 1H), 7.93 (d, J=2.8 Hz, 1H), 7.48 (d, J=2.0 Hz, 1H), 7.42 (d, J=8.4 Hz, 1H), 7.26 (s, 1H), 7.07 (dd, 2.4 Hz, $J_2$=8.8 Hz, 1H), 6.67 (d, J=9.2 Hz, 1H), 3.89 (s, 2H), 2.46 (s, 3H).

Procedure for the Preparation of Compound 7h:

To a solution of compound 7g (400.0 mg, 1.41 mmol) in MeOH (50 mL) was added Pd/C (0.5 g) and stirred under $H_2$ balloon at room temperature for 2 hours. After completion, the mixture was filtered and concentrated to give compound 7h (340 mg, 69% yield) as a red solid.

$^1H$ NMR (400 MHz, DMSO-$d_6$) δ 8.09 (s, 1H), 7.46 (d, J=8.8 Hz, 1H), 6.89-6.85 (m, 2H), 6.65 (d, J=8.4 Hz, 1H), 6.49 (d, J=2.4 Hz, 1H), 6.42 (dd, $J_1$=2.4 Hz, $J_2$=8.4 Hz, 1H), 4.88 (s, 2H), 3.79 (s, 3H), 1.99 (s, 3H).

Procedure for the Preparation of Compound 7i:

A solution of compound 7h (340.0 mg, 1.344 mmol) and comound 1g (244.0 mg, 1.344 mmol) in $CH_3CN$ (40 mL) was stirred at 80° C. for 20 hours. After completion, the mixture was concentrated to give compound 7l (530.0 mg, 98.0% yield) as a yellow solid. LCMS: $R_t$=1.351 min in 10-80AB_4 min chromatography (Welch Xtimate C18, 2.1*30 mm, 3 um), MS (ESI) m/z=400.1 [M+H]$^+$. $^1H$ NMR (400 MHz, Methanol-4) δ 8.49 (s, 1H), 8.10 (s, 1H), 7.85-7.79 (m, 1H), 7.61 (d, J=8.4 Hz, 2H), 7.55-7.48 (m, 2H), 7.35 (dd, J$_1$=8.0 Hz, J$_2$=12.8 Hz, 1H), 7.15 (d, J=2.0 Hz, 1H), 7.08 (dd, J$_1$=2.4 Hz, J$_2$=8.8 Hz, 1H), 6.88 (d, J=8.8 Hz, 1H), 3.90 (s, 3H), 2.30 (s, 3H).

Procedure for the Preparation of Compound 7:

To a solution of compound 7i (430.0 mg, 1.08 mmol), comound 1i (325.0 mg, 2.16 mmol) and t-BuOK (362.0 mg, 3.24 mmol) in DMF (5 mL) and THF (5 mL) was stirred at 100° C. for 20 hours. The mixture was filtered and concentrated and the crude was purified by HPLC (column: Phenomenex Gemini C18 200*25 mm*10 um, gradient: 10-20% B (A=water/0.05% TFA, B=acetonitrile) followed by SFC separation gave enantiomer Compound 7 (140 mg, yield 24%) as a white solid.

Compound 7: LCMS: R$_t$=1.166 min in 10-80AB_4 min chromatography (Welch Xtimate C18, 2.1*30 mm, 3 um), MS (ESI) m/z=531.1 [M+H]$^+$. $^1$H NMR (400 MHz, Methanol-d$_4$) δ 9.37 (s, 1H), 8.83 (s, 1H), 8.10 (t, J=8.4 Hz, 1H), 7.95 (d, J=9.2 Hz, 1H), 7.77-7.73 (m, 2H), 7.56 (d, J=8.4 Hz, 1H), 7.40 (dd, J$_1$=2.0 Hz, J$_2$=8.8 Hz, 1H), 7.30 (d, J=2.0 Hz, 1H), 7.10 (d, J=8.8 Hz, 1H), 5.81-5.73 (m, 1H), 4.32-4.27 (m, 1H), 4.17 (s, 3H), 4.06-3.95 (m, 1H), 3.81 (d, J=12.8 Hz, 1H), 3.69-3.62 (m, 1H), 3.10 (s, 3H), 2.92-2.88 (m, 1H), 2.51-2.47 (m, 1H), 2.32 (s, 3H).

Example 8

5-((3,3-difluoro-1-methylpiperidin-4-yl)oxy)-N-(4-(imidazo[1,2-a]pyridin-7-yloxy)-3-methylphenyl)-7-methoxyquinazolin-4-amine

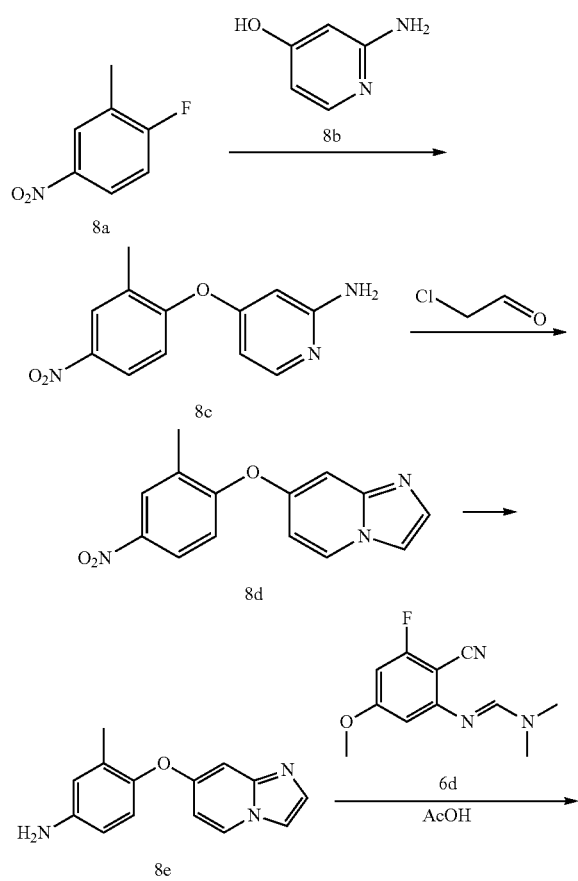

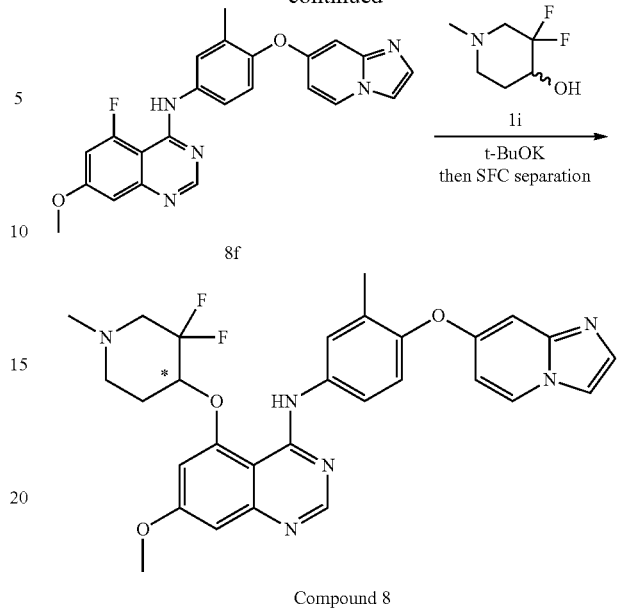

Compound 8

Procedure for the Preparation of Compound 8c:

A solution of compound 8a (12.68 g, 1.0 eq), compound 8b (9.0 g, 1.0 eq) and Cs$_2$CO$_3$ (53.26 g, 2.0 eq) in DMF (135 mL) was stirred at 80° C. for 16 hours. After completion, the mixture was poured into water, extracted with ethyl acetate (150 mL×3), washed with brine (150 mL×3), then dried over Na$_2$SO$_4$ and filtered, concentrated and the crude was purified by column chromatography (PE:EA=1:1(v/v)) on silica gel to give compound 8c (10 g, 49% yield) as a yellow solid. $^1$H NMR (400 MHz, DMSO-d$_6$) δ 8.28 (d, J=2.4 Hz, 1H), 8.13 (dd, J$_1$=8.8 Hz, J$_2$=2.4 Hz, 1H), 7.87 (d, J=6.0 Hz, 1H), 7.21 (d, J=8.8 Hz, 1H), 6.19 (dd, J$_1$=6.0 Hz, J$_2$=2.0 Hz, 1H), 6.04 (s, 2H), 5.89 (d, J=2.4 Hz, 1H), 2.27 (s, 3H).

Procedure for the Preparation of Compound 8d:

A solution of compound 8c (10.0 g, 1.0 eq) in 2-chloroacetaldehyde (137.9 g, 43.1 eq) was stirred at 80° C. for 16 hours. The mixture was quenched with sat. NaOH aqueous (50 mL), concentrated and purified by silica column chromatography (CH$_2$Cl$_2$/CH$_3$OH=10:1 (v/v)) to give compound 8d as a brown solid (9.0 g, 91.9% yield). LCMS: R$_t$=0.640 min in 5-95AB_4 min chromatography (Xtimate C18, 2.1*30 mm, 3 um), MS (ESI) m/z=269.9 [M+H]$^+$. $^1$H NMR (400 MHz, CDCl$_3$) δ 8.21 (d, J=2.4 Hz, 1H), 8.17 (d, J=7.6 Hz, 1H), 8.09 (dd, J$_1$=8.4 Hz, J$_2$=2.4 Hz, 1H), 7.62 (s, 1H), 7.57 (s, 1H), 7.10 (s, 1H), 7.04 (d, J=8.8 Hz, 1H), 6.75 (dd, J$_1$=7.6 Hz, J$_2$=2.4 Hz, 1H), 2.37 (s, 3H).

Procedure for the Preparation of Compound 8e:

To a solution of compound 8d (9.0 g, 1.0 eq) and NH$_4$Cl (17.88 g, 10.0 eq) in MeOH/H$_2$O=3:1(v/v) (100 mL) was added Fe (9.33 g, 5.0 eq), the mixture was stirred at 60° C. for 6 hours.

The suspension was filtered through Celite pad, the filtrate was concentrated under reduced pressure to give the crude product 8e which was used in the next step without further purification.

Procedure for the Preparation of Compound 8f:

A mixture of compound 6d (203.4 mg, 0.919 mmol) and compound 8e (200 mg, 0.836 mmol) in AcOH (5 mL) was stirred at 40-60° C. for 3 days. The AcOH was removed under vacuum and the residue was basified to pH 8-9 with aqueous Na$_2$CO$_3$ and filtered. The filtrate was dried to give compound 8f (250 mg, crude) as a red oil which was used directly in next step without further purification. LCMS: $R_f$=1.901 min in 0-60AB_4 min chromatography (Xtimate C18, 2.1*30 mm,), MS (ESI) m/z=416.0 [M+H]$^+$. $^1$H NMR (400 MHz, Methanol-d$_4$) δ 8.77 (d, J=7.6 Hz, 1H), 8.68 (s, 1H), 8.09 (s, 1H), 7.88 (d, J=2.0 Hz, 1H), 7.69 (s, 1H), 7.63 (d, J=2.4 Hz, 1H), 7.36-7.28 (m, 3H), 7.08 (s, 1H), 7.04 (s, 1H), 4.06 (s, 3H), 2.29 (s, 3H).

Procedure for the preparation of Compound 8:

A mixture of compound 8f (250 mg, 0.6 mmol), comound 1i (136.4 mg, 0.9 mmol) and t-BuOK (134.4 mg, 1.2 mmol) in THF (5 mL) and DMF (2 mL) was stirred at 80-100° C. overnight. The mixture was concentrated and the crude was purified by a reverse phase preparative HPLC (Column: Sunfire C8 30*100 mm*5 um, gradient: 0-20% B (A=water/0.05% HCl, B=acetonitrile), flow rate: 30 mL/min) followed by SFC separation to afford enantiomer Compound 8 (18.2 mg, 5.6% yield for two steps) as a yellow solid.

Compound 8: LCMS: $R_f$=1.81 min in 0-60AB_4 min chromatography (Xtimate C18 2.1*30 mm), MS (ESI) m/z=547.1 [M+H]$^+$. $^1$H NMR (400 MHz, Methanol-d4) δ 8.79 (d, J=7.2 Hz, 1H), 8.77 (s, 1H), 8.10 (d, J=2.0 Hz, 1H), 7.89-7.79 (m, 3H), 7.35-7.31 (m, 3H), 7.02 (d, J=2.4 Hz, 1H), 6.98 (s, 1H), 5.73 (brs, 1H), 4.29-4.26 (m, 1H), 4.08 (s, 3H), 4.01-3.89 (m, 1H), 3.79 (d, J=12.8 Hz, 1H), 3.63-3.57 (m, 1H), 3.09 (s, 3H), 2.87 (s, 1H), 2.49-2.46 (m, 1H), 2.29 (s, 3H).

Example 9

5-((3,3-difluoro-1-methylpiperidin-4-yl)oxy)-N-(3-methyl-4-(pyrazolo pyridin-6-yl oxy)phenyl)quinazolin-4-amine

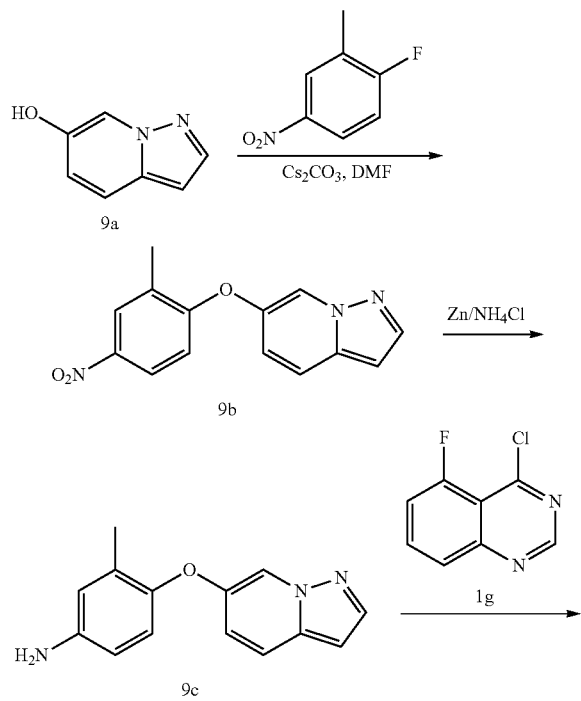

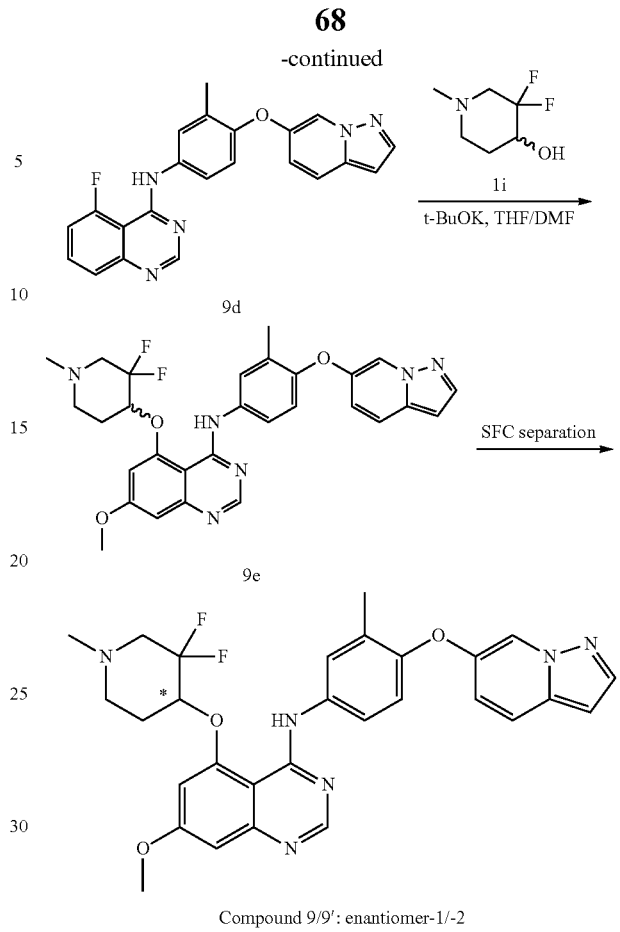

Compound 9/9': enantiomer-1/-2

Procedure for the Preparation of Compound 9b:

A mixture of 2-fluoro-1methyl-5-nitrobenzene (0.301 g, 1.0 eq), Cs$_2$CO$_3$ (1.26 g, 2.0 eq) and compound 9a (0.26 g, 1.0 eq.) in DMF (10 mL) was stirred at 80° C. for 2 hours. After completion, water (50 mL) was added to the mixture and the mixture was extracted with EtOAc (50 mL×3). The organic phase was combined and washed with brine, dried over Na$_2$SO$_4$, filtered, concentrated to give crude compound 9b which was purified by column chromatography on silica gel (Petroleum ether/Ethyl acetate=5:1) to give a yellow solid. (0.45 g, yield: 86%). LCMS: $R_f$=0.866 min in 5-95AB_1.5 min, chromatography (XMK RP-18e 25-2 mm), MS (ESI) m/z=269.9 [M+H]$^+$. $^1$H NMR: (400 MHz, CDCl$_3$) δ 8.37 (dd, J$_1$=1.2 Hz, J$_2$=2.4 Hz, 1H), 8.17 (dd, J$_f$=0.8 Hz, J$_2$=2.8 Hz, 1H), 8.02-7.99 (m, 1H), 7.98 (d, J=2.4 Hz, 1H), 7.61 (dd,=4.8 Hz, J$_2$=9.6 Hz, 1H), 6.96 (dd,=2.0 Hz, J$_2$=9.6 Hz, 1H), 6.82 (d, J=9.2 Hz, 1H), 6.61 (dd, J$_f$=0.8 Hz, J$_2$=2.4 Hz, 1H), 2.46 (s, 3H).

Procedure for the Preparation of Compound 9c:

To a solution of compound 9b (0.45 g, 1.0 eq.) and Zn powder (0.874 g, 8.0 eq.) in MeOH (20 mL) was added NH$_4$Cl (0.715 g, 8.0 eq.) in portions over 5 min. The mixture was stirred at 30° C. for 5 hours. After completion, the mixture was filtered and the filtrate was concentrated to give crude product, which was purified by flash chromatography to give a foam solid (0.36 g, 90% yield). LCMS: $R_f$=0.656 min in 5-95AB_1.5 min, chromatography (MK RP-18e 25-2 mm), MS (ESI) m/z 239.9 [M+H]$^+$. $^1$H NMR (400 MHz, CDCl$_3$) δ 7.93 (t, J=1.2 Hz, 1H), 7.84 (d, J=2.4 Hz, 1H), 7.46 (d, J=9.6 Hz, 1H), 7.02 (dd,=2.4 Hz, J$_2$=9.6 Hz, 1H), 6.80 (d, J=8.8 Hz, 1H), 6.59 (d, J=2.4 Hz, 1H), 6.52 (dd, J$_1$=2.8 Hz, J$_2$=8.8 Hz, 1H), 6.47 (d, J=2.0 Hz, 1H).

Procedure for the Preparation of Compound 9d:

To a mixture of compound 9c (0.2 g, 1.0 eq.) and compound 1g (0.4152 g, 1.0 eq.) in MeCN (10 mL) was stirred at reflux for 2 hours. After completion, the mixture was concentrated to give compound 9d (0.32 g, 99% yield) as a yellow solid. LCMS: $R_t$=1.874 min in 10-80AB_4 min, chromatography (Xtimate C18 2.1*30 mm), MS (ESI) m/z=385.9 [M+H]$^+$. $^1$H NMR (400 MHz, CDCl$_3$) δ 8.71 (s, 1H), 8.44 (d, J=19.6 Hz, 1H), 8.14 (t, J=1.2 Hz, 1H), 7.90 (d, J=2.4 Hz, 1H), 7.79-7.71 (m, 2H), 7.63 (d, J=2.4 Hz, 1H), 7.56-7.51 (m, 1H), 7.27-7.22 (m, 1H), 7.04 (dd, J$_1$=9.6 Hz, J$_2$=2.0 Hz, 1H), 7.67 (d, J=8.8 Hz, 2H), 6.53 (d, J=1.6 Hz, 1H), 2.36 (s, 3H).

Procedure for the Preparation of Compound 9e:

To a solution of compound 9d (270 mg, 1.0 eq) and B (116 mg, 1.10 eq) in THF/DMF (20 mL, v/v=1:1), was added t-BuOK (326 mg, 4.1 eq). The mixture was stirred at 100° C. for 12 hours. After completion, the mixture was concentrated to give crude product and pre-purification by column chromatography on silica gel (dichloromethane:MeOH=20:1), then the crude was purified by reverse phase preparative HPLC to give 70 mg of compound 9e as pale solid (100 mg, 27.6% yield). LCMS: $R_t$=1.614 min in 10-80AB_4 min, chromatography (Xtimate C18 2.1*30 mm SN:3U411201583), MS (ESI) m/z=517.3 [M+H]$^+$. $^1$H NMR (400 MHz, CDCl$_3$) δ 10.01 (s, 1H), 8.65 (s, 1H), 8.07 (s, 1H), 8.13 (t, J=1.2 Hz, 1H), 7.89 (d, J=2.4 Hz, 1H), 7.71 (d, J=2.4 Hz, 1H), 7.69-7.60 (m, 3H), 7.51 (d, J=9.2 Hz, 1H), 7.04 (dd, J$_1$=2.4 Hz, J$_2$=9.6 Hz, 1H), 6.94 (d, J=8.8 Hz, 1H), 6.52 (d, J=2.0 Hz, 1H), 4.74-4.645 (m, 1H), 3.27-3.20 (m, 1H), 2.60-2.50 (m, 1H), 2.43 (s, 3H), 2.40-2.33 (m, 2H), 2.29 (s, 3H), 2.21-2.13 (m, 1H).

Procedure for the preparation of Compound 9:

Compound 9e (85 mg) was separated by SFC to give Compound 9 (39 mg) and Compound 9' (41 mg).

Compound 9 (enantiomer-1): LCMS: $R_t$=1.583 min in 10-80AB_4 min, chromatography (Xtimate C18, 2.1*30 mm, 3 um SN: 3U411201579), MS (ESI) m/z=517.1 [M+H]$^+$. $^1$H NMR (400 MHz, Methanol-d$_4$) δ 8.49 (s, 1H), 8.12 (t, J=1.2 Hz, 1H), 7.88 (d, J=2.4 Hz, 1H), 7.78-7.67 (m, 4H), 7.42 (d, J=8.0 Hz, 1H), 7.28 (d, J=8.4 Hz, 1H), 7.28 (d, J=8.0 Hz, 1H), 7.14 (dd, J$_1$=2.0 Hz, J$_2$=9.6 Hz, 1H), 7.00 (d, J=8.8 Hz, 1H), 6.61 (d, J=2.0 Hz, 1H), 5.15-5.05 (m, 1H), 3.29-3.23 (m, 1H), 2.95 (d, J=12.0 Hz, 1H), 2.68-2.58 (m, 1H), 2.49-2.40 (m, 2H), 2.40 (s, 3H), 2.33 (s, 3H), 2.10-2.02 (m, 1H).

Example 10

N$^4$-(4-([1,2,4]triazolo pyridin-7-yloxy)-3-methylphenyl)-5-((3,3-difluoro-1-methylpiperidin-4-yl)oxy)quinazoline-4,7-diamine

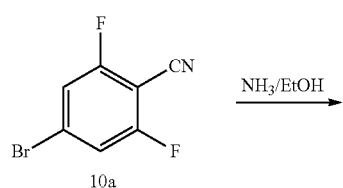

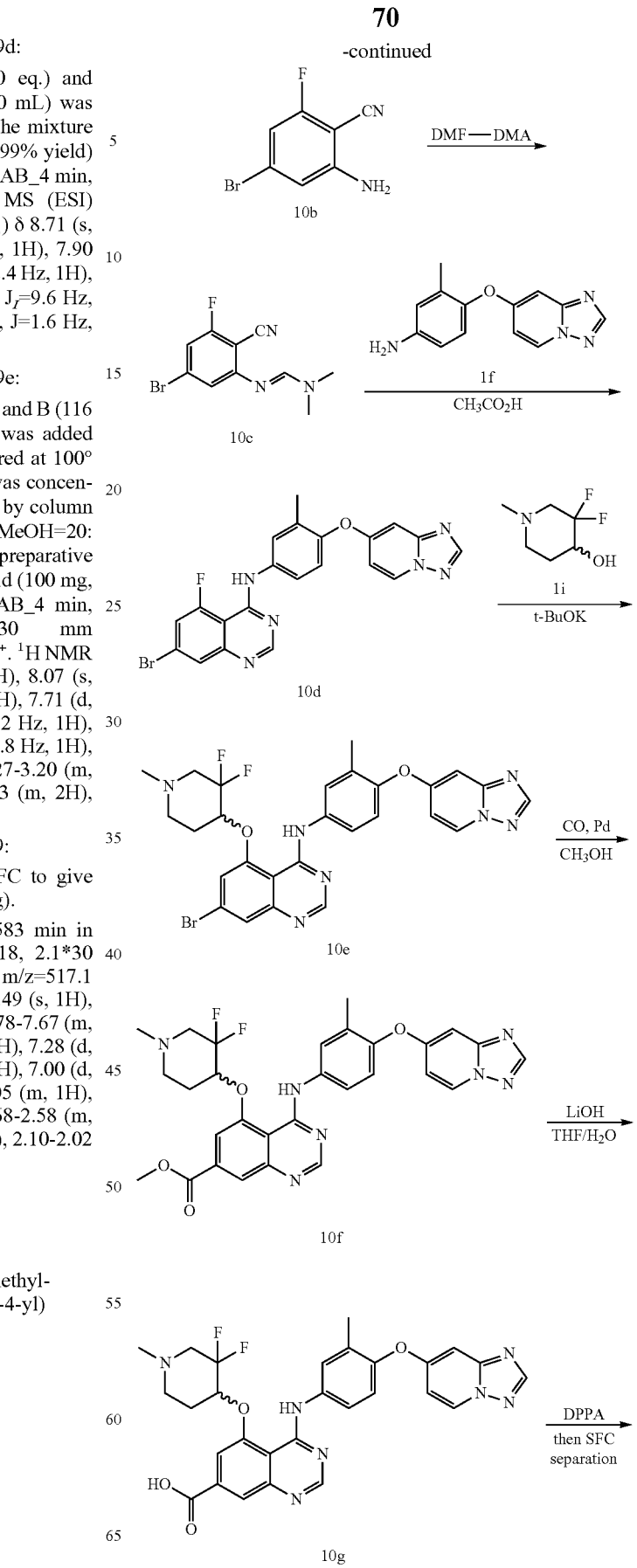

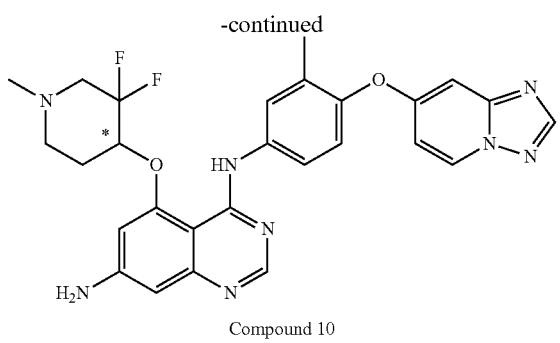

Compound 10

Procedure for the Preparation of Compound 10b:

To a mixture of compound 10a (20 g) in autoclave was added NH$_3$/EtOH (200 mL). The mixture was stirred at 100° C. overnight. The mixture was concentrated in vacuo and the residue was dissolved in ethyl acetate (200 mL) and washed with water (100 mL). The organic layer was concentrated to give a grey solid which was washed petroleum ether (3*100 mL) and dried to give compound 10b (19.5 g, 98% yield). $^1$H NMR (400 MHz, CDCl$_3$) δ 6.72 (t, J=1.2 Hz, 1H), 6.67 (dd, J$_1$=8.8 Hz, J$_2$=1.2 Hz. 1H), 4.63 (s, 2H).

Procedure for the Preparation of Compound 10c:

A solution of compound 10b (10.0 g) and DMF-DMA (11.0 g, 2.0 eq) in toluene was stirred at 120° C. for 2 h. The mixture was concentrated in vacuo to give compound 10c (15.2 g, crude) as grey solid which was used for next step directly. LCMS: R$_f$=0.718 min in 5-95AB_1.5 min chromatography (Welch Xtimate C18, 2.1*30 mm, 3 um), MS (ESI) m/z=271.2 [M+H]$^+$. $^1$H NMR (400 MHz, CDCl$_3$) δ 7.63 (s, 1H), 6.93-6.91 (m, 2H), 3.11 (d, J=2.0 Hz, 6H).

Procedure for the Preparation of Compound 10d:

A mixture of compound 10c (15.2 g) and compound 1f (11.1g, 1.0 eq) in acetic acid (150 mL) was stirred at 120° C. for 2 h. The strong desired Ms peak (466.9) has been detected by LCMS. The mixture was cooled and then poured into water (100 mL). The mixture was filtered, concentrated and purified by chromatography (DCM:MeOH=20:1 (v/v)) to give compound 10d (8.0 g, 38%) as a brown solid. LCMS: R$_f$=0.787 min in 5-95AB_1.5 min chromatography (Welch Xtimate C18, 2.1*30 mm, 3 um), MS (ESI) m/z=466.9 [M+H]$^+$. $^1$H NMR (400 MHz, DMSO-d$_6$) δ 9.28 (d, J=11.6 Hz, 1H), 8.93 (d, J=7.6 Hz, 1H), 8.59 (s, 1H), 8.38 (s, 1H), 7.85-7.67 (m, 4H), 7.21 (d, J=8.4 Hz, 1H), 7.02 (dd, J$_1$=7.6 Hz, J$_2$=2.8 Hz, 1H), 6.78 (d, J=2.8 Hz, 1H), 2.18 (s, 3H).

Procedure for the Preparation of Compound 10e:

A mixture of compound 10d (4.6 g), comound 1i (1.5 g, 1.0 eq) and t-BuOK (2.2 g, 2.0eq) in THF (50 mL) and DMF (20 mL) was stirred at 70° C. overnight. The mixture was poured into water (50 mL), and then filtered. The solid was dried to give compound 10e (4.74 g, 80% yield) as a grey solid. LCMS: R$_f$=0.737 min in 5-95AB_1.5 min chromatography (Welch Xtimate C18, 2.1*30 mm, 3 um), MS (ESI) m/z=597.9 [M+H]$^+$. $^1$H NMR (400 MHz, DMSO-d$_6$) δ 9.95 (s, 1H), 8.92 (d, J=7.6 Hz, 1H), 8.59 (s, 1H), 8.37 (s, 1H), 7.83 (d, J=2.4 Hz, 1H), 7.73 (dd, J$_1$=8.8 Hz, J$_2$=2.4 Hz, 1H), 7.64 (s, 2H), 7.25 (d, J=8.8 Hz, 1H), 7.02 (dd, J$_1$=7.6 Hz, J$_2$=2.4 Hz, 1H), 6.82 (d, J=2.4 Hz, 1H), 5.43-5.35 (m, 1H), 3.27-3.23 (m, 2H), 2.86-2.82 (m, 1H), 2.38-2.32 (m, 2H), 2.29 (s, 3H), 2.19 (s, 3H), 1.97-1.89 (m, 1H).

Procedure for the Preparation of Compound 10f:

A mixture of compound 10e (200 mg), Pd(OAc)$_2$ (8 mg, 0.1 eq), dppf (18 mg, 0.1 eq) and Et$_3$N (67 mg, 2.0 eq) in methanol (10 mL) was stirred at 70° C. under carbon monoxide atmosphere (45 Psi) overnight. The mixture was then filtered and the filtrate was concentrated to give compound 10f (223 mg, crude) as a brown oil. LCMS: R$_f$=0.730 min in 5-95AB_1.5 min chromatography (Welch Xtimate C18, 2.1*30 mm, 3 um), MS (ESI) m/z=576.1 [M+H]$^+$.

Procedure for the Preparation of Compound 10g:

A solution of compound 10f (223 mg) and LiOH—H$_2$O (70 mg, 5.0 eq) in THF/H$_2$O (5 mL) was stirred at room temperature overnight. The mixture was concentrated and the residue was acidified with a solution of 1N HCl. The precipitate was collected and dried to give comound 10g (140 mg, crude) as a grey solid. LCMS: R$_f$=0.643 min in 5-95AB_1.5 min chromatography (Welch Xtimate C18, 2.1*30 mm, 3 um), MS (ESI) m/z=562.1 [M+H]$^+$.

Procedure for the Preparation of Compound 10:

A solution of comound 10g (70 mg), DPPA (42 mg, 1.2 eq) and Et$_3$N (25 mg, 2.0 eq) in t-BuOH (3 mL) was stirred at 80° C. overnight. The mixture was concentrated in vacuo and the residue was treated with HCl/dioxane (4M, 1 mL). The reaction was stirred at room temperature for 10 min. The mixture was concentrated and the residue was purified by pre-HPLC (column: Sunfire C8 30*100 mm*5 um, gradient: 15-25% B (A=water/0.05% HCl, B=acetonitrile), flow rate: 30 mL/min) followed by SFC separation to give enantiomer Compound 10 (7.9 mg, 10% yield). LCMS: R$_f$=1.427 min in 10-80AB_4 min chromatography (Welch Xtimate C18, 2.1*30 mm, 3 um), MS (ESI) m/z=533.0 [M+H]$^+$. $^1$H NMR (400 MHz, Methanol-d$_4$) δ 9.06 (d, J=7.6 Hz, 1H), 9.00 (s, 1H), 8.51 (s, 1H), 7.79-7.74 (m, 2H), 7.42 (d, J=6.8 Hz, 1H), 7.30 (d, J=8.8 Hz, 1H), 6.97 (s, 1H), 6.49 (d, J=1.2 Hz, 1H), 5.65-5.58 (m, 1H), 4.27 (m, 2H), 4.06-3.94 (m,1H), 3.80-3.65 (m, 2H), 3.09 (s, 3H), 2.88-2.86 (m, 2H), 2.44-2.41 (m, 2H), 2.27 (s, 3H).

Example 11

5-(((3S,4R)-3-fluoro-1-methylpiperidin-4-yl)oxy)-N-(4-(imidazo[1,2-a]pyridin-7-yloxy)-3-methylphenyl) quinazolin-4-amine

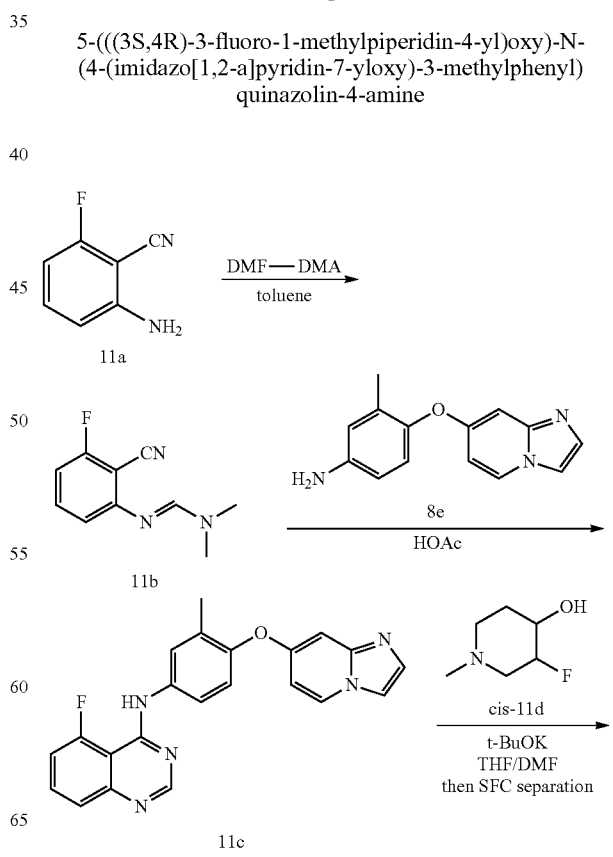

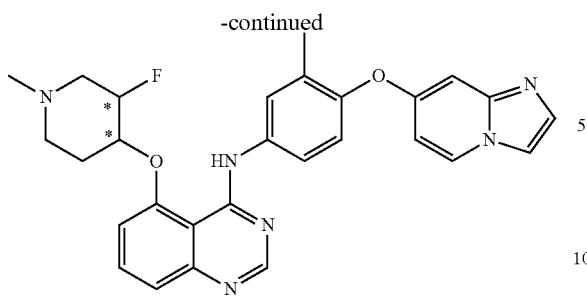

Compound 11: *enantiomerically pure cis isomer

Procedure for the Preparation of Compound 11b:

DMF-DMA (3.93 mL, 29.38 mmol, 2.0 eq.) was added to a solution of comound 11a (2 g, 14.69 mmol) in toluene (20 mL). The resulting suspension was stirred at 120° C. for 1.5 hours. LCMS analysis showed the reaction was completed. The solution was concentrated to afford comound 11b (3.0 g, crude, 93% purity) as a yellow solid. LCMS: $R_t$=0.135 min in 5-95AB_220&254 chromatography, MS (ESI) m/z=191.9 [M+H]$^+$.

Procedure for the Preparation of Compound 11c:

To a solution comound 11b (1.5 g, 93% purity, 7.30 mmol, 1.0 eq.) in acetic acid (30 mL) was added compound 8e (2.62 g, 10.94 mmol, 1.5 eq.), the reaction mixture was heated to 120° C. for 2 hours. LCMS showed the reaction was completed. The acetic acid was removed in vacuo and the crude product was dissolved in acetonitrile (20 mL) and diluted with water (50 mL). The solution was basified by sodium carbonate solution to pH=8. The precipitate was filtered and filter cake was washed with ethyl acetate, dried over sodium sulfate and concentrated to afford compound 11c (1.5 g, crude). LCMS: $R_t$=0.609 min in 5-95AB_1.5 min chromatography, MS (ESI) m/z=386.1 [M+H]$^+$. $^1$H NMR (400 MHz, DMSO-d$_6$) δ 2.20 (3H, s), 6.55 (1H, d, J=2.4 Hz), 6.82 (1H, dd, J$_1$=7.2 Hz, J$_2$=2.4 Hz), 7.15 (1H, d, J=8.4 Hz), 7.40-7.48 (2H, m), 7.61-7.74 (3H, m), 7.81-7.89 (2H, m), 8.56 (1H, d, J=7.6 Hz), 8.58 (1H, s), 9.20 (1H, br.s)

Procedure for the Preparation of Compound 11 cis-isomer:

To a solution of compound !!c (300 mg, 1.0 eq) and compound cis-11d (207 mg, 2.0 eq) in THF/DMF (20 mL, v/v 1:1) was added t-BuOK (306 mg, 3.5 eq). The mixture was stirred at 100° C. for 72 hours. After completion, the reaction was concentrated and the residue was purified by column chromatography on silica gel with DCM/MeOH (10:1) to give crude which was further purified by pre-HPLC followed by SFC separation to give enantiomerically pure cis-isomer Compound 11 as a white solid (35 mg, 9% yield). LCMS: $R_t$=1.560 min in 0-60AB_4 min, chromatography (Xtimate C18, 2.1*30 mm, 3 um SN:3U411201579), MS (ESI) m/z=499.0 [M+H]$^+$. $^1$H NMR (400 MHz, D$_2$O) δ 8.65 (s, 1H), 8.63 (d, J=7.6 Hz, 1H), 8.05 (t, J=8.4 Hz, 1H), 7.93 (d, J=2.0 Hz, 1H), 7.73 (d, J=2.4 Hz, 1H), 7.70 (d, J=2.4 Hz, 1H), 7.63-7.59 (m, 1H), 7.52 (d, J=8.4 Hz, 1H), 7.49 (d, J=8.4 Hz, 1H), 7.34 (d, J=8.8 Hz, 1H), 7.30 (dd, J=7.6 Hz, 2.4 Hz, 1H), 7.05 (d, J=2.8 Hz, 1H), 5.65-5.53 (m, 1H), 5.44-5.30 (m, 1H), 4.11-4.04 (m, 1H), 3.78-3.74 (m, 1H), 3.71-7.57 (m, 1H), 3.45-3.38 (m, 1H), 3.01 (s, 3H), 2.67-2.64 (m, 1H), 2.49-2.37 (m, 1H), 2.24 (s, 3H).

Example 12

(S)—N-(4-([1,2,4]triazolo[1,5-a]pyridin-7-yloxy)-3-methylphenyl)-5-((1-ethyl-3,3-difluoropiperidin-4-yl)oxy)quinazolin-4-amine And (R)—N-(4-([1,2,4]triazolo[1,5-a]pyridin-7-yloxy)-3-methylphenyl)-5-((1-ethyl-3,3-difluoropiperidin-4-yl)oxy)quinazolin-4-amine

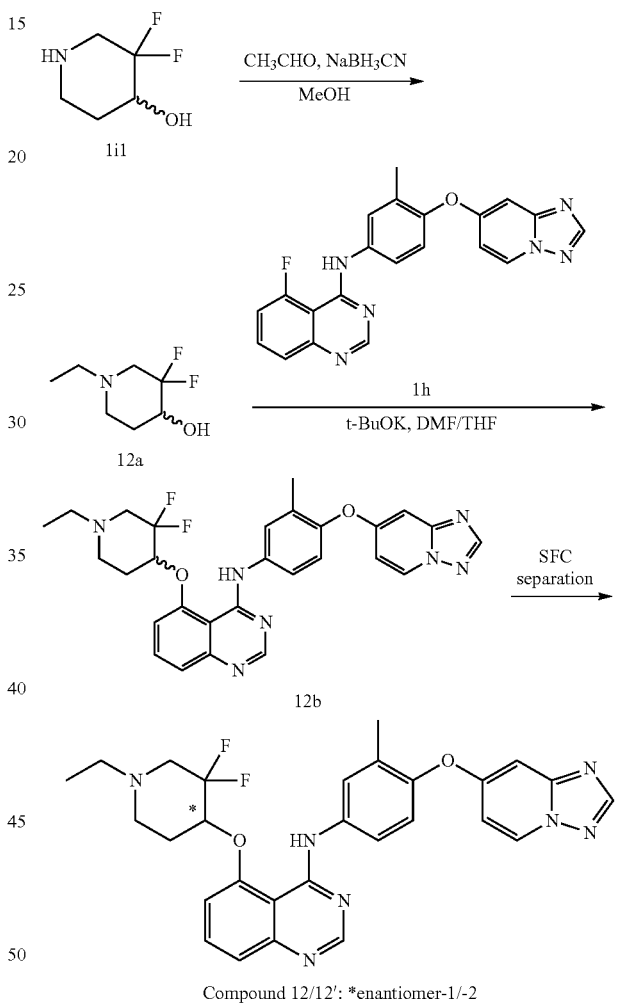

Compound 12/12′: *enantiomer-1/-2

Procedure for the Preparation of Compound 12a:

To a solution of comound 1i1 (0.2 g, 1.46 mmol) in MeOH (8 mL) was added sodium cyanoborohydride (0.092 g, 1.46 mmol) and acetaldehyde (0.099 mL, 1.75 mmol). The resulting mixture was stirred at 12-23° C. for 16 hours. The reaction was then poured into water (15 mL), extracted with chloroform/isopropanol (v/v=3/1, 10 mL×3). The combined organic layers were dried over Na$_2$SO$_4$, filtered and concentrated under reduce pressure to give crude compound 12a (0.22 g) as a yellow oil. The product was used in the next step directly without further purification. $^1$H NMR (400 MHz, CDCl$_3$) δ 1.09 (3H, t, J=7.2 Hz), 1.75-2.04 (4H, m), 2.75-2.85 (1H, m), 2.45-2.05 (2H, m), 2.53-2.67 (2.5H, m), 2.75-2.92 (2H, m), 3.69-3.85 (2H, m), 4.02-4.05 (1H, m).

Procedure for the Preparation of Compound 12b:

To a solution of comound 1h (300 mg, 0.776 mmol) in DMF (10 mL) and THF (4 mL) was added potassium tert-butoxide (305 mg, 2.72 mmol) and compound 12a (154 mg, 0.931 mmol). The resulting mixture was stirred at 100° C. for 16 hours. The reaction was then poured into water (30 mL) and extracted with ethyl acetate (20 mL×3). The combined organic layers were washed with brine (80 mL), dried over sodium sulfate and concentrated to give a residue which was purified by prep-HPLC (column: YMC-Actus Triart C18 150*30 5 u, gradient: 5-35 B (A=water/0.05% HCl, B=acetonitrile), flow rate: 25 mL/min) and lyophilized to give compound 12b (110 mg, crude) as a yellow solid. LCMS: $R_f$=1.972 min in 4.0 min chromatography, MS (ESI) m/z=532.3 [M+H]$^+$.

Procedure for the Preparation of Compound 12/12': Enantiomer-1/-2

Compound 12b (110 mg) was separated by preparative chiral-HPLC on a AD (250 mm*30 mm, 5 um) column, Mobile phase: A: $CO_2$, B: ethanol (0.05% DEA), Condition: Base-ETOH, Begin B 40% and End B 40%, Flow Rate (mL/min)=50. The fractions containing the desired compound were evaporated to dryness to afford enantioisomer 1 and enantioisomer 2, then re-purified by prep-HPLC (DuraShell 150*25 mm*5 um, 35%-65% B (A=water/10 mM NH$_4$Ac, B=MeCN). Most of MeCN was removed under reduced pressure, the remaining solvent was removed by lyophilization to afford Compound 12' (24.6 mg, yield: 5.96%) as a white solid and Compound 12 (27.6 mg, yield: 6.69%) as a white solid. Compound 12' (enantiomer-2): LCMS: $R_f$=1.903 min in 4.0 min chromatography, MS (ESI) m/z 532.3 [M+H]$^+$. $^1$H NMR (400 MHz, Methanol-d$_4$) δ 1.14 (3H, t, J=7.2 Hz), 2.07-2.09 (1H, m), 2.25 (3H, s), 2.44-2.65 (5H, m), 3.04 (1H, d, J=12.4 Hz), 3.34-3.39 (1H, m), 5.07-5.16 (1H, m), 6.81 (1H, d, J=2.4 Hz), 7.06 (1H, dd, J=7.6, 2.4 Hz), 7.18 (1H, d, J=8.8 Hz), 7.31 (1H, d, J=8.0 Hz), 7.45 (1H, d, J=8.0 Hz), 7.76-7.88 (3H, m), 8.28 (1H, s), 8.54 (1H, s), 8.73 (1H, d, J=8.0 Hz).

Compound 12 (enantiomer-1): LCMS: $R_f$=1.905 min in 4.0 min chromatography, MS (ESI) m/z 532.2 [M+H]$^+$. $^1$H NMR (400 MHz, Methanol-d$_4$) δ 1.14 (3H, t, J=7.2 Hz), 2.04-2.07 (1H, m), 2.25 (3H, s), 2.40-2.65 (5H, m), 3.04 (1H, d, J=12.4 Hz), 3.34-3.39 (1H, m), 5.07-5.16 (1H, m), 6.81 (1H, d, J=2.4 Hz), 7.06 (1H, dd, J=10.0, 2.4 Hz), 7.18 (1H, d, J=8.8 Hz), 7.31 (1H, d, J=8.0 Hz), 7.45 (1H, d, J=7.6 Hz), 7.76-7.88 (3H, m), 8.28 (1H, s), 8.54 (1H, s), 8.73 (1H, d, J=7.6 Hz).

Example 13

N-(4-(imidazo[1,2-a]pyridin-7-yloxy)-3-methylphenyl)-5-(quinuclidin-4-yloxy)quinazolin-4-amine

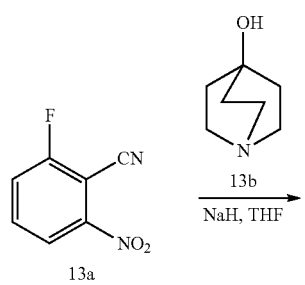

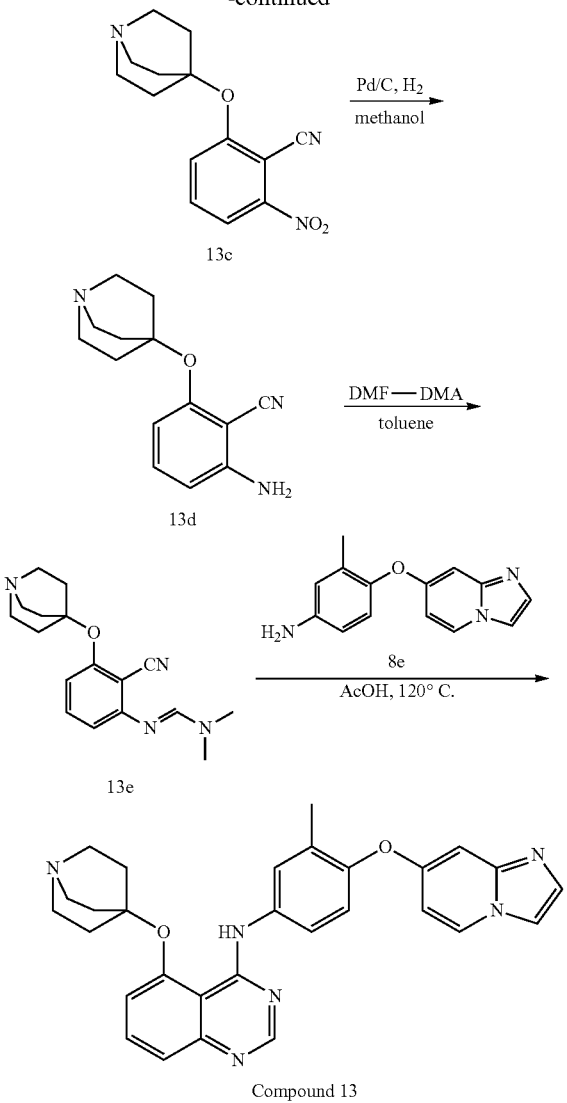

Procedure for the Preparation of Compound 13c:

NaH (87 mg, 60% Wt, 2.17 mmol) was added portionwise to compound 13b (230 mg, 1.81 mmol) and compound 13a (300 mg, 1.81 mmol) in THF (5 mL) at 0° C. over a period of 5 minutes under nitrogen. The resulting mixture was stirred at 17-27° C. for 3 hours. The reaction mixture was then poured into saturated NH$_4$Cl (75 mL), extracted with EtOAc (50 mL×2), the organic layers were dried over Na$_2$SO$_4$, filtered and evaporated to afford crude product which was purified by flash silica chromatography (PE: EA=3:1 to 100% methanol). Pure fractions were evaporated to dryness to afford compound 13b (320 mg, crude) as a yellow solid. LCMS: $R_f$=0.579 min in 1.5 min chromatography, MS (ESI) m/z=274.0 [M+H]$^+$. $^1$H NMR (400 MHz, CDCl$_3$) δ 1.95-2.01 (6H, m), 3.08-3.12 (6H, m), 7.49 (1H, d, J=8.4 Hz), 7.67 (1H, t, J=8.4 Hz), 7.99 (1H, d, J=8.4 Hz).

Procedure for the Preparation of Compound 13d:

Compound 13c (320 mg, 1.17 mmol) and Pd—C (120 mg, 10% Wt, 0.11 mmol) in methanol (30 mL) were stirred under an atmosphere of hydrogen balloon at 17-24° C. for 1 hour. The reaction mixture was then filtered off and the filtrate was evaporated to dryness to afford compound 13d (280 mg, 98% yield) as pale yellow oil which was solidified on standing. LCMS: $R_t$=0.279 min in 1.5 min chromatography, MS (ESI) m/z=244.2 [M+H]⁺. ¹H NMR (400 MHz, CDCl₃) δ 1.90-1.94 (6H, m), 3.02-3.06 (6H, m), 4.42 (2H, br.s.), 6.39 (1H, d, J=8.0 Hz), 6.43 (1H, d, J=8.4 Hz), 7.18 (1H, t, J=8.0 Hz).

Procedure for the Preparation of Compound 13e:

1,1-dimethoxy-N,N-dimethylmethanamine (0.339 mL, 2.53 mmol) was added to compound 13d (280 mg, 1.15 mmol) in toluene (10 mL) at 20° C. The resulting mixture was stirred at 110° C. for 90 minutes. The reaction mixture was concentrated to give a crude product which was used in the next step directly without further purification. LCMS: $R_t$=0.128 min in 1.5 min chromatography, MS (ESI) m/z=299.1 [M+H]⁺.

Procedure for the preparation of Compound 13:

Compound 8e (164 mg, 0.68 mmol) was added to compound 13e (170 mg, 0.57 mmol) in AcOH (5 mL) at 20° C. The resulting mixture was stirred at 120° C. for 90 minutes. The reaction mixture was then concentrated to give crude product which was purified by preparative HPLC (column: Waters Xbridge Prep OBD C18 150*30 5 u, 25-55% B (A=water/0.05% ammonia, B=acetonitrile), flow rate: 25 mL/min). Fractions containing the desired compound were dried by lyophilization to afford Compound 13 (95.3 mg, 33.9% yield) as a white solid. LCMS: $t_R$=0.578 min in 1.5 min chromatography, MS (ESI) m/z=493.2 [M+H]⁺. LCMS: $t_R$=2.740 min in 4.0 min chromatography, MS (ESI) m/z=493.2 [M+H]⁺. ¹H NMR (400 MHz, CDCl₃) δ 2.01-2.05 (6H, m), 2.26 (3H, s), 3.07-3.11 (6H, m), 6.72-6.76 (2H, m), 7.08 (1H, d, J=8.4 Hz), 7.16 (1H, d, J=7.2 Hz), 7.49 (1H, d, J=10.4 Hz), 7.58-7.65 (3H, m), 7.80 (1H, d, J=2.0 Hz), 8.05 (1H, d, J=7.2 Hz), 8.66 (1H, s), 10.22 (1H, s).

Example 14

(S)—N-(4-([1,2,4]triazolo[1,5-a]pyridin-7-yloxy)-2-fluoro-5-methylphenyl)-5-((3,3-difluoro-1-methylpiperidin-4-yl)oxy)-7-methoxyquinazolin-4-amine And (R)—N-(4-([1,2,4]triazolo[1,5-a]pyridin-7-yloxy)-2-fluoro-5-methylphenyl)-5-((3,3-difluoro-1-methylpiperidin-4-yl)oxy)-7-methoxyquinazolin-4-amine

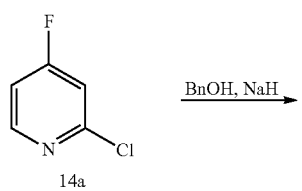

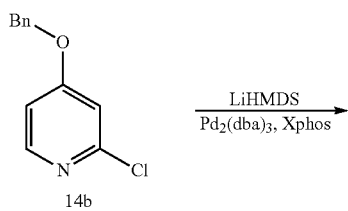

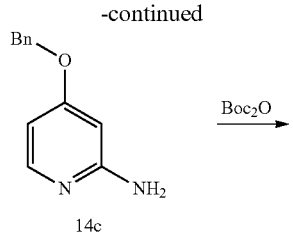

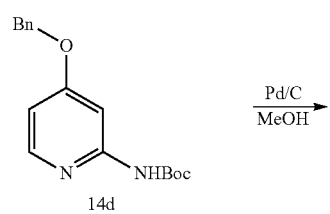

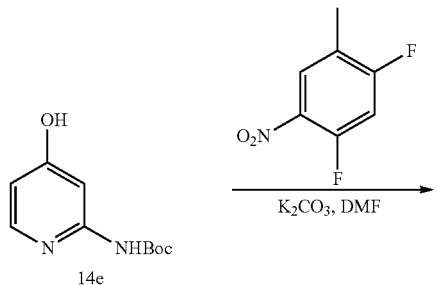

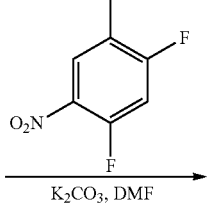

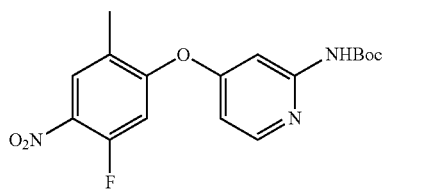

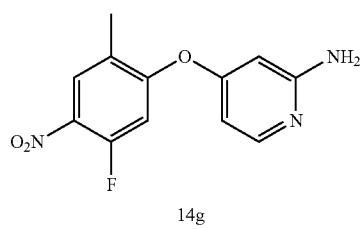

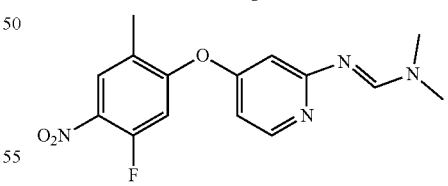

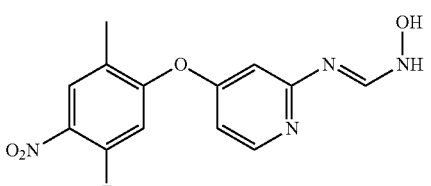

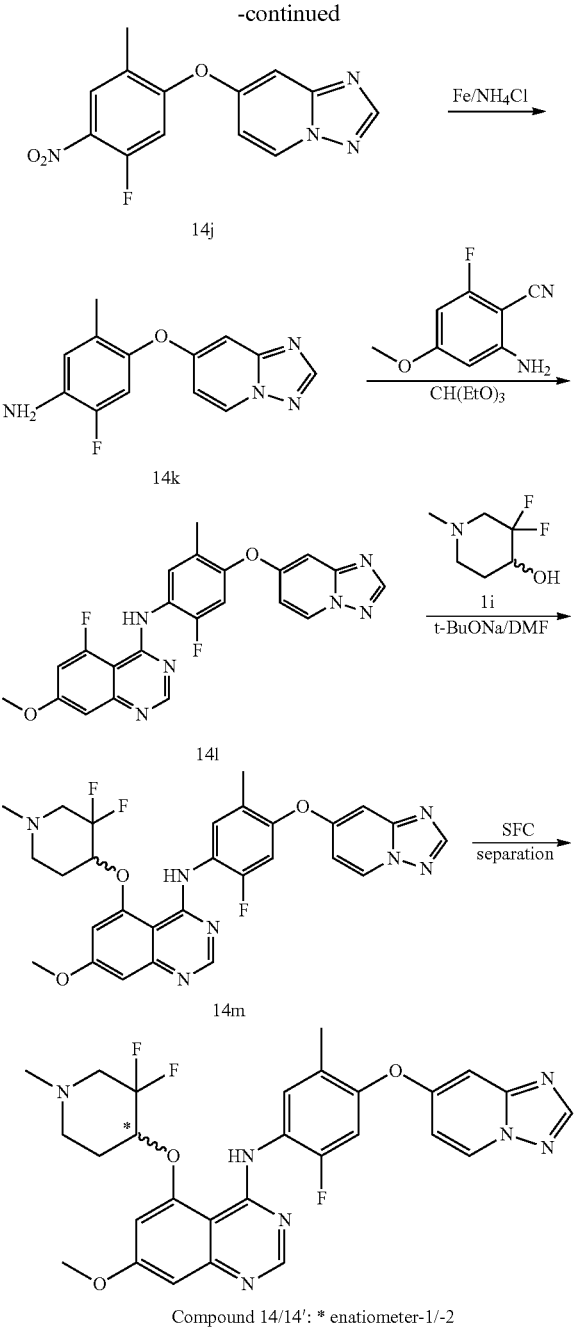

Compound 14/14': * enatiometer-1/-2

Procedure for the Preparation of Compound 14b:
To a solution of benzyl alcohol (10 g, 76 mmol) in dioxane (150 mL) was added NaH (3.3 g, 1.1eq), and the solution was stirred at 60° C. for 2.0 h. Then compound 14a (8.2 g, 76 mmol) was added to the reaction mixture and stirred at reflux for 3.0 hrs. After completion, the reaction solution was then quenched with $NH_4Cl$, extracted with EtOAc. The combined organic layers were concentrated and the residue was recrystallized by PE/EtOAc=10/1 (20 ml) to give the product (14 g, yield 84.1%) as a white solid. $^1H$ NMR (400 MHz, $CDCl_3$) δ 8.20 (d, J=6.0 Hz, 1H), 7.44-7.37 (m, 5H), 6.92 (d, J=2.0 Hz, 1H), 6.82 (dd, J=5.6 Hz, 2.4 Hz, 1H), 5.11 (s, 2H).

Procedure for the Preparation of Compound 14c:
To a mixture of compound 14b (12 g, 5.01 mmol), $Pd_2(dba)_3$ (550 mg, 0.5 mmol) and Xphos (525 mg, 1.1 mmol) in THF (120 mL) was added LiHMDS (66.0 mL, 66 mmol). After heating to 65° C. for 60 mins, the mixture was cooled down to room temperature. After completion, the reaction was quenched with aqueous HCl (2.0 mL, 1.0 mol/L) and extracted with ethyl acetate. The liquid solution was adjusted to pH>8 by aqueous $NaHCO_3$, extracted with EtOAc (200 mL×2). The combined organic layer was concentrated to give the compound 14c (10.5 g, yield 88%) as a white solid. $^1H$ NMR (400 MHz, $CDCl_3$) δ 7.91 (d, J=6.0 Hz, 1H), 7.41-7.33 (m, 5H), 6.34 (dd, J=6.0 Hz, 2.0 Hz, 1H), 6.05 (d, J=2.4 Hz, 1H), 5.05 (s, 2H), 4.38 (s, 2H).

Procedure for the Preparation of Compound 14d:
To a mixture of compound 14c (10.5 g, 52.5 mmol) in t-BuOH (50 mL) was added $Boc_2O$ (12.6 g, 1.1 eq), then the solution was stirred at 50° C. for 2.0 h. After completion, EtOH (300 mL) was added to the reaction solution. The mixture was cooled down to room temperature, filtered and concentrated to give the product (16 g, 95.2% yield). LCMS $R_t$=0.946 min in 10-80AB_2.0 min chromatography, (Welch Xtimate C18 2.1*30 mm), MS (ESI) m/z=300.9 [M+H]$^+$.

Procedure for the Preparation of Compound 14e:
A solution of compound 14d (15 g, 50 mmol) in MeOH (300 mL) was added Pd/C (3.0 g). The solution was stirred at room temperature for 3.0 h. The reaction solution was then filtered and the filtrate was concentrated to give the compound 14e (8.5 g, 80.9% yield) as a white solid without further purification.

Procedure for the Preparation of Compound 14f:
A solution of compound 14e (5.0 g, 28.9 mmol) and 1,5-difluoro-2-methyl-4-nitrobenzene (6.06 g, 28.9 mmol) in DMF (100 mL) was added $K_2CO_3$ (5.9 g, 43.4 mmol) and the solution was stirred at room temperature overnight. The mixture was concentrated and the residue was purified by silica gel column (PE/EtOAc=1/2) to give the compound 14f (6.5 g, yield 61.9%) as a yellow solid. $^1H$ NMR (400 MHz, $CDCl_3$) δ 8.24 (d, J=5.6 Hz, 1H), 8.06 (d, J=8.0 Hz, 1H), 8.00 (s, 1H), 7.86 (s, 1H), 6.79-6.82 (d, J=11.6 Hz, 1H), 6.57 (m, 1H), 2.30 (s, 3H), 1.50 (s, 9H).

Procedure for the Preparation of Compound 14g:
A solution of compound 14f (6.5 g, 17.9 mmol) in DCM (40 mL) was added TFA (15 mL), and the solution was stirred at reflux for 3.0 h. TLC showed starting material was consumed. LCMS showed the product was found. The mixture was concentrated and the residue was washed with aq.$NaHCO_3$, extracted with DCM. The combined organic layer was concentrated to give the compound 14g (4.5 g, 95%) as yellow oil which was used in the next step directly.

Procedure for the Preparation of Compound 14h:
A solution of compound 14g (4.5 g, 13.8 mmol) in DMF-DMA (20.0 mL) was stirred at reflux for 3.0 h. The mixture was concentrated to give the compound 14h (6.2 g, crude) as yellow oil which used directly for next step. LCMS: $R_t$=2.579 min in 0-60AB_4 min chromatography, (Welch Xtimate C18 2.1*30 mm), MS (ESI) m/z=319.0 [M+H]$^+$.

Procedure for the Preparation of Compound 14i:
A solution of compound 14h (6.3 g, 13.8 mmol) in i-PrOH (50.0 mL) was added $NH_2OH.HCl$ (1.3 g, 13.8 mmol), and the solution was stirred at room temperature for 4.0 h. The mixture was filtered to give the compound 14i (5.5 g, crude) as a yellow solid which used directly for next step. LCMS: $R_t$=0.767 min in 5-95AB_1.5 min chromatography, (Welch Xtimate C18 2.1*30 mm), MS (ESI) m/z=307.0 [M+H]$^+$.

Procedure for the Preparation of Compound 14j:
A solution of compound 14i (5.0 g, 13.0 mmol) in THF (50.0 mL) was added TFAA (4.5 g, 16.9 mmol), and the solution was stirred at 50° C. overnight. The mixture was adjusted with NaHCO₃ to pH>8, extracted with ethyl acetate. The combined organic layer was concentrated and the residue was purified by silica gel column to give the compound 14j (2.1 g, crude) as a yellow solid.

Procedure for the Preparation of Compound 14k:

A solution of compound 14j (3.0 g, 10.4 mmol) in EtOH (100 mL) and H₂O (50 mL) was added Fe (2.9 g, 52 mmol) and NH₄Cl (3.2 g, 63 mmol), and the solution was stirred at reflux for 3.0 h. The reaction solution was filtered and the filtrate was concentrated to give the crude product which was purified by prep-HPLC (column: AD (250×30 mm, 5 um): 5-25% B (A=45% MeOH NH₃H₂O water, B=acetonitrile), flow rate: 50 mL/min, UV Detector 220 nm) to afford compound 14k (700 mg, yield 19.7%) as a white solid. ¹H NMR (400 MHz, CDCl₃) δ 8.47 (d, J=7.6 Hz, 1H), 8.21 (s, 1H), 6.85-6.83 (m, 1H), 6.79-6.71 (m, 3H), 3.71 (s, 2H), 2.06 (s, 3H).

Procedure for the Preparation of Compound 14l:

A solution of compound 14k (400 mg, 1.55 mmol) in i-PrOH (5.0 mL) was added triethoxymethane (690 mg, 4.65 mmol). The solution was stirred at 100° C. for 1.0 h and then 2-amino-6-fluoro-4-methoxybenzonitrile (260 mg, 1.55 mmol) and TFA (0.2 mL) was added to the reaction solution, and the solution was stirred at reflux for 2.0 h. The reaction solution was concentrated and the residue was washed by PE/EtOAc (v/v=10/1, 3.0 mL) to give compound 14l (400 mg, crude) as a yellow solid which used directly in the next step directly. LCMS: R₇=0.753 min in 5-95AB_1.5 min chromatography, (Welch Xtimate C18 2.1*30 mm), MS (ESI) m/z=434.9 [M+H]⁺.

Procedure for the Preparation of Compound 14m:

To a solution of compound 14l (400 mg, 0.92 mmol) in DMF (5.0 mL) was added t-BuONa (260 mg, 2.76 mmol) and comound 1i (280 mg, 1.84 mmol), and the solution was stirred at 120° C. for 2.0 h. The reaction solution was filtered and the filtrate was concentrated. The residue was purified by pre-HPLC (column: YMC-Triat, 10-30% B (A=TFA water, B=acetonitrile), flow rate: 30 mL/min, UV Detector 220 nm) to afford 14m (202 mg, yield 38.7%) as a white solid. LCMS: R₇=1.004 min in 0-60AB_2.0 min chromatography, (Welch MK RP-18e, 25-2 mm SN:UM8505/155), MS (ESI) m/z=566.1 [M+H]⁺. ¹H NMR (400 MHz, MeOH-d₄) δ 9.15 (d, J=10.0 Hz, 1H), 9.13 (s, 1H), 8.83 (s, 1H), 8.27 (d, J=8.4 Hz, 1H), 7.51 (dd, J=7.6 Hz, 2.8 Hz, 1H), 7.40-7.33 (m, 3H), 7.03 (s, 1H), 5.78 (m, 1H), 4.27 (m, 1H), 4.11 (s, 3H), 4.02-3.91 (m, 1H), 3.83-3.80 (m, 1H), 3.63-3.57 (m, 1H), 3.11 (s, 3H), 2.83 (m, 1H), 2.52 (m, 1H), 2.30 (s, 3H).

Procedure for the preparation of Compound 14:

Compound 14m (150 mg, 0.265 mmol) was seperated by SFC to give the product Compound 14' (55 mg, yield 36.7%) as a white solid and Compound 14 (54 mg, yield 36%) as a white solid.

Compound 14' (Enantiomer-2):

LCMS R₇=0.672 min in 5-95AB_1.5 min chromatography, (Welch MK RP-18e, 25-2 mm SNUM8505/155), MS (ESI) m/z=566.2[M+H]⁺. ¹H NMR (400 MHz, MeOH-d₄) δ 8.78 (d, J=7.2 Hz, 1H), 8.48 (s, 1H), 8.33 (s, 1H), 8.27 (d, J=8.8 Hz, 1H), 7.15 (d, J=11.2 Hz, 1H), 7.10 (dd, J=7.6 Hz, 2.0 Hz, 1H), 6.99 (s, 1H), 6.94 (s, 1H), 6.90 (s, 1H), 5.21-5.13 (m, 1H), 3.99 (s, 3H), 3.22-3.17 (m, 1H), 2.96-2.93 (m, 1H), 2.72-2.62 (m, 1H), 2.52-2.46 (m, 2H), 2.41 (s, 3H), 2.24 (s, 3H), 2.17-2.13 (m, 1H).

Compound 14 (Enantiomer-1):

LCMS: R₇=0.675 min in 5-95AB_1.5 min chromatography, (Welch MK RP-18e, 25-2 mm SNUM8505/155), MS (ESI) m/z=566.2[M+H]⁺. ¹H NMR (400 MHz, MeOH-d₄) δ 8.78 (d, J=7.2 Hz, 1H), 8.47 (s, 1H), 8.33 (s, 1H), 8.27 (d, J=8.8 Hz, 1H), 7.15 (d, J=10.4 Hz, 1H), 7.10 (dd, J=7.6 Hz, 2.0 Hz, 1H), 6.97 (s, 1H), 6.94 (d, J=2.8 Hz, 1H), 6.90 (d, J=2.0 Hz, 1H), 5.17-5.09 (m, 1H), 3.99 (s, 3H), 3.20-3.15 (m, 1H), 2.94-2.91 (m, 1H), 2.69-2.59 (m, 1H), 2.49-2.43 (m, 2H), 2.40 (s, 3H), 2.25 (s, 3H), 2.17-2.13 (m, 1H).

Example 15

(±)-(5-(((2S,4S)-2-(difluoromethyl)piperidin-4-yl)oxy)-N-(4-(imidazo[1,2-a]pyridin-7-yloxy)-3-methylphenyl)quinazolin-4-amine And (±)-(5-(((2R,4S)-2-(difluoromethyl)piperidin-4-yl)oxy)-N-(4-(imidazo[1,2-a]pyridin-7-yloxy)-3-methylphenyl)quinazolin-4-amine

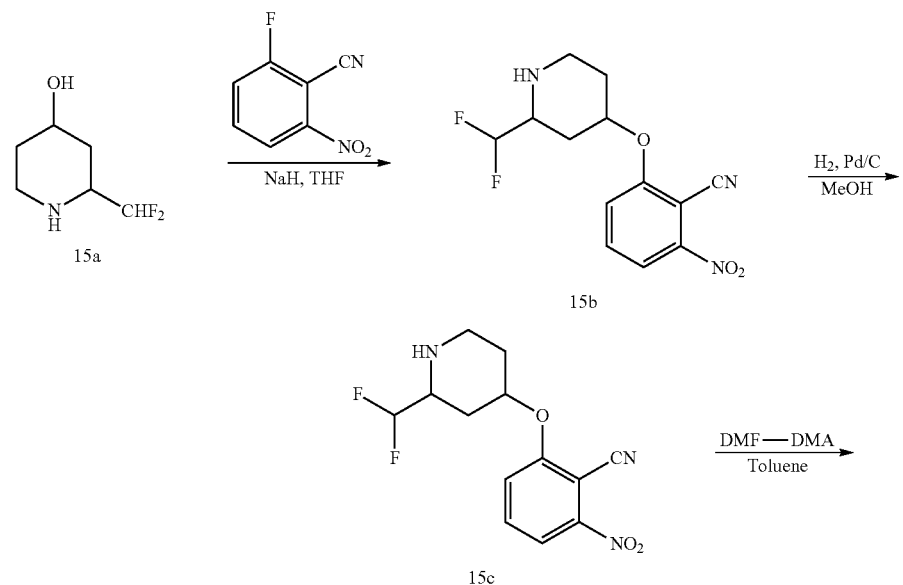

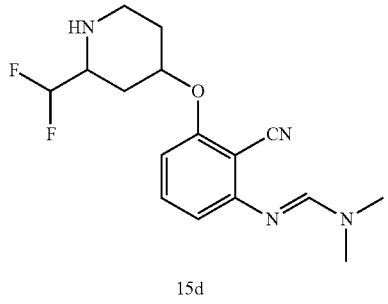

15d

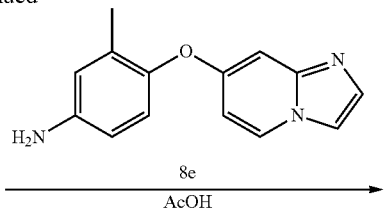

8e
AcOH

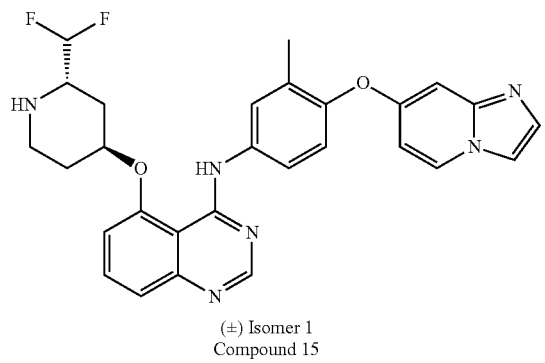

(±) Isomer 1
Compound 15

+

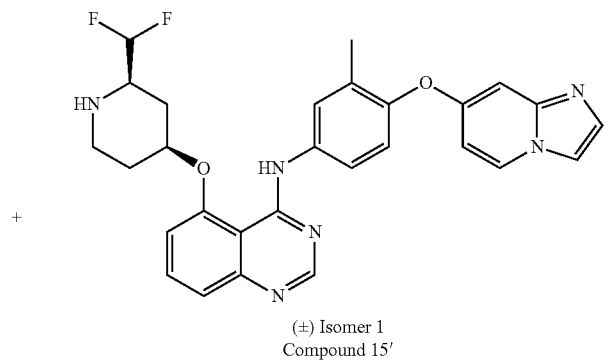

(±) Isomer 1
Compound 15'

Procedure for the Preparation of Compound 15b:

To a solution of compound 15a (0.271 g, 1.44 mmol) in THF (10 mL) was added NaH (0.241 g, 6.02 mmol, 60% in mineral oil). The resulting mixture was stirred at 20-27° C. for 0.5 hour. Then 2-fluoro-6-nitrobenzonitrile (0.2 g, 1.20 mmol) was added to the above mixture. The resulting mixture was stirred at 20~27° C. for 20 hours. The reaction mixture was then poured into water (40 ml), extracted with EtOAc (20 mL×2). The combined organic layers was washed with brine (40 mL), dried over $Na_2SO_4$, filtered and concentrated under reduce pressure. The residue was purified by flash chromatography to give product 15b (0.28 g, 78.2% yield) as a yellow oil. LCMS: $R_t$=0.389 min in 1.5 min chromatography, MS (ESI) m/z=298.0 $[M+H]^+$. The product is a mixture of cis and trans isomer.

Procedure for the Preparation of Compound 15c:

To a solution of compound 15b (0.28 g, 0.94 mmol) in MeOH (10 mL) was added Pd—C (0.1 g, 50% $H_2O$ and 10% Pd). The resulting mixture was stirred under $H_2$ balloon at 20-25° C. for 1 hour. After completion, the reaction mixture was filtered, washed with MeOH (10 mL×3). The filtrate was concentrated under reduced pressure to give crude product 15c (0.2 g) as colorless oil which was used for next step without further purification. $^1H$ NMR (400 MHz, $CDCl_3$) δ 1.97-2.13 (0.3H, m), 2.13-2.24 (1H, m), 2.25-2.28 (1H, m), 2.97-2.98 (1H, m), 3.24-3.30 (1H, m), 4.34-4.48 (2H, m), 5.70 (td, J1=56.4 Hz, J2=4.8 Hz), 6.24 (0.6H, t, J=8.0 Hz), 6.32 (1H, d, J=8.0 Hz), 6.79 (0.7H, t, J=8.8 Hz), 7.18-7.23 (0.6H, m), 7.47-7.51 (0.3H, m).

Procedure for the Preparation of Compound 15d:

To a solution of compound 15c (0.05 g, 0.19 mmol) in toluene (5 mL) was added DMF-DMA (0.075 mL, 0.56 mmol). The resulting mixture was stirred at 110° C. for 2 hours. The reaction was concentrated under reduce pressure to give crude compound 15d (0.06 g) as a yellow oil which was used in the next step directly without further purification. LCMS: $R_t$=0.123 min in 1.5 min chromatography, MS (ESI) m/z=323.1 $[M+H]^+$.

Procedure for the preparation of Compound 15:

To a solution of compound 15d (0.054 g, 0.17 mmol) in AcOH (5 mL) was added compound 8e (0.04 g, 0.17 mmol). The resulting mixture was stirred at 110° C. for 2 hours. LCMS showed the reaction was completed. The reaction was concentrated under reduce pressure to give a residue. The residue was purifired by prep-HPLC (Waters Xbridge Prep OBD C18 150*30 5 u, 33%-63% B, A=water/0.05% ammonia hydroxide, B=MeCN). Most of MeCN was removed under reduced pressure, the remaining solvent was removed by lyophilization to afford isomer-1 Compound 15 (2.5 mg, yield: 2.9%) as a white solid and isomer-2 Compound 15' (1.4 mg, yield: 1.6%) as a yellow solid.

Compound 15 (±) isomer-1: LCMS: $R_t$=1.654 min in 4.0 min chromatography, MS (ESI) m/z=517.1 $[M+H]^+$. $^1H$ NMR (400 MHz, Methanol-$d_4$) δ 1.91-1.99 (2H, m), 2.22-2.25 (4H, m), 2.35 (1H, d, J=12.4 Hz), 3.01-3.05 (2H, m), 3.35 (1H, m), 5.28 (1H, s), 5.78 (1H, t, J=56.0, 4.4 Hz), 6.62 (1H, d, J=2.4 Hz), 6.82 (1H, d, J=7.6 Hz), 7.14 (1H, d, J=8.4 Hz), 7.20 (1H, d, J=8.0 Hz), 7.39 (1H, d, J=8.0 Hz),7.43 (1H, s), 7.70-7.79 (4H, m), 8.41 (1H, d, J=7.6 Hz), 8.48 (1H, s).

Compound 15': (±) isomer-2 LCMS: $R_t$=1.691 min in 4.0 min chromatography, MS (ESI) m/z 517.1 $[M+H]^+$. $^1H$ NMR (400 MHz, Methanol-$d_4$) δ 2.19-2.39 (5H, m), 2.72 (1H, d, J=12.4 Hz), 2.37 (1H, t, d, J=14.4 Hz), 3.48 (1H, t, J=13.2 Hz), 3.74 (1H, d, J=12.0 Hz), 4.09-4.14 (1H, m), 5.36 (1H, s), 6.33 (1H, t, J=53.6 Hz), 7.04 (1H, d, J=1.6 Hz),7.35 (2H, d, J=8.4 Hz), 7.50 (1H, d, J=8.0 Hz), 7.71 (1H, d, J=8.4 Hz), 7.83-7.91 (3H, m), 8.09-8.12 (2H, m), 8.80-8.82 (2H, m).

Example 16

N-(4-([1,2,4]triazolo[1,5-a]pyridin-7-yloxy)-3-methylphenyl)-5-((3,3-difluoropiperidin-4-yl)oxy)-7-methoxyquinazolin-4-amine

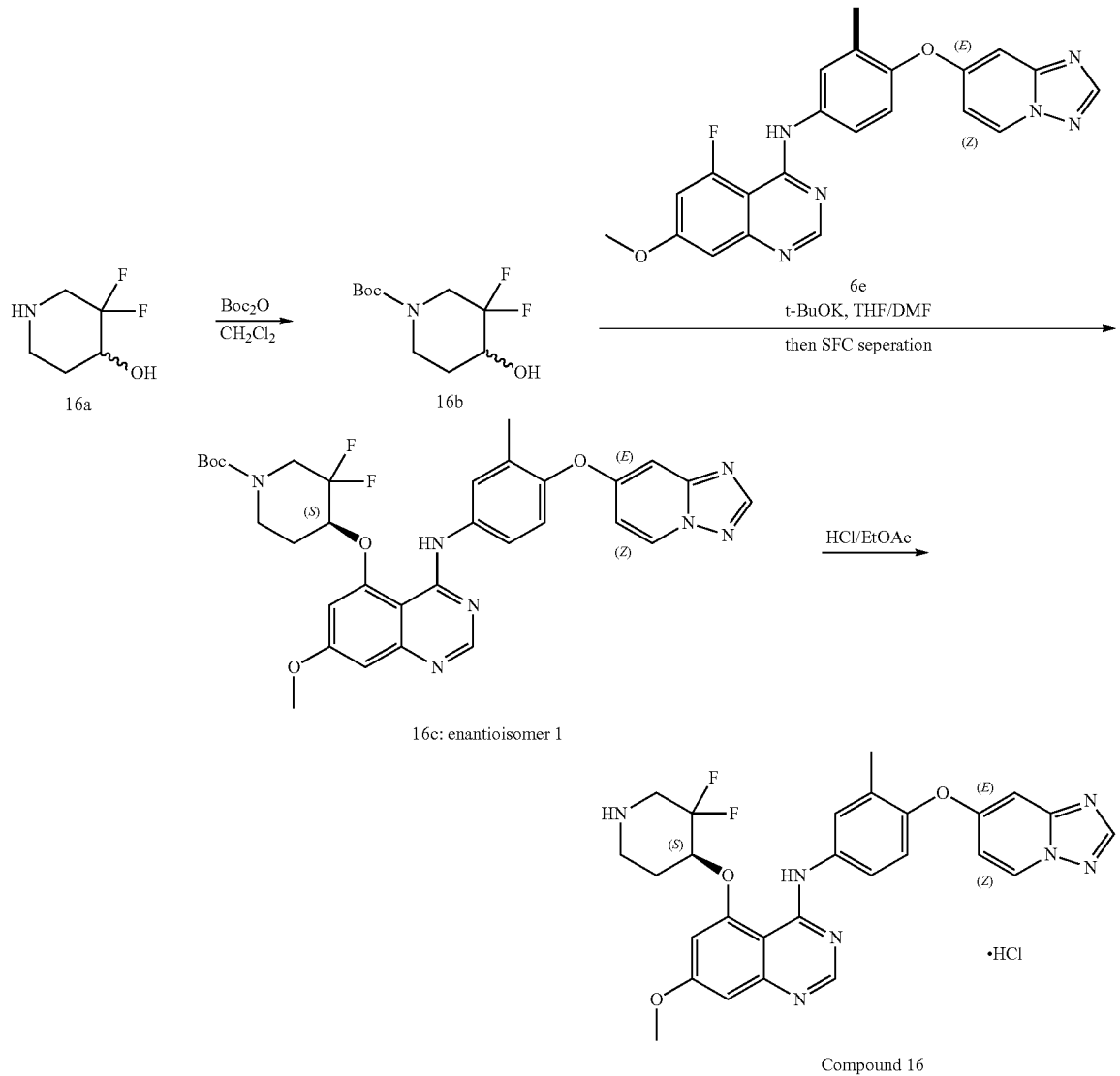

Procedure for the Preparation of Compound 16b:

To a solution of compound 16a (10 g, 72.92 mmol) in CH$_2$Cl$_2$ (200 mL) was added Boc$_2$O (15.92 g, 72.92 mmol) and the reaction mixture was stirred at 10° C. for 12 h. The mixture was concentrated under vacuum and the residue was partitioned between ethyl acetate (200 mL) and water (100 mL). The aqueous layer was extracted with EtOAc (50 mL×3). The combined organic layers were dried over Na$_2$SO$_4$, filtered and concentrated under vacuum. The residue was purified by silica column chromatography (20% EtOAc: 80% Petroleum ether, 120 g silica column) to give compound 16b (13 g, 75.1% yield) as a white solid. $^1$H NMR (400 MHz, CDCl$_3$) δ 4.03- 3.90 (m, 1H), 3.84-3.62 (m, 2H), 3.61-3.40 (m, 2H), 2.13 (br. s., 1H), 1.95 (br. s., 1H), 1.86-1.74 (m, 1H), 1.46 (s, 9H).

Procedure for the Preparation of Compound 16c:

To a solution of compound 16b (569.74 mg, 0.24 mmol) in THF/DMF (20 mL/8 mL) was added t-BuOK (404.21 mg, 0.36 mmol). The mixture was stirred at 20° C. for 20 mins. Then compound 6e (500 mg, 0.12 mmol) was added. The reaction mixture was stirred at 90° C. for 5 h and then concentrated under vacuum. After completion, the residue was partitioned between ethyl acetate (100 mL) and water (500 mL). The aqueous layer was extracted with EtOAc (50 mL×3). The combined organic layers were dried over Na$_2$SO$_4$, filtered and concentrated under vacuum. The residue was purified by silica column chromatography (10% MeOH: 90% DCM, 40 g silica column) to afford the crude product which was separated by SFC to give enantioisomer-1 compound 16c (300 mg, 16.43% Yield). LCMS: R$_t$=1.028 min in 10-80AB_2.0 min A:,Xtimate, 2.1*30 mm,3 um 3U411201577 B:XBrige Shield 2.1*50 mm, SN:01193135614705, MS (ESI) m/z=634.4 [M+H]$^+$. $^1$H NMR (400 MHz, CDCl$_3$) δ 9.62 (s, 1H), 8.61 (s, 1H), 8.53-8.46 (m, 1H), 8.22 (s, 1H), 7.79 (d, J=1.8 Hz, 1H), 7.67 (d, J=8.4 Hz, 1H), 7.07 (d, J=8.8 Hz, 1H), 6.97-6.84 (m, 3H), 6.51 (s, 1H), 4.74 (dt, J=5.3, 10.6 Hz, 1H), 4.21 (br. s., 1H), 4.00-3.91 (m, 3H), 3.72 (q, J=7.1 Hz, 1H), 3.34 (br. s., 1H), 3.12 (br. s., 1H), 2.41 (d, J=12.8 Hz, 1H), 2.27-2.20 (m, 3H), 2.09 (d, J=5.3 Hz, 1H), 1.57-1.32 (m, 9H).

Procedure for the Preparation of Compound 16:

To a solution of compound 16c (300 mg, 0.47 mmol) in EtOAc (10 mL) was added HCl/EtOAc (3 mL). The mixture was stirred at 10° C. for 1 h. The reaction mixture was concentrated under vacuum and the residue was purified by pre-HPLC to afford Compound 16 (217.0 mg, 85.9% Yield) as a white solid in the form of HCl salt. LCMS: R$_f$=0.746 min in 10-80AB_2.0 min_220&254 chromatography (Xtimate ODS 2.1*30 mm,3 um), MS (ESI) m/z=534.3 [M+H]$^{30}$. $^1$H NMR (400 MHz, Methanol-d$_4$) δ 9.06 (d, J=7.5 Hz, 1H), 8.99 (s, 1H), 8.77 (s, 1H), 7.89-7.76 (m, 2H), 7.42 (dd, J=2.4, 7.7 Hz, 1H), 7.34 (d, J=8.8 Hz, 1H), 7.29 (d, J=1.3 Hz, 1H), 7.16 (d, J=2.6 Hz, 1H), 6.97 (d, J=1.8 Hz, 1H), 5.78-5.63 (m, 1H), 4.16-4.03 (m, 4H), 3.90-3.75 (m, 1H), 3.66 (d, J=12.8 Hz, 1H), 3.56-3.44 (m, 1H), 2.85 (d, J=14.1 Hz, 1H), 2.47-2.32 (m, 1H), 2.29 (s, 3H).

Example 17

(S)—N-(4-([1,2,4]triazolo[1,5-a]pyridin-7-yloxy)-3-methylphenyl)-5-((3,3-difluoro-1-methylpiperidin-4-yl)oxy)-7-fluoroquinazolin-4-amine And (R)—N-(4-([1,2,4]triazolo[1,5-a]pyridin-7-yloxy)-3-methylphenyl)-5-((3,3-difluoro-1-methylpiperidin-4-yl)oxy)-7-fluoroquinazolin-4-amine

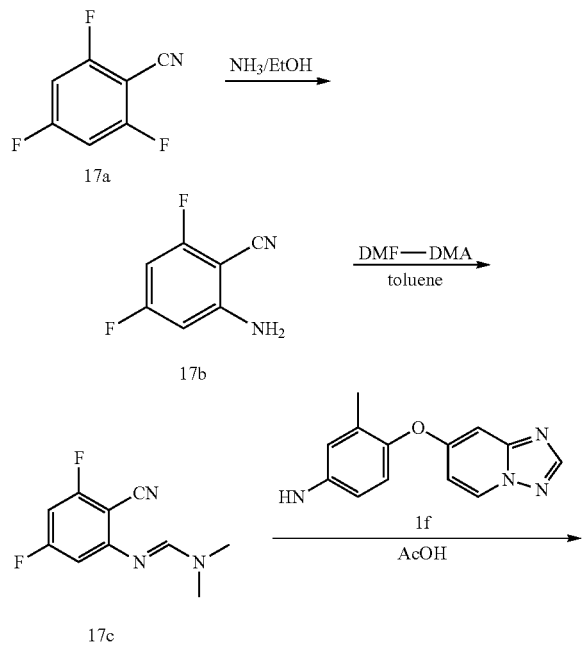

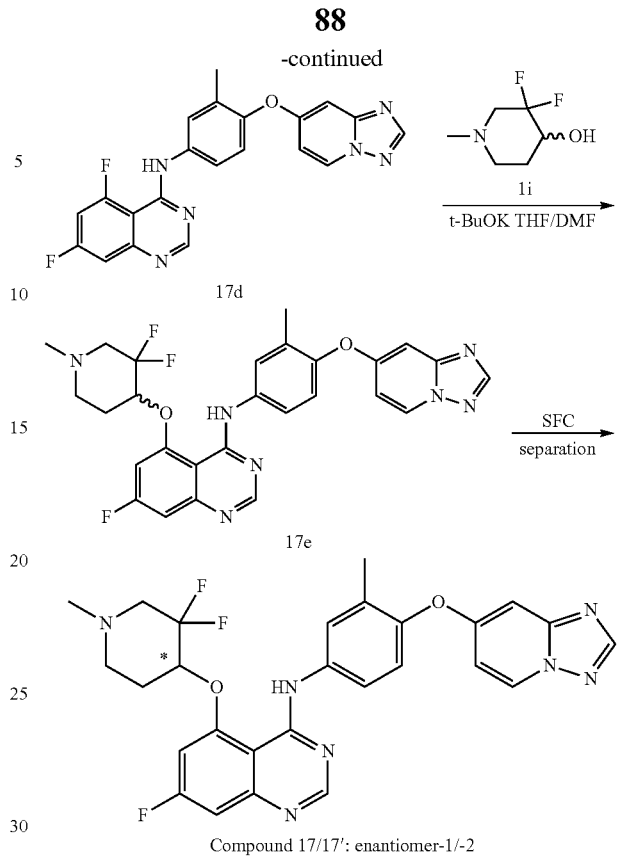

Compound 17/17': enantiomer-1/-2

Procedure for the Preparation of Compound 17b:

A solution of compound 17a (5 g, 31.8 mmol) in acetonitrile (128 mL) and ammonia (64 mL) was stirred at room temperature for 3 days as monitored by TLC (R$_f$=0.7, petroleum ether: ethyl acetate=2:1). The mixture was diluted with dichloromethane, washed with water. The organic layers were dried and concentrated to give crude product which was purified by silica gel chromatography eluted with petroleum ether: ethyl acetate=10:1 to 2:1(v/v) to give compound 17b (1.5 g, yield: 30%). $^1$H NMR (400 MHz, CDCl$_3$) δ 6.28-6.23 (m, 2H), 4.70 (br, 2H).

Procedure for the Preparation of Compound 17c:

A solution of compound 17b (500 mg, 3.24 mmol) and DMF-DMA (580 mg, 4.86 mmol) in toluene (20 mL) was stirred at 120° C. for 2 h as monitored by TLC (R$_f$=0.5, petroleum ether: ethyl acetate=2:1). The solvent was removed in vacuo to give compound 17c (690 mg, crude) which was used in the next step directly.

Procedure for the Preparation of Compound 17d:

A solution of compound 17c (690 mg, 3.24 mmol) and compound 1f (780 mg, 3.24 mmol) in acetic acid (15 mL) was stirred at 120° C. for 2h. The solvent was removed in vacuo and the residue was diluted with NaHCO$_3$ solution to adjust the pH to 7-8. Then the mixture was filtered and the filter cake was dried in vacuo to give compound 17d (720 mg, 55% yield). $^1$H NMR (400 MHz, DMSO-d$_6$) δ 9.25 (br, 1H), 8.93 (d, J=7.6 Hz, 1H), 8.56 (s, 1H), 8.37 (s, 1H), 7.70-7.65 (m, 3H), 7.57 (d, J=9.6 Hz, 1H), 7.20 (d, J=9.2 Hz, 1H), 7.02 (dd, 2.4 Hz, J$_2$=7.2 Hz, 1H), 6.78 (d, J=2.8 Hz, 1H), 2.18 (s, 3H).

Procedure for the preparation of Compound 17:

A solution of compound 17d (720 mg, 1.78 mmol), comound 1i (335 mg, 1.78 mmol) and potassium t-butoxide (700 mg, 6.23 mmol) in DMF-THF (40 mL, 2:5) was stirred at 100° C. overnight as monitored by LCMS. The solution was filtered and the filtrate was dried and concentrated to give crude product 17e (900 mg). 300 mg of crude product was purified by prep-HPLC (column: Waters Xbridge C18 150*20 mm*5 um, gradient: 34-54% B (A=water/0.05% ammonia, B=acetonitrile), flow rate: 25 mL/min) and SFC (column: OD (250 mm*50 mm, 5 um), condition: 40% EtOH in $NH_3 \cdot H_2O$ 50 mL/min) to give Compound 17 (64.9 mg) and Compound 17'(12.2 mg).

Compound 17 (enantiomer-1): LCMS: $R_t$=1.487 min in 4 min chromatography, MS (ESI) m/z=536.3 $[M+H]^+$. $^1H$ NMR (400 MHz, Methanol-$d_4$) δ 8.78-8.73 (m, 2H), 8.31 (s, 1H), 7.82-7.77 (m, 2H), 7.52 (dd, $J_1$=2.4 Hz, $J_2$=10.8 Hz, 1H), 7.23-7.10 (m, 3H), 6.80 (d, J=2.4 Hz, 1H), 5.45 (br, 1H), 3.81 (br, 1H), 3.39-3.31 (m, 2H), 3.04-3.01 (m, 1H), 2.77-2.69 (m, 4H), 2.32-2.21 (m, 4H).

Compound 17' (enantiomer-2): LCMS $R_t$=1.421 min in 4 min chromatography, MS (ESI) m/z 536.1 $[M+H]^+$. $^1H$ NMR (400 MHz, Methanol-$d_4$) δ 8.79-8.76 (m, 2H), 8.33 (s, 1H), 7.82-7.56 (m, 3H), 7.27-7.22 (m, 2H), 7.10 (dd, $J_1$=2.4 Hz, $J_2$=7.2 Hz, 1H), 6.81 (d, J=2.4 Hz, 1H), 75.56-5.49 (m, 1H), 3.94 (br, 1H), 3.54-3.43 (m, 2H), 3.22-3.15 (m, 1H), 2.86-2.74 (m, 4H), 2.34-2.28 (m, 4H).

Example 18

N-(4-([1,2,4]triazolo[1,5-a]pyridin-7-yloxy)-3-methylphenyl)-5-((3,3-difluoro-1-methylpiperidin-4-yl)oxy)-7-((tetrahydrofuran-3-yl)oxy)quinazolin-4-amine

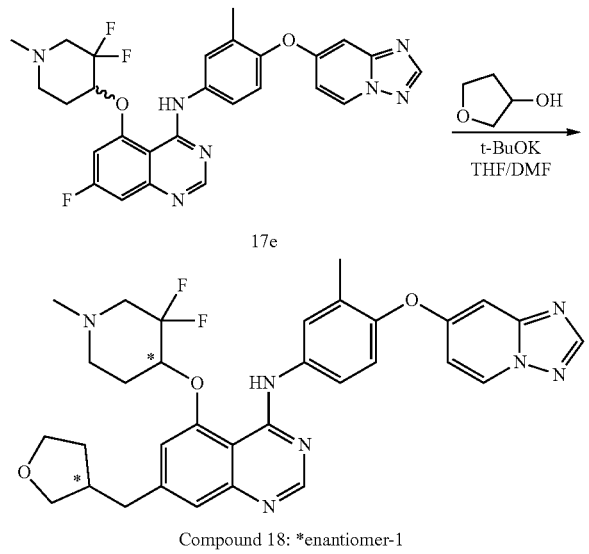

Procedure for the Preparation of Compound 18:

A solution of compound 17e (70 mg, 0.2 mmol), tetrahydrofuran-3-ol (35 mg, 0.4 mmol) and potassium t-butoxide (68 mg, 0.6 mmol) in DMF-THF (5 mL, 2:5) was stirred at 100° C. overnight as monitored by LCMS. The solution was purified by prep-HPLC (column: Phenomenex Gemini C18 200*25 mm*10 um, gradient: 37-67% B (A=water, B=acetonitrile), flow rate: 25 mL/min) followed by SFC separation to give Compound 18 (7.2 mg, 9.1% yield).

LCMS: $R_t$=1.540 min in 4 min chromatography, MS (ESI) m/z=604.1 $[M+H]^+$. $^1H$ NMR (400 MHz, Methanol-$d_4$) δ 8.72 (d, J=7.6 Hz, 1H), 8.44 (s, 1H), 8.27 (s, 1H), 7.79-7.77 (m, 2H), 7.14 (d, J=8.4 Hz, 1H), 7.04 (d, J=9.6 Hz, 1H), 6.88 (d, J=2.0 Hz, 1H), 6.79 (dd, $J_1$=2.4 Hz, $J_2$=7.2 Hz, 1H), 5.15-5.05 (m, 2H), 4.06-3.90 (m, 4H), 3.27 (brs, 1H), 2.95-2.92 (m, 1H), 2.47-2.35 (m, 7H), 2.22-2.18 (m, 4H), 2.06-2.06 (m, 1H).

Example 19

N-(4-([1,2,4]triazolo[1,5-a]pyridin-7-yloxy)-3-methylphenyl)-5-(((2S,4S)-5,5-difluoro-1,2-dimethylpiperidin-4-yl)oxy)quinazolin-4-amine And N-(4-([1,2,4]triazolo[1,5-a]pyridin-7-yloxy)-3-methylphenyl)-5-(((2R,4R)-5,5-difluoro-1,2-dimethylpiperidin-4-yl)oxy)quinazolin-4-amine

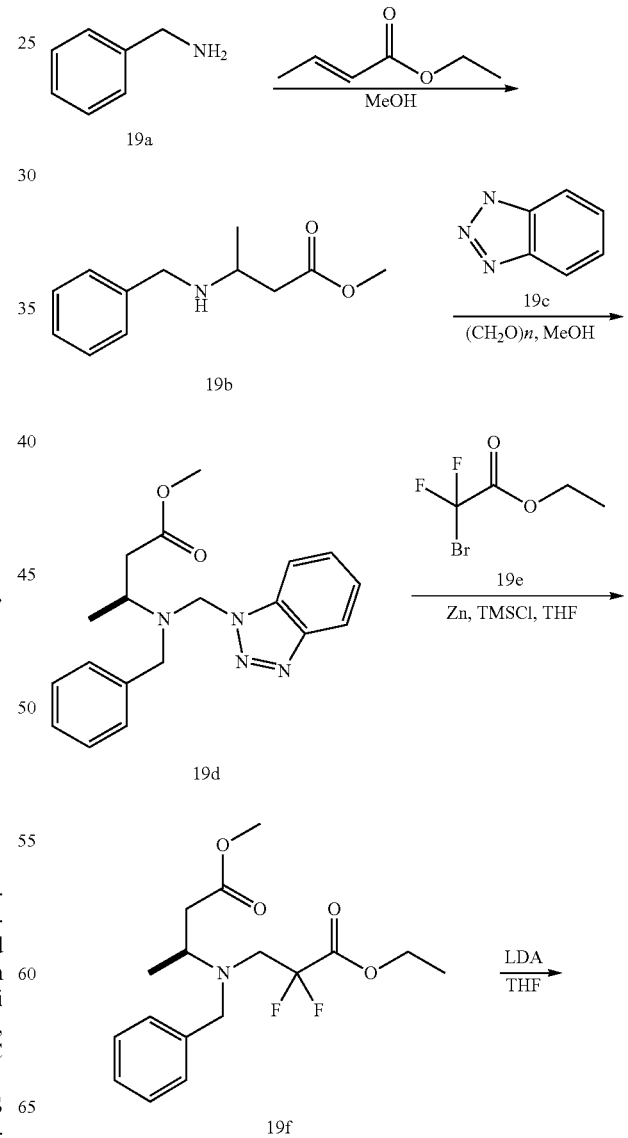

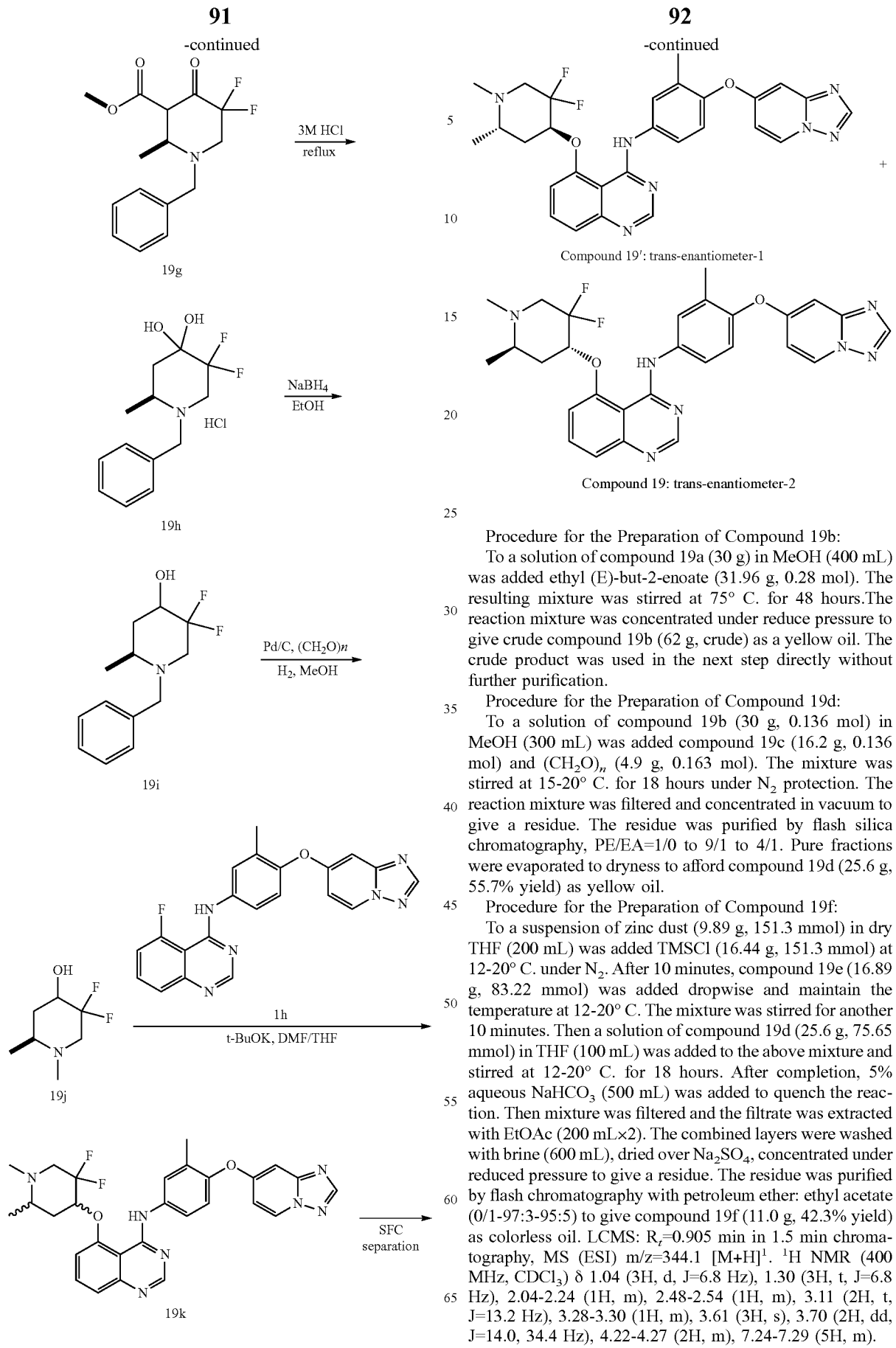

Procedure for the Preparation of Compound 19b:

To a solution of compound 19a (30 g) in MeOH (400 mL) was added ethyl (E)-but-2-enoate (31.96 g, 0.28 mol). The resulting mixture was stirred at 75° C. for 48 hours. The reaction mixture was concentrated under reduce pressure to give crude compound 19b (62 g, crude) as a yellow oil. The crude product was used in the next step directly without further purification.

Procedure for the Preparation of Compound 19d:

To a solution of compound 19b (30 g, 0.136 mol) in MeOH (300 mL) was added compound 19c (16.2 g, 0.136 mol) and $(CH_2O)_n$ (4.9 g, 0.163 mol). The mixture was stirred at 15-20° C. for 18 hours under $N_2$ protection. The reaction mixture was filtered and concentrated in vacuum to give a residue. The residue was purified by flash silica chromatography, PE/EA=1/0 to 9/1 to 4/1. Pure fractions were evaporated to dryness to afford compound 19d (25.6 g, 55.7% yield) as yellow oil.

Procedure for the Preparation of Compound 19f:

To a suspension of zinc dust (9.89 g, 151.3 mmol) in dry THF (200 mL) was added TMSCl (16.44 g, 151.3 mmol) at 12-20° C. under $N_2$. After 10 minutes, compound 19e (16.89 g, 83.22 mmol) was added dropwise and maintain the temperature at 12-20° C. The mixture was stirred for another 10 minutes. Then a solution of compound 19d (25.6 g, 75.65 mmol) in THF (100 mL) was added to the above mixture and stirred at 12-20° C. for 18 hours. After completion, 5% aqueous $NaHCO_3$ (500 mL) was added to quench the reaction. Then mixture was filtered and the filtrate was extracted with EtOAc (200 mL×2). The combined layers were washed with brine (600 mL), dried over $Na_2SO_4$, concentrated under reduced pressure to give a residue. The residue was purified by flash chromatography with petroleum ether: ethyl acetate (0/1-97:3-95:5) to give compound 19f (11.0 g, 42.3% yield) as colorless oil. LCMS: $R_t$=0.905 min in 1.5 min chromatography, MS (ESI) m/z=344.1 [M+H]$^1$. $^1$H NMR (400 MHz, CDCl$_3$) δ 1.04 (3H, d, J=6.8 Hz), 1.30 (3H, t, J=6.8 Hz), 2.04-2.24 (1H, m), 2.48-2.54 (1H, m), 3.11 (2H, t, J=13.2 Hz), 3.28-3.30 (1H, m), 3.61 (3H, s), 3.70 (2H, dd, J=14.0, 34.4 Hz), 4.22-4.27 (2H, m), 7.24-7.29 (5H, m).

Procedure for the Preparation of Compound 19g:

To a solution of LDA (70.5 mL, 2M in n-heptane and THF) in THF (100 mL) was added compound 19f (32.4 g, 4.08 mmol) in THF (100 mL) under $N_2$ at −65° C. The cooling bath was removed and the reaction mixture was warmed up to 15-23° C. slowly and stirred for another 20 hours. The reaction mixture was poured into $NH_4Cl$ (500 mL) and extracted with ethyl acetate (200 mL×3). The combined organic layers were washed with brine (600 mL) and dried over $Na_2SO_4$, filtered and concentrated under reduced pressure to give compound 19g (31.0 g, crude) as a brown oil. LCMS: $R_t$=0.866 min in 1.5 min chromatography, MS (ESI) m/z=298.0 [M+H]$^+$. $^1$H NMR (400 MHz, $CDCl_3$) δ 1.21-1.28 (3H, m), 3.06-3.10 (1H, m), 3.21-3.33 (2H, m), 3.69-3.84 (6H, m), 7.28-7.36 (5H, m).

Procedure for the Preparation of Compound 19h:

A solution of compound 19g (30.0 g, 100.9 mmol) in 3M HCl (400 mL) was heated to reflux and stirred for 18 hours. The reaction mixture was cooled down to room temperature and then adjusted pH to 7-8 with solid $NaHCO_3$. The aqueous phase was extracted with EtOAc (200 mL×3). The combined organic layers were washed with brine (700 mL), dried over $Na_2SO_4$ and concentrated in vacuum to give compound 19h (17.6 g, crude) which was used in the next step without further purification.

Procedure for the Preparation of Compound 19i:

To a solution of compound 19h (17.6 g, 0.068 mol) in EtOH (200 mL) was added $NaBH_4$ (3.86 g, 0.102 mol) at 0° C. The resulting mixture was stirred at 16-25° C. for 20 hours. After completion, HCl solution (3M, 10 mL) was added to quench the reaction. The reaction mixture was diluted with $H_2O$ (200 mL), extracted with EtOAc (200 mL×3). The combined organic layers were concentrated in vacuum to give compound 19i (16.8 g, crude) which was used in the next step without further purification. LCMS: $R_t$=0.173 min in 1.5 min chromatography, MS (ESI) m/z=242.0 [M+H]$^+$.

Procedure for the Preparation of Compound 19j:

To a solution of compound 19i (2.0 g, 8.29 mmol) and Pd/C (250 mg, 50% $H_2O$ and 10% Pd) in MeOH (50 mL) was added $(CH_2O)n$ (1.24 g, 41.45 mmol). The resulting mixture was stirred under an atmosphere of hydrogen at 50 psi and 50° C. for 18 hours. The reaction mixture was filtered, washed with MeOH (20 mL×3). The filtrate was concentrated under reduced pressure to give compound 19j (1.3 g, crude) as yellow oil which was used in the next step without further purification.

Procedure for the Preparation of Compound 19k:

To a solution of comound 1h (1.0 g, 2.59 mmol) in DMF (20 mL)/THF (8 mL) was added compound 19j (1.28 g, 7.77 mmol) and potassium tert-butoxide (1.02 g, 9.07 mmol). The resulting mixture was stirred at 100° C. for 16 hours. The reaction mixture was poured into water (100 mL) and extracted with ethyl acetate (100 mL×3). The combined organic layers were washed with brine (300 mL), dried over sodium sulfate and concentrated to give a residue. The residue was purified by prep-HPLC (column: Phenomenex Gemini C18 250*50 mm*10 um, 30-60% B (A=water/0.05% ammonia hydroxide, B=acetonitrile), Flow Rate: 90 mL/min) to give trans and cis mixture 19k (0.7 g, crude) as a pale red solid. LCMS: $R_t$=1.960 min in 4.0 min chromatography, MS (ESI) m/z=532.3 [M+H]$^+$.

Procedure for the Preparation of Compound 19:

Compound 19k (0.7 g, crude) was separated by preparative chiral-HPLC on a AD (250 mm*30 mm,5 um) column, Mobile phase: A: $CO_2$B:ethanol (0.05% DEA); Condition: Base-EtOH, Begin B 40% and End B 40%, Flow Rate (ml/min)=50. The fractions containing the desired compound were evaporated to dryness to afford four isomers and then re-purified by prep-HPLC (Waters Xbridge Prep OBD C18 150*30 5 u, 35%-65% B (A=water/0.05% ammonia hydroxide, B=MeCN) to afford trans-enantiomer-1 Compound 19'(16.3 mg, 2.3% yield) as a white solid and trans-enantiomer-2 Compound 19 (10.7 mg, yield: 1.5%, trans, peak 2) as a white solid. Compound 19' (trans-enantiomer-1): LCMS: $R_t$=1.946 min in 4.0 min chromatography, MS (ESI) m/z 532.3 [M+H]$^+$. $^1$H NMR (400 MHz, Methanol-$d_4$) δ 1.19 (3H, d, J=6.8 Hz), 2.11-2.16 (1H, m), 2.26 (3H, s), 2.31-2.38 (4H, m), 2.82 (1H, s), 2.91-2.97 (1H, m), 3.20-3.22 (1H, m), 5.22-5.24 (1H, m), 6.81 (1H, d, J=2.4 Hz), 7.06 (1H, dd, J=4.8, 7.2 Hz), 7.20 (1H, d, J=8.4 Hz), 7.29 (1H, d, J=8.0 Hz), 7.45 (1H, d, J=7.6 Hz), 7.77-7.82 (3H, m), 8.29 (1H, s), 8.52 (1H, s), 8.74 (1H, d, J=7.6 Hz). Compound 19 (trans-enantiomer-2): LCMS: $R_t$=1.902 min in 4.0 min chromatography, MS (ESI) m/z 532.3 [M+H]$^+$. $^1$H NMR (400 MHz, Methanol-$d_4$) δ 1.18 (3H, d, J=6.4 Hz), 2.08-2.13 (1H, m), 2.23 (3H, s), 2.29-2.37 (4H, m), 2.80 (1H, s), 2.89-2.92 (1H, m), 3.18-3.20 (1H, m), 5.17-5.24 (1H, m), 6.80 (1H, d, J=2.4 Hz), 7.03 (1H, d, J=7.6 Hz), 7.16 (1H, d, J=8.8 Hz), 7.27 (1H, d, J=8.4 Hz), 7.42 (1H, d, J=8.4 Hz), 7.74-7.79 (3H, m), 8.27 (1H, s), 8.49 (1H, s), 8.71 (1H, d, J=7.2 Hz).

Example 20

N-(4-([1,2,4]triazolo[1,5-a]pyridin-7-yloxy)-3-methylphenyl)-5-(((1R,3s,5S)-8-methyl-8-azabicyclo[3.2.1]octan-3-yl)oxy)quinazolin-4-amine

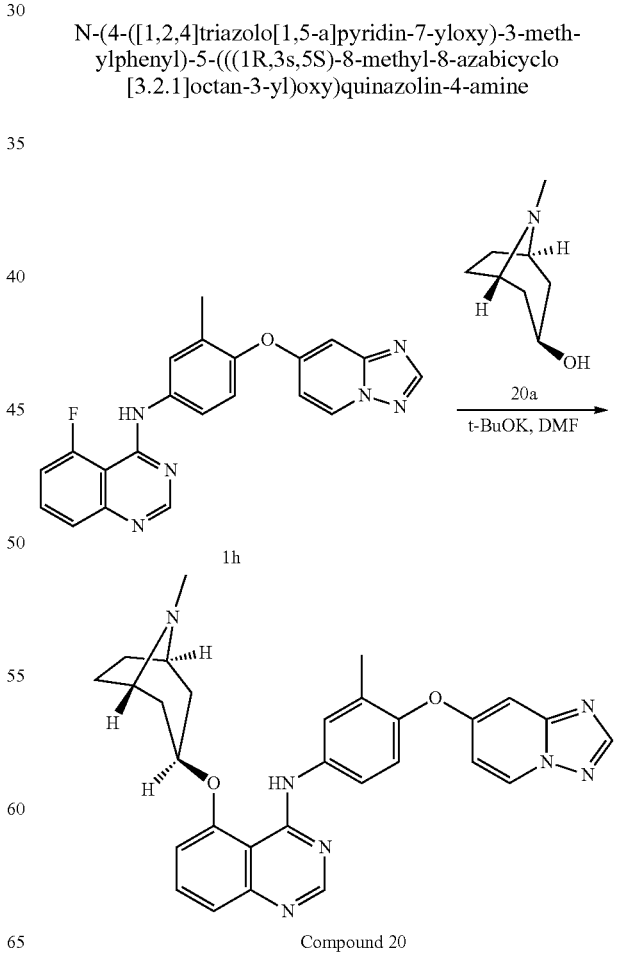

Compound 20

Procedure for the Preparation of Compound 20:

To a solution of comound 1h (100 mg, 0.26 mmol) in DMF (5 mL) was added potassium tert-butoxide (58 mg, 0.52 mmol) at 25° C. The resulting mixture was stirred at 90° C. for 5 days. The reaction mixture was cooled to 25° C. and filtered off. The filtrate was purified by preparative HPLC (column: Phenomenex Gemini C18 250*21.2 mm*5 um, 65-95% B (A=water/ 0.05% ammonia, B=methanol), flow rate: 25 mL/min) to give Compound 20 (9.1 mg, yield: 6.93%) as a white solid. LCMS: $R_t$=2.842 min in 4.0 min chromatography, MS (ESI) m/z=508.2 [M+H]$^+$. $^1$H NMR (400 MHz, CDCl$_3$) δ 1.74 (2H, d, J=7.6 Hz), 2.03-2.08 (2H, m), 2.18-2.33 (7H, m), 2.39 (3H, s), 3.33-3.43 (2H, m), 4.80-4.89 (1H, m), 6.88-6.95 (3H, m), 7.09 (1H, d, J=8.4 Hz), 7.46 (1H, d, J=8.0 Hz), 7.61-7.65 (2H, m), 7.77 (1H, s), 8.23 (1H, s), 8.49 (1H, d, J=7.6 Hz), 8.65 (1H, s), 10.13 (1H, br.s.)

Example 21

5-((5,5-difluoro-1-methylazepan-4-yl)oxy)-N-(4-(imidazo[1,2-a]pyridin-7-yloxy)-3-methylphenyl)quinazolin-4-amine

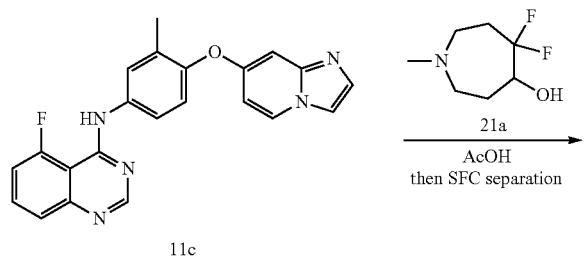

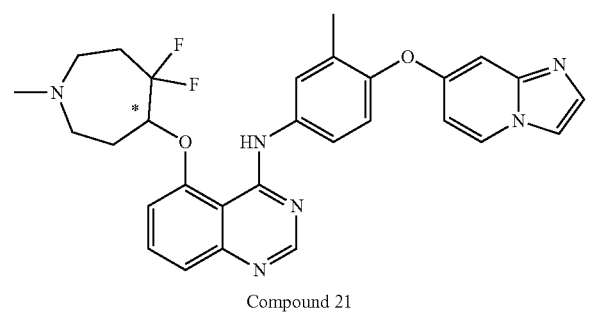

Compound 21

Procedure for the Preparation of Compound 21:

The synthesis followed a similar experimental procedure as Compound 11 to afford Compound 21 as solid after SFC separation. LCMS: $R_t$=1.459 min in 4.0 min chromatography. MS (ESI) m/z=531.3 [M+H]$^+$. $^1$H NMR (400 MHz, Methanol-d$_4$) δ 8.64 (d, J=7.6 Hz, 1H), 8.53 (s, 1H), 7.95 (s, 1H), 7.86-7.85 (m, 2H), 7.83 (t, J=8.4 Hz, 1H), 7.78-7.75 (m, 1H), 7.71-7.69 (m, 1H), 7.48 (d, J=8.0 Hz, 1H), 7.25-7.19 (m, 2H), 7.17-7.15 (m, 1H), 6.83 (s, 1H), 5.37-5.27 (m, 1H), 3.36-3.31 (m, 2H), 3.23-3.20 (m, 2H), 2.75 (s, 3H), 2.72-2.59 (m,2H), 2.49-2.40 (m, 2H), 2.26 (s, 3H).

Example 22

5-((3,3-difluoro-1-methylpiperidin-4-yl)oxy)-N-(4-((6-fluoro-[1,2,4]triazolo[1,5-a]pyridin-7-yl)oxy)-3-methylphenyl)-7-methoxyquinazolin-4-amine

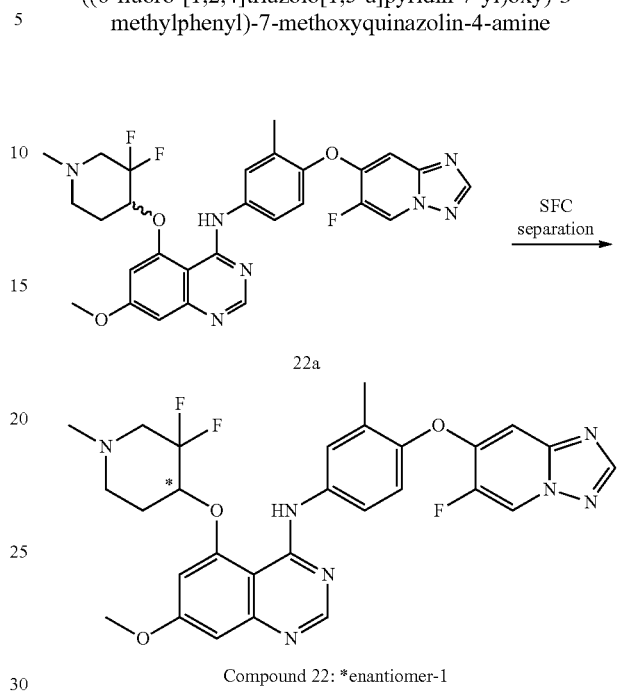

Compound 22: *enantiomer-1

The synthesis followed a similar experimental procedure as Compound 6 to afford Compound 22 as solid. The crude product 22a was purified by preparative SFC on a CHIRAL-PAK AD-H SFCS*25 cm, Sum Chiral-P(AD-H) 006S9OADHSCY-QH001 column, eluting isocratically with 50% CO$_2$ in IPA as eluent. The fractions containing the desired compound were evaporated to dryness to afford Compound 22 (enantiomer-1): (350 mg, 33.3% yield) as a off-white solid. LCMS: MS (ESI) m/z=566.2 [M+H]$^+$; HPLC $R_t$=1.911 min. $^1$H NMR (300 MHz, CDCl$_3$) δ 1.22 (d, 1H), 2.27 (s, 5H), 2.32-2.65 (m, 6H), 2.97 (d, 1H), 3.18-3.34 (m, 1H), 3.95 (s, 3H), 4.63 (td, 1H), 6.52 (d, 1H), 6.86 (d, 1H), 6.94 (d, 1H), 7.10 (d, 1H), 7.78 (dd, 1H), 7.85 (d, 1H), 8.23 (s, 1H), 8.55-8.67 (m, 2H), 9.80 (s, 1H).$^{19}$F NMR (282 MHz, CDCl$_3$) δ-154.2, -116.6, -109.7.

Example 23

5-((3,3-difluoro-1-methylpiperidin-4-yl)oxy)-N-(4-((6-fluoro-[1,2,4]triazolo[1,5-a]pyridin-7-yl)oxy)-3-methylphenyl)-6-methoxyquinazolin-4-amine

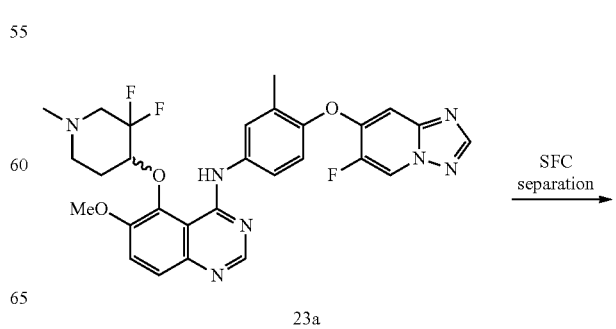

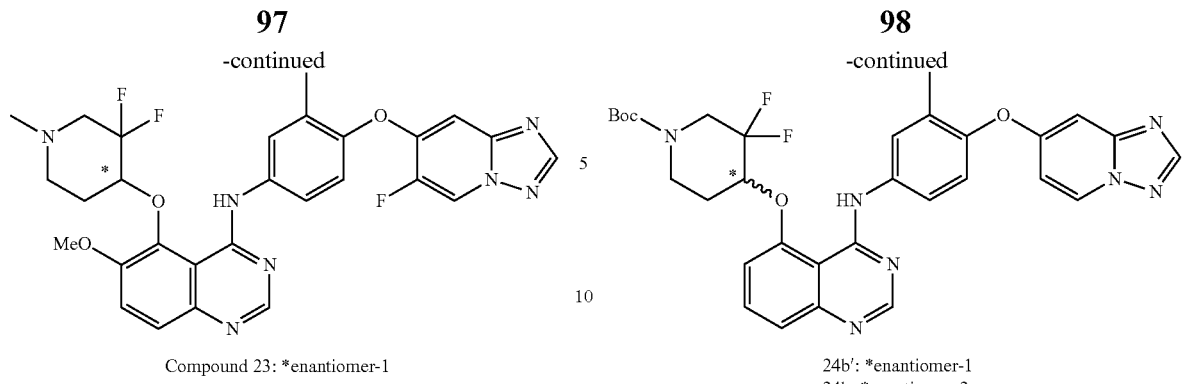

Compound 23: *enantiomer-1

The synthesis followed a similar experimental procedure as Compound 3 to afford Compound23a as solid. The crude product 23a was purified by preparative SFC on a CHIRALPAK IF2*25 cm, 5 um86445S90IF0SCJ-RA002 column, eluting isocratically with 50% $CO_2$ in EtOH (modified with $NH_3$ 2 mM) as eluent. The fractions containing the desired compound were evaporated to dryness to afford Compound 23 (enantiomer-1): (25.00 mg, 25.0% yield) as a off-white solid. Compound 23 (enantiomer-1): LCMS: MS (ESI) m/z=566.2 [M+H]$^+$; HPLC: $R_t$=1.193 min. $^1$H NMR (CRO-HER2_P-1-202-011-01, 300 MHz, Methanol-d4) δ 2.04-2.16 (m, 1H), 2.32 (d, 8H), 2.48 (dd, 1H), 2.94 (d, 1H), 3.19 (s, 1H), 4.07 (s, 3H), 4.89-5.06 (m, 1H), 6.86 (d, 1H), 7.23 (d, 1H), 7.63 (d, 1H), 7.79 (d, 1H), 7.85 (d, 2H), 8.30 (s, 1H), 8.44 (s, 1H), 9.07 (d, 1H). $^{19}$F NMR (282 MHz, Methanol-$d_4$) δ-156.2, -118.2, -111.7.

Example 24

N-(4-([1,2,4]triazolo[1,5-a]pyridin-7-yloxy)-3-methylphenyl)-5-((3,3-difluoro-1-(methyl-$d_3$)piperidin-4-yl)oxy)quinazolin-4-amine

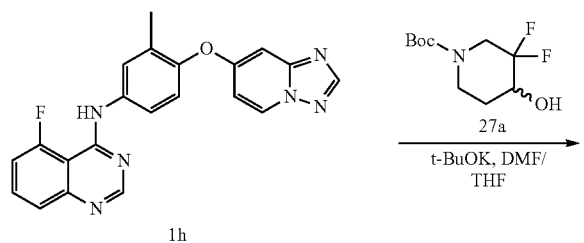

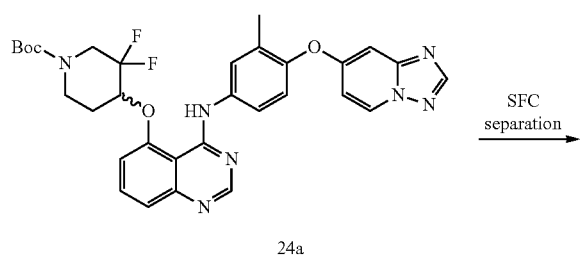

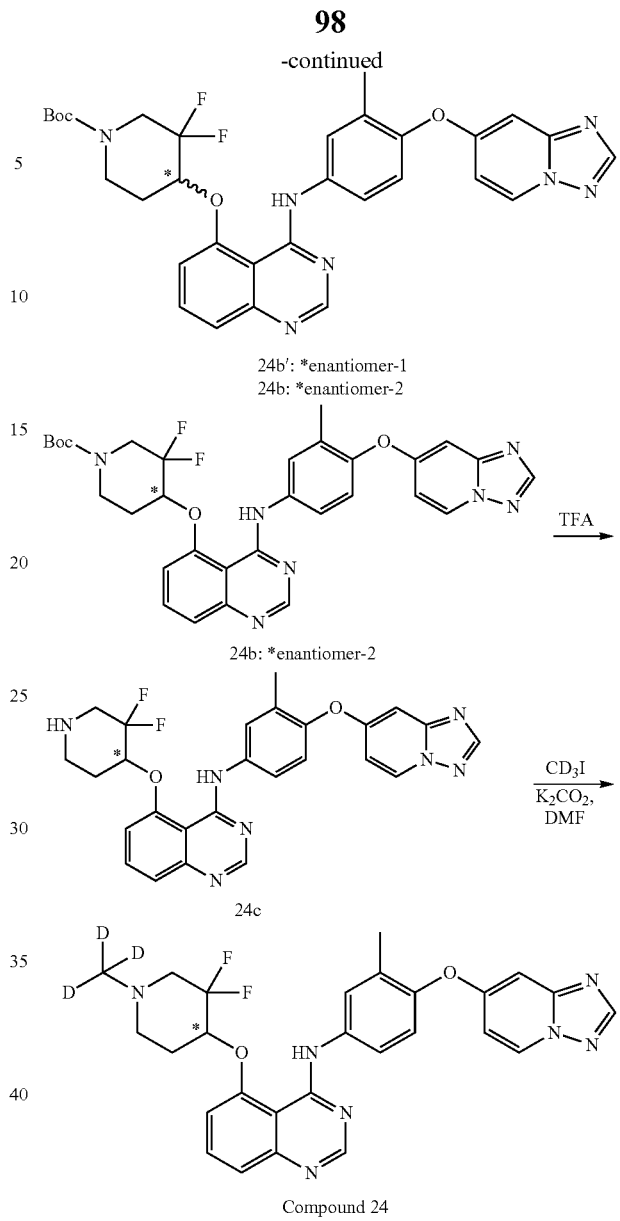

Procedure for the Preparation of Compound 24a:

To a solution of comound 1h (0.5 g, 1.29 mmol) in DMF (20 mL) and THF (8 mL) was added compound 27a (0.307 g, 1.29 mmol) and t-BuOK (0.508 g, 4.53 mmol). The resulting mixture was stirred at 100° C. for 16 hours. LCMS showed the reaction was completed. Water (20 mL) was added and extracted with EtOAc (30 mL×3), the combined organic layers were washed with brine (100 mL), dried over $Na_2SO_4$, and concentrated to give crude product, which was purified by flash silica chromatography, EtOAc/MeOH=1/0 to 9/1. Pure fractions were evaporated to dryness to afford compound 24a (760 mg, 92.2% yield) as a yellow oil. LCMS: $R_t$=2.794 min in 4.0 min chromatography, MS (ESI) m/z 604.1 [M+H]$^+$. SFC analysis Method: Column: Chiralcel OD-3 100×4.6 mm I.D., 3 um; Mobile phase: A: $CO_2$B: ethanol (0.05% DEA); Gradient: from 5% to 40% of B in 4.5 min and hold 40% for 2.5 min, then 5% of B for 1 min; Flow rate: 2.8 mL/min Column temperature:40° C.

Procedure for the Preparation of Compound 24b:

Compound 24a was separated by preparative chiral-HPLC on OD (250 mm*30 mm, 5 um) column, Mobile phase: A=CO$_2$, B=ethanol (0.05% DEA); Condition: Base-EtOH, Flow Rate: 50 ml/min. The fractions containing the desired compound were evaporated to dryness to afford compound 24b' (0.340 g, 44.7% yield) (isomer-1) and compound 24b (0.310 g, 40.8% yield) (isomer-2) as light yellow solid both. Compound 24b': enantiomer-1 LCMS: R$_t$=0.760 min in 1.5 min chromatography, MS (ESI) m/z 626.1 [M+Na]$^+$. Compound 24b: enantiomer-2 LCMS: R$_t$=0.762 min in 1.5 min chromatography, MS (ESI) m/z 626.1 [M+Na]$^+$.

Procedure for the Preparation of Compound 24c:

To a solution of compound 24b (0.15 g, 0.25 mmol, enantiomer-2) in DCM (4 mL) was added TFA (1 mL, 12.98 mmol). The resulting mixture was stirred at 16-18° C. for 2 hours. The reaction mixture was concentrated under reduce pressure to give a residue. The residue was diluted with MeOH (3 mL), adjusted pH to 8-9 with ammonia, then purified by prep-HPLC [Waters Xbridge Prep OBD C18 150*30 5u, 30%-60% B (A=water/0.05% ammonia hydroxide, B=MeCN)] to yield compound 24c (0.069 g, 55.1% yield) as a white solid. LCMS: R$_t$=1.946 min in 4.0 min chromatography, MS (ESI) m/z=504.2 [M+H]$^+$. $^1$HNMR (400 MHz, DMSO-d$_6$) δ 1.77-1.81 (1H, m), 2.20 (3H, s), 2.36 (1H, d, J=10.8 Hz), 2.65 (1H, s), 2.74 (1H, t, J=12.4 Hz), 2.88-2.99 (2H, m), 3.29-3.32 (1H, m), 5.30-5.39 (1H, m), 6.81 (1H, d, J=7.6 Hz), 7.02 (1H, d, J=7.6 Hz), 7.24 (1H, d, J=8.8 Hz), 7.40 (2H, dd, J=8.0, 17.6 Hz), 7.76-7.78 (2H, m), 7.87 (1H, s), 8.38 (1H, s), 8.59 (1H, s), 8.92 (1H, d, J=7.6 Hz), 10.15 (1H, s).

Procedure for the Preparation of Compound 24:

To a solution of compound 24c (300 mg, 0.596 mmol) in DMF (5 mL) was added CDI$_3$ (69 mg, 0.894 mmol) and K$_2$CO$_3$ (124 mg, 0.894 mmol). The resulting mixture was stirred at 27-31° C. for 3 hours. LCMS showed the reaction was completed. The reaction mixture was poured into water (20 mL), extracted with EA (20 mL×3). The combined organic layers were dried over Na$_2$SO$_4$, filtered and concentrated under reduce pressure to give a residue. The residue was purified by HPLC (Waters Xbridge Prep OBD C18 150*30 5u, 42-42% B, A=water (0.05% ammonia hydroxide), B=MeCN, Flow Rate (ml/min)=25 mL/min). Most of MeCN was removed under reduced pressure; the remaining solvent was removed by lyophilization to afford Compound 24 (25.1 mg, 8.1% yield) as a white solid. LCMS: R$_t$=2.026 min in 4.0 min chromatography, MS (ESI) m/z=521.3 [M+H]$^+$. $^1$H NMR (400 MHz, Methanol-d$_4$) δ 2.06-2.10 (1H, m), 2.25 (3H, s), 2.42-2.48 (2H, m), 2.64 (1H, dd, J=11.6, 28.8 Hz), 2.96 (1H, d, J=12.0 Hz), 3.24-3.27 (1H, m), 5.08-5.16 (1H, m), 6.81 (1H, d, J=2.8 Hz), 7.06 (1H, dd, J=2.4, 7.6 Hz), 7.18 (1H, d, J=8.4 Hz), 7.31 (1H, d, J=8.4 Hz), 7.45 (1H, d, J=8.4 Hz), 7.76-7.86 (3H, m), 8.28 (1H, s), 8.53 (1H, d, J=7.6 Hz), 8.73 (1H, d, J=7.6 Hz).

Example 25

(±)-N-(4-([1,2,4]triazolo[1,5-a]pyridin-7-yloxy)-3-methylphenyl)-5-(((2R,4S)-1-(methyl-d$_3$)-2-(trifluoromethyl)piperidin-4-yl)oxy)quinazolin-4-amine

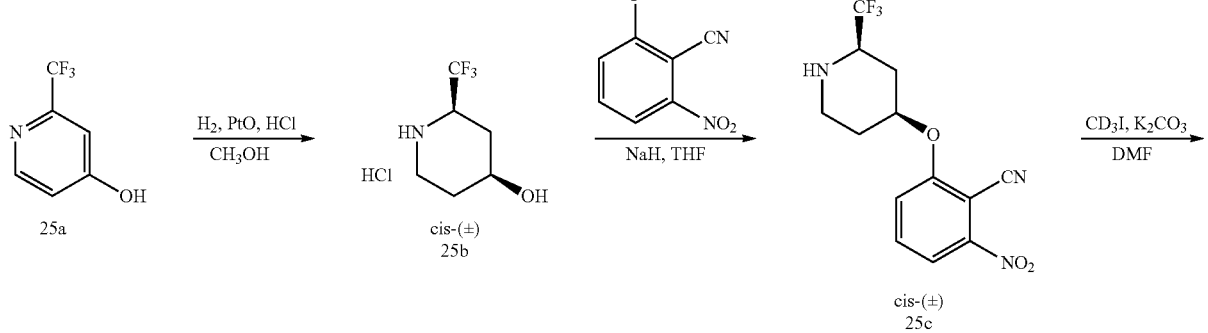

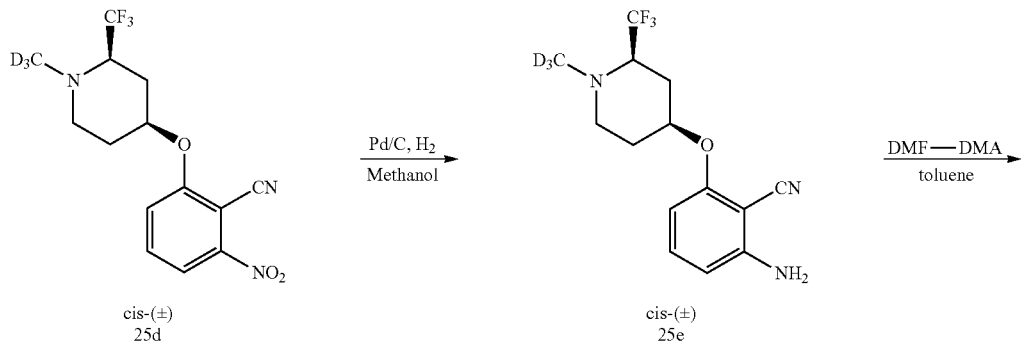

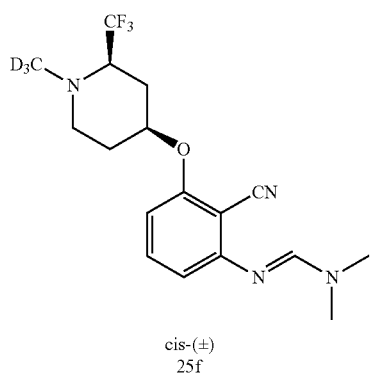

cis-(±)
25f

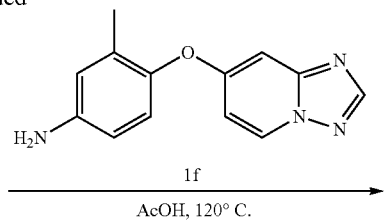

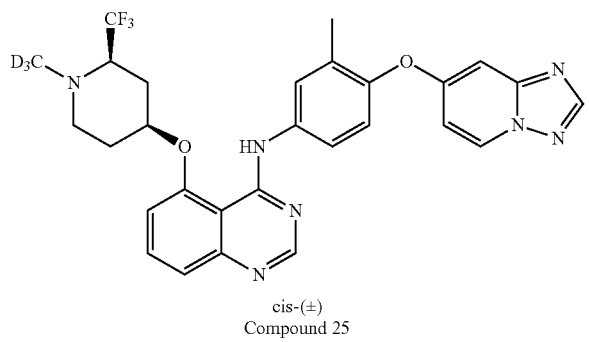

cis-(±)
Compound 25

Procedure for the Preparation of Compound 25b:

To a solution of compound 25a (15.0 g, 1.0 eq.) in methanol (200 mL) was added hydrochloric acid (12M, 3 mL) and PtO$_2$ (1.2 g). The mixture was stirred at 50° C. under hydrogen atmosphere (50 psi) for 3 days. The solid was dissolved with methanol (200 mL), and hydrochloric acid (12M, 3 mL) and PtO$_2$ (1.2 g) was added to the mixture was stirred at 50° C. under hydrogen atmosphere (50 psi) for 20 h. The mixture was filtered and concentrated to afford hydrochloride of compound 25b (18.2 g, 96% yield) as colorless solid. $^1$H NMR (400 MHz, Methanol-d$_4$) δ 1.60-1.86 (2H, m), 1.91-2.07 (1H, m), 2.17-2.27 (1H, m), 2.32-2.45 (0.5H, m), 3.10-3.30 (1H, m), 3.46-3.64 (1H, m), 3.90-4.00 (0.5H, m), 4.15-4.40 (1H, m).

Procedure for the Preparation of Compound 25c:

Compound 25b HCl salt was dissolved in methanol, basified by ammonia and concentrated, the residue was diluted with dichloromethane, filtered and the filtrate was concentrated to afford compound 25b (3.8 g, free base) which was used for the next steps. To a solution of compound 25b (300 mg, 1.2 eq.) in THF (10 mL) was added NaH (180 mg, 3.0 eq., 60%) under stirring. After 0.5 h, 2-fluoro-6-nitrobenzonitrile (250 mg, 1.0 eq.) was added to the reaction mixture and stirred at 21-29° C. for 2 days. LCMS analysis showed the reaction was almost completed. The mixture was poured into saturated solution of NH$_4$Cl (50 mL) and extracted with ethyl acetate (20 mL×3). The combined organic layers were dried over sodium sulfate, filtered and concentrated. The residue was purified by column chromatography on silica gel (0 to 50% EA in PE) to afford compound 25c (230 mg, 48% yield) as yellow oil. LCMS: R$_t$=0.641 min in 5-95AB 220&254 chromatography, MS (ESI) m/z=315.9 [M+H]$^+$.

$^1$H NMR (400 MHz, CDCl$_3$) δ 1.79-1.86 (2H, m), 2.18-2.29 (1H, m), 2.35-2.44 (1H, m), 2.78-2.83 (1H, m), 3.25-3.37 (1H, m), 3.38-3.45 (1H, m), 4.48-4.57 (1H, m), 7.37 (1H, d, J=8.0 Hz), 7.73 (1H, t, J=8.4 Hz), 7.90 (1H, d, J=8.4 Hz).

Procedure for the Preparation of Compound 25d:

To a mixture of compound 25c (180 mg, 1.0 eq.) and potassium carbonate (118 mg, 1.5 eq.) in DMF (10 mL) was added CD$_3$I (66 mg, 0.8 eq.). The mixture was stirred at 23-26° C. for 6 h. The reaction was poured into brine (50 mL) and extracted with EA (20 mL×3). The combined organic layers were dried over sodium sulfate, filtered and concentrated. The residue was purified by column chromatography on silica gel (0 to 30% EA in PE) to afford compound 25d (140 mg, crude) as brown oil. LCMS: R$_t$=0.684 min in 5-95AB_220&254 chromatography, MS (ESI) m/z=333.0 [M+H]$^+$. $^1$H NMR (400 MHz, CDCl$_3$) δ 1.94-2.05 (2H, m), 2.10-2.18 (1H, m), 2.35-2.51 (2H, m), 2.74-2.85 (1H, m), 3.05-3.15 (1H, m), 4.40-4.53 (1H, m), 7.35 (1H, d, J=8.4 Hz), 7.72 (1H, t, J=8.4 Hz), 7.89 (1H, d, J=8.4 Hz).

Procedure for the Preparation of Compound 25e:

To a solution of compound 25d (140 mg, 1.0 eq.) in methanol (10 mL) was added Pd/C (50 mg, 10%) under argon. The suspension was stirred at 24-30° C. under hydrogen (balloon) for 17 h. LCMS analysis showed the reaction was completed. The mixture was filtered and concentrated to afford compound 25e (60 mg, 68% yield) as yellow oil. LCMS: R$_t$=0.620 min in 5-95AB_220&254 chromatography, MS (ESI) m/z=303.1 [M+H]$^+$. $^1$H NMR (400 MHz, CDCl$_3$) δ 1.83-1.93 (2H, m), 2.08-2.14 (1H, m), 2.31-2.49 (2H, m), 2.71-2.79 (1H, m), 3.03-3.09 (1H, m), 4.25-4.35 (1H, m), 4.44 (2H, br. s), 6.25 (1H, d, J=8.4 Hz), 6.34 (1H, d, J=7.6 Hz), 7.22 (1H, t, J=8.4 Hz).

Procedure for the Preparation of Compound 25f:

To a mixture of compound 25e (60 mg, 1.0 eq.) in anhydrous toluene (10 mL) was added DMF-DMA (54 uL, 2.0 eq.). The mixture was stirred at 120° C. for 1 h. LCMS analysis showed the reaction was completed. The solution was concentrated to afford compound 25f (0.2 mmol, crude). LCMS: $R_t$=0.222 min in 5-95AB_220&254 chromatography, MS (ESI) m/z=358.1 [M+H]$^+$.

Procedure for the Preparation of Compound 25:

To a mixture of compound 25f (0.20 mmol, 1.0 eq.) in AcOH (10 mL) was added compound 1f (57 mg, 1.2 eq.). The mixture was stirred at 120° C. for 1.5 h. LCMS analysis showed the reaction was completed. The solution was concentrated. The residue was purified by pre-HPLC (column: DuraShell 150*25 mm*5 um, gradient: 50%-80% B (A=water/0.05% ammonia hydroxide, B=acetonitrile), flow rate: 25 mL/min) to afford Compound 25 (13.1 mg, 12% yield) as a white solid. LCMS: $R_t$=2.307 min in 0-60AB_4 min_220&254 chromatography, MS (ESI) m/z=553.3 [M+H]$^+$. HPLC: $R_t$=4.31 min in 0-60_AB_1.2 ml. $^1$H NMR (400 MHz, CDCl$_3$) δ 1.90-1.96 (1H, m), 2.01-2.08 (1H, m), 2.25 (3H, s), 2.35-2.43 (1H, m), 2.49-2.55 (1H, m), 2.62-2.69 (1H, m), 2.79-2.89 (1H, m), 3.12-3.19 (1H, m), 4.59-4.69 (1H, m), 6.87-6.91 (2H, m), 6.95 (1H, d, J=8.0 Hz), 7.11 (1H, d, J=8.4 Hz), 7.51 (1H, d, J=7.6 Hz), 7.62-7.74 (3H, m), 8.23 (1H, s), 8.50 (1H, dd, J$_1$=7.2 Hz, J$_2$=1.2 Hz), 8.68 (1H, s), 10.03 (1H, s).

Example 26

(±)-N-(4-([1,2,4]triazolo[1,5-a]pyridin-7-yloxy)-3-methylphenyl)-5-((3,3-difluoro-1-(methyl-d3)piperidin-4-yl)oxy)-6-(methoxy-d$_3$)quinazolin-4-amine

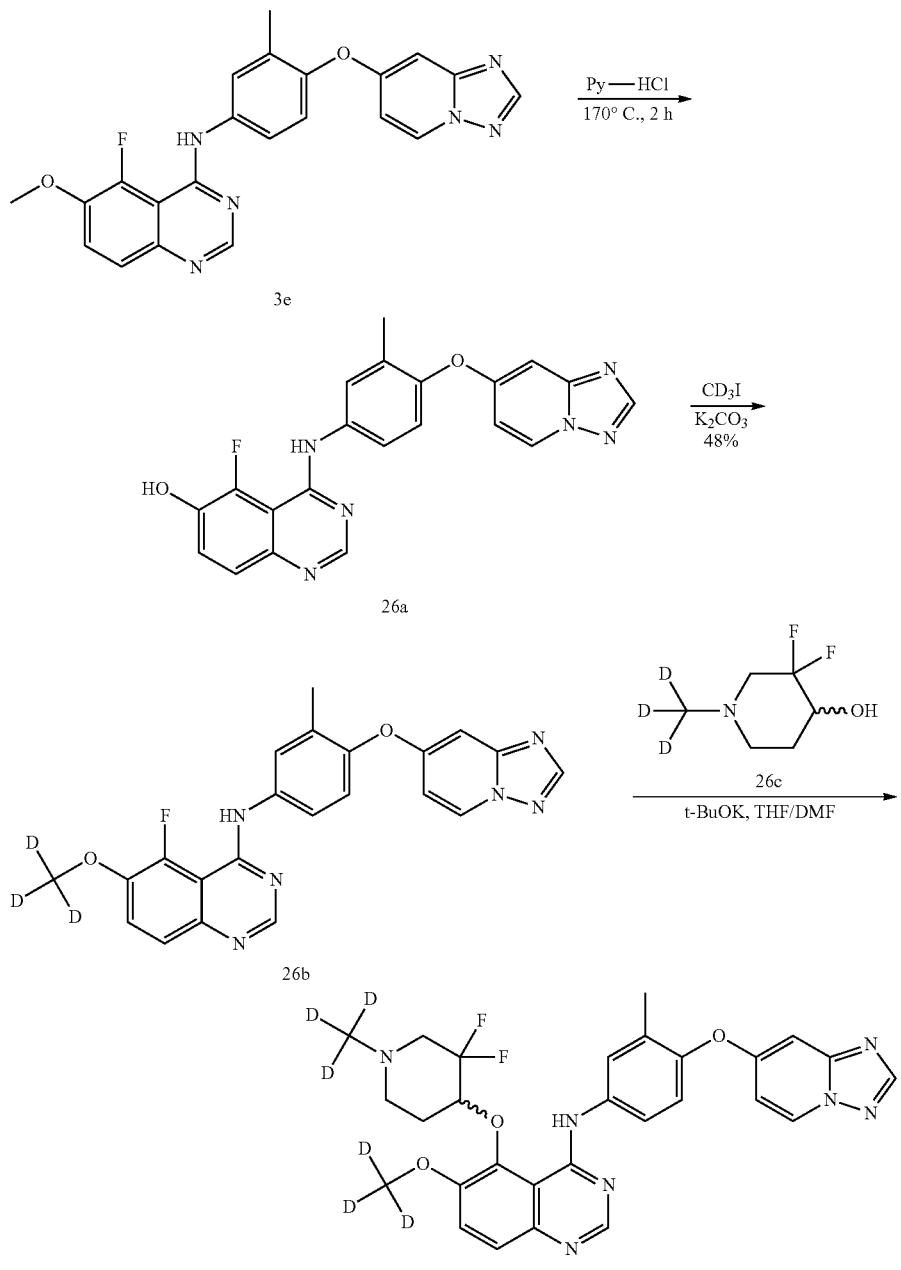

Compound 26: racemic

Procedure for the Preparation of Compound 26a:

A mixture of compound 3e (200 mg, 0.48 mmol) and pyridine hydrochloride (277.52 mg, 2.40 mmol) was stirred at 170° C. for 2h. The mixture was cooled to room temperature. The pH was adjusted to 8-9 with saturated NaHCO$_3$. The mixture was strongly stirred, filtered and the precipitate was washed with ethyl acetate (5 mL) to yield compound 26a (120 mg, 62.1% yield) as a brown solid. LCMS: R$_f$=0.956 min in 0-60AB_2 min_E chromatography (Merck RP-18e 25-2 mm, SN: UM9504/198), MS (ESI) m/z=403.2 [M+H]$^+$. $^1$H NMR (400 MHz, Methanol-d$_4$) δ 8.73 (br d, J=7.50 Hz, 1H), 8.09-8.39 (m, 2H), 7.69-7.87 (m, 2H), 7.30-7.49 (m, 2H), 7.03-7.25 (m, 2H), 6.87 (s, 1H), 2.24 (s, 3H).

Procedure for the Preparation of Compound 26b:

To a solution of compound 26a (120 mg, 0.30 mmol) and K$_2$CO$_3$ (49.46 mg, 0.36 mmol) in DMF (8 mL) was added CD$_3$I (51.88 mg, 0.36 mmol). The mixture was stirred at 20° C. for 12h. The mixture was filtered and concentrated to give the product which was purified by prep-TLC (CH$_2$Cl$_2$/MeOH=10:1, R$_f$=0.6) to give compound 26b (60 mg, 48% yield) as a yellow solid. LCMS: R$_t$=1.016 min in 0-60AB_2 min_E chromatography (Merck RP-18e 25-2 mm, SN: UM9504/198), MS (ESI) m/z=420.2 [M+H]$^+$. $^1$H NMR (400 MHz, Methanol-d$_4$) δ 8.73 (dd, J=7.50, 0.66 Hz, 1H), 8.44 (s, 1H), 8.28 (s, 1H), 7.78-7.87 (m, 1H), 7.70-7.76 (m, 2H), 7.66 (dd, J=9.15, 1.87 Hz, 1H), 7.19 (d, J=8.38 Hz, 1H), 7.07 (dd, J=7.50, 2.43 Hz, 1H), 6.84 (d, J=2.20 Hz, 1H), 2.25 (s, 3H).

Procedure for the Preparation of Compound 26:

To a solution of compound 26c (60.6 mg, 0.39 mmol) in THF (5 mL) and DMF (2 mL) was added tBuOK (44.1 mg, 0.39 mmol). The mixture was stirred at 20° C. for 30 min and then compound 26b (60 mg, 0.13 mmol) was added. The mixture was stirred at 90° C. for 12 h. The reaction mixture was filtered and concentrated under vacuum to give the crude product which was purified by preparative TLC (CH$_2$Cl$_2$/MeOH=10:1, R$_f$=0.5) to give Compound 26 (16.37 mg, 22.57% Yield) as a yellow solid. LCMS: R$_t$=1.034 min in 0-60AB_2.0 min chromatography (Welch Xtimate C18 2.1*30 mm 3 um), MS (ESI) m/z=554.1 [M+H]$^+$. $^1$H NMR (400 MHz, Methanol-d$_4$) δ 8.73 (d, J=7.72 Hz, 1H), 8.41 (s, 1H), 8.28 (s, 1H), 7.73-7.84 (m, 3H), 7.62 (d, J=9.26 Hz, 1H), 7.17 (d, J=8.38 Hz, 1H), 7.06 (dd, J=7.50, 2.65 Hz, 1H), 6.83 (d, J=2.65 Hz, 1H), 4.90-5.01 (m, 1H), 3.12-3.23 (m, 1H), 2.86-2.97 (m, 1H), 2.38-2.53 (m, 1H), 2.23-2.28 (m, 5H), 2.03-2.14 (m, 1H).

Example 27

(±)N-(4-([1,2,4]triazolo[1,5-a]pyridin-7-yloxy)-3-methylphenyl)-5-((3,3-difluoro-1-methylpiperidin-4-yl-4-d)oxy)-7-methoxyquinazolin-4-amine

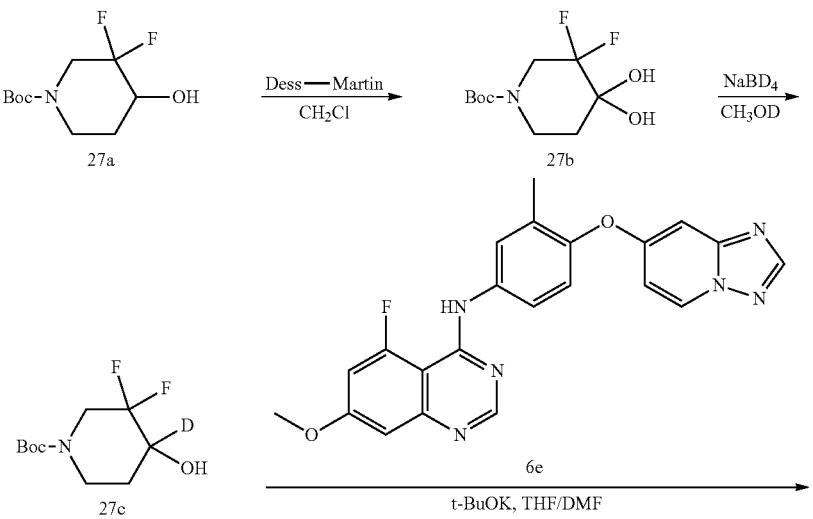

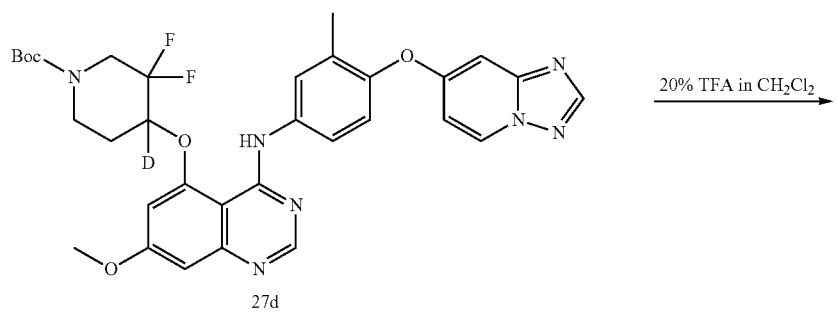

-continued

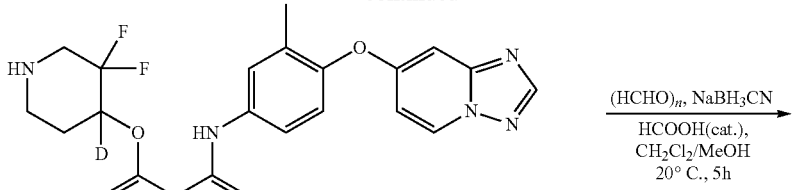

27e

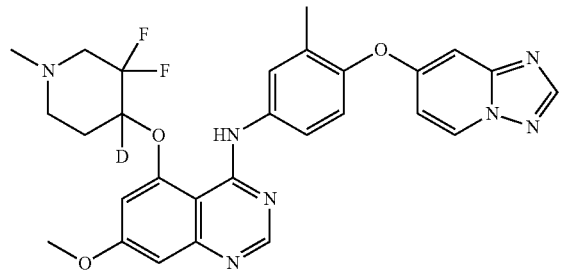

Compound 27: racemic

Procedure for the Preparation of Compound 27b:

To a solution of compound 27a (1.0 g, 4.22 mmol) in dry CH$_2$Cl$_2$ (50 mL) was added Dess-Martin regent (3.58 g, 8.44 mmol) slowly. The mixture was stirred at 20° C. for 2 h and then quenched by saturated Na$_2$SO$_3$/NaHCO$_3$ (v/v=3/1, 100 mL), extracted with CH$_2$Cl$_2$ (50 mL×2). The combined organic layers were dried over Na$_2$SO$_4$, filtered, and concentrated under vacuum to afford compound 27b (700 mg, 65.5% yield) as a white solid. $^1$H NMR (400 MHz, CDCl$_3$) δ 3.94 (br t, J=12.0 Hz, 1H), 3.79 (br t, J=6.1 Hz, 2H), 3.61-3.52 (m, 1H), 3.11 (br s, 1H), 2.76 (br t, J=6.0 Hz, 1H), 1.93 (br s, 1H), 1.49 (d, J=14.5 Hz, 9H).

Procedure for the Preparation of Compound 27c:

To a solution of compound 27b (700 mg, 2.76 mmol) in dry CD$_3$OD (5 mL) was added NaBD$_4$ (231.07 mg, 5.52 mmol) slowly at 0° C. under N$_2$. The mixture was stirred at 20° C. for 1h, then quenched by D$_2$O (10 mL), extracted with EtOAc (50 mL×3). The combined organic layers were dried over Na$_2$SO$_4$, filtered, and concentrated under vacuum to afford crude compound 27c (500 mg, 76.1% yield) as a white solid. $^1$H NMR (400 MHz, CDCl$_3$) δ 3.88-3.62 (m, 2H), 3.60-3.40 (m, 2H), 2.24 (br s, 1H), 2.00-1.88 (m, 1H), 1.86-1.73 (m, 1H), 1.53-1.44 (m, 9H).

Procedure for the Preparation of Compound 27d:

To a solution of compound 27c (300 mg, 1.26 mmol) in dry THF/DMF (10 mL/4 mL) was added t-BuOK (212.06 mg, 1.89 mmol) under N$_2$ at 20° C. and stirred for 30 mins at this temperature. Compound 6e (262.55 mg, 0.63 mmol) was added and then heated at 90° C. for 12 h. The reaction mixture was diluted with 30 mL of water, extracted with EtOAc (50 mL×2). The combined organic layers were washed with brine (20 mL), dried over Na$_2$SO$_4$, filtered and concentrated under vacuum. The residue was purified by column chromatography on silica gel (CH$_2$Cl$_2$/MeOH=100/1 to 20/1, R$_f$=0.4) to afford compound 27d (320 mg, 80% yield) as a yellow solid. LCMS: R$_t$=1.254 min in 0-60AB_2.0 min_220 & 254 chromatography (Xtimate 3 um, C18, 2.1*30 mm S/N3U), MS (ESI) m/z 634.9 [M+H]$^+$. $^1$H NMR (400 MHz, CDCl$_3$) δ 9.63 (s, 1H), 8.62 (s, 1H), 8.49 (d, J=8.4 Hz, 1H), 8.23 (s, 1H), 7.80 (s, 1H), 7.68 (br d, J=8.6 Hz, 1H), 7.08 (d, J=8.6 Hz, 1H), 6.93 (d, J=1.4 Hz, 1H), 6.91-6.83 (m, 2H), 6.52 (d, J=1.8 Hz, 1H), 4.45 (br s, 1H), 4.25-4.10 (m, 1H), 3.95 (s, 3H), 3.35 (br s, 1H), 3.13 (br s, 1H), 2.41 (br d, J=10.2 Hz, 1H), 2.25 (s, 3H), 2.14-2.00 (m, 1H), 1.50 (s, 9H).

Procedure for the Preparation of Compound 27e:

Compound 27d (320 mg, 0.5 mmol) was dissolved in TFA solution in CH$_2$Cl$_2$ (20%, 10 mL) and stirred at 20° C. for 3 h. The reaction mixture was adjusted pH to 7-8 with NaHCO$_3$ (sat.), extracted with CH$_2$Cl$_2$ (30 mL×2). The combined organic layers were washed with brine (10 mL), dried over Na$_2$SO$_4$, filtered and concentrated under vacuum to give compound 27e (280 mg, crude) as a yellow solid. $^1$H NMR (400 MHz, CDCl$_3$) δ 9.75 (s, 1H), 8.51 (s, 1H), 8.43 (d, J=7.4 Hz, 1H), 8.13 (s, 1H), 7.74 (s, 1H), 7.66 (br d, J=8.6 Hz, 1H), 7.00 (d, J=8.8 Hz, 1H), 6.88-6.76 (m, 3H), 6.52 (d, J=2.2 Hz, 1H), 6.55-6.50 (m, 1H), 3.86 (s, 3H), 3.42-3.31 (m, 1H), 3.13 (br d, J=13.5 Hz, 1H), 3.02-2.88 (m, 1H), 2.77 (br t, J=12.8 Hz, 1H), 2.43-2.35 (m, 1H), 2.17 (s, 3H), 1.93-1.90 (m, 2H).

Procedure for the Preparation of Compound 27:

To a solution of compound 27e (140 mg, 0.26 mmol) in dry CH$_2$Cl$_2$/MeOH (4 mL/4 mL) was added (HCHO)$_n$ (23.4 mg, 0.26 mmol) and followed by 5 drops of HCOOH (1 drop of pure HCOOH diluted by 1 mL of CH$_2$Cl$_2$). The mixture was stirred at 20° C. for 12 h and then NaCNBH$_3$ (163.4 mg, 2.6 mmol) was added. The resulting mixture was stirred at 20° C. for 30 mins and quenched with 10 mL of sat. NH$_4$Cl, extracted with CH$_2$Cl$_2$ (50 mL×3). The combined organic layers were washed with brine (30 mL), dried over Na$_2$SO$_4$, filtered and concentrated under vacuum. The residue was purified by column chromatography on silica gel (CH$_2$Cl$_2$/MeOH=100/1 to 15/1, R$_f$=0.3) to afford Compound 27 (40.32 mg, 28.3% yield) as a yellow solid. LCMS: R$_t$=0.690 min in 5-95AB_1.5min_220&254 chromatography (Merck RP-18e 25-2 mm, SN: UM9504), MS (ESI) m/z 549.1[M+H]$^+$. $^1$H NMR (400 MHz, Methanol-d$_4$) δ 8.72 (d, J=7.5 Hz, 1H), 8.44 (s, 1H), 8.27 (s, 1H), 7.87-7.70 (m, 2H), 7.14 (d, J=8.4 Hz, 1H), 7.08-6.97 (m, 1H), 6.92-6.76 (m, 3H), 3.95

(s, 3H), 3.31 (br s, 2H), 3.29-3.19 (m, 1H), 2.94 (br d, J=11.9 Hz, 1H), 2.70-2.54 (m, 1H), 2.52-2.35 (m, 5H), 2.22 (s, 3H), 2.12-1.97 (m, 1H).

Example 28

(S)—N-(4-([1,2,4]triazolo[1,5-a]pyridin-7-yloxy)-3-methylphenyl)-5-((3,3-difluoro-1-(methyl-d₃)piperidin-4-yl-4-d)oxy)-7-methoxyquinazolin-4-amine And (R)—N-(4-([1,2,4]triazolo[1,5-a]pyridin-7-yloxy)-3-methylphenyl)-5-((3,3-difluoro-1-(methyl-d₃)piperidin-4-yl-4-d)oxy)-7-methoxyquinazolin-4-amine

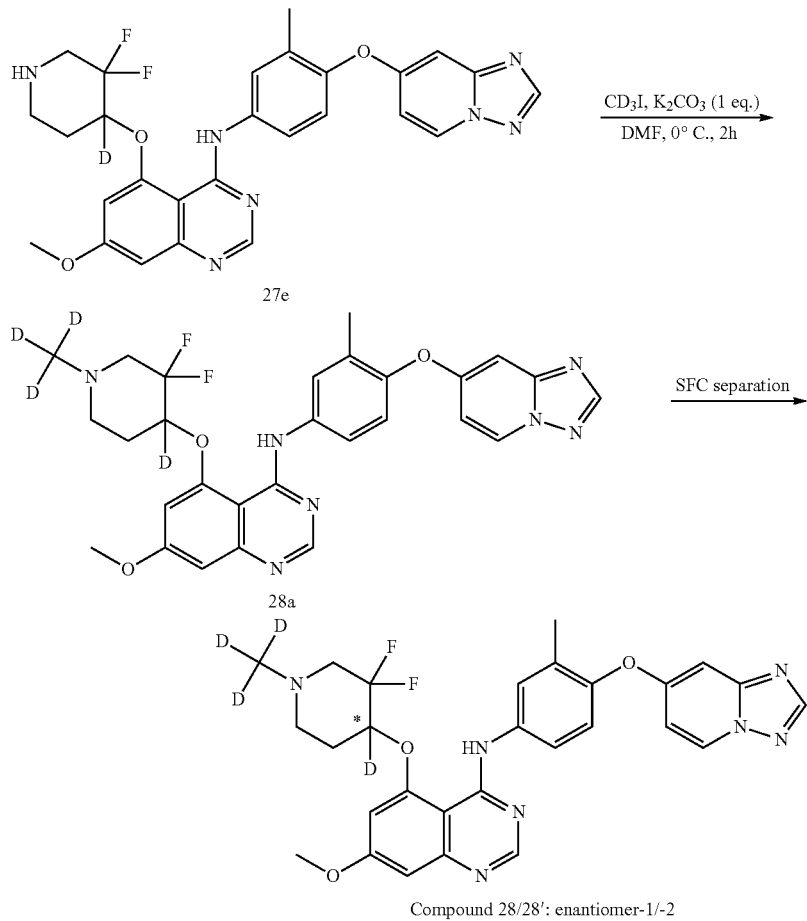

Compound 28/28′: enantiomer-1/-2

Procedure for the Preparation of Compound 28a:

To a solution of compound 27e (140 mg, 0.262 mmol) and $K_2CO_3$ (145 mg, 0.275 mmol) in dry DMF(5 mL) was added $CD_3I$ (37.97 mg, 0.262 mmol) dropwise under $N_2$ at 20° C. and stirred for 2 h at this temperature. The reaction was diluted with 20 mL water, extracted with EtOAc (30 mL×3), washed with brine(10 mL), dried over $Na_2SO_4$, filtered, concentrated, and the residue was purified by prep-HPLC (Instrument: AA/Boston Green ODS 150*30 5 u Condition water (0.05% HCl)-ACN Begin B 5 End B 30 Gradient Time(min) 12 100% B Hold Time(min) 2.2 FlowRate(ml/min) 25)) to afford compound 28a (48.3 mg, 27.9% yield) as a yellow solid in the form of HCl salt. LCMS: $R_t$=1.204 min in 0-60AB_2.0 min_220&254 chromatography (Xtimate 3 um, C18, 2.1*30 mm S/N3U411201576), MS (ESI) m/z 552.1[M+H]⁺. ¹H NMR (400 MHz, Methanol-d₄) δ 8.96 (br d, J=7.1 Hz, 1H), 8.81-8.59 (m, 2H), 7.98-.71 (m, 2H), 7.45-7.24 (m, 3H), 6.99 (br d, J=17.4 Hz, 2H), 4.28 (br s, 1H), 4.08 (s, 3H), 4.01-3.85 (m, 1H), 3.79 (br d, J=11.9 Hz, 1H), 3.66-3.52 (m, 1H), 2.87 (br d, J=14.8 Hz, 1H), 2.46 (br t, J=12.3 Hz, 1H), 2.29 (s, 3H).

Procedure for the Preparation of Compound 28:

Compound 28a (45 mg, 0.068 mmol) was purificated by chiral SFC (SFC Method: Instrument: SFC-MS Method: Column: Chiralcel AD(250 mm*30 mm,10 um) Condition: 0.1% NH₃H₂O IPA Begin B:45%, End B:45%, Flow rate:80 mL/min) and lyophilized to afford Compound 28 (18.9 mg, 50.4% yield) and Compound 28′ (18.1 mg, 48.3% yield) as yellow solid.

Compound 28 (enantiomer-1): SFC: $R_t$=5.868 min (220 nm) OD-H_EtOH(DEA)_5_40_2.5M (Column: Column: ChiralCel OD-H 150×4.6 mm I.D., 5 um Mobile phase: A: CO2 B:Ethanol (0.05% DEA) Gradient: from 5% to 40% of B in 5.5 min and hold 40% for 3 min, then 5% of B for 1.5 min Flow rate: 2.5 mL/min Column temperature:40° C.). ¹H NMR (400 MHz, Methanol-d₄) δ 9.87 (s, 1H), 8.92 (d, J=7.7 Hz, 1H), 8.51 (s, 1H), 8.37 (s, 1H), 7.82 (s, 1H), 7.73 (dd, J=2.1, 8.7 Hz, 1H), 7.23 (d, J=8.8 Hz, 1H), 7.04-6.99 (m, 2H), 6.88 (d, J=2.0 Hz, 1H), 6.81 (d, J=2.4 Hz, 1H), 3.92 (s, 3H), 3.26-3.16 (m, 1H), 2.82 (br d, J=11.5 Hz, 1H), 2.56 (br s, 1H), 2.40-2.29 (m, 2H), 2.18 (s, 3H), 1.96-1.85 (m, 1H).

Compound 28' (Enantiomer-2): SFC: $R_t$=6.789 min (220 nm) OD

H_EtOH(DEA)_5_40_2.5M (Column: ChiralCel OD-H 150×4.6 mm I.D., 5 umMobile phase: A: $CO_2$B:Ethanol (0.05% DEA) Gradient: from 5% to 40% of B in 5.5 min and hold 40% for 3 min, then 5% of B for 1.5 min Flow rate: 2.5 mL/min Column temperature: 40° C.). $^1$H NMR (400 MHz, Methanol-$d_4$) δ 9.87 (s, 1H), 8.92 (d, J=7.5 Hz, 1H), 8.51 (s, 1H), 8.37 (s, 1H), 7.82 (br s, 1H), 7.74 (br d, J=8.8 Hz, 1H), 7.23 (br d, J=8.8 Hz, 1H), 7.02 (br s, 2H), 6.89 (s, 1H), 6.81 (d, J=2.0 Hz, 1H), 3.92 (s, 3H), 3.24 (br d, J=10.8 Hz, 1H), 2.82 (br d, J=11.0 Hz, 1H), 2.56 (br s, 1H), 2.41-2.29 (m, 2H), 2.18 (s, 3H), 1.96-1.79 (m, 1H).

Biological Examples

Example 29

Potency Assessment Against WT EGFR

A compound's activity of inhibition for EGFR WT can be evaluated with NCI-H838 (ATCC® CRL-5844™), which expresses wild type EGFR protein as the count screening to define the selectivity of the compound.

The compounds' inhibition of target modulation were determined as follows: NCI-H838 cells were sorted in 96 well plates (20000 cells/well) with the DMEM medium containing 1% FBS overnight and then treated with tested compounds at a series of concentrations (3 μM, 0.3 μM, 0.1 μM, 0.03 μM, 0.01 μM, 0.003 μM, 0.001 μM, 0.0001 μM). The plates were incubated for 4 h at 37° C. with 5% $CO_2$ followed by the stimulation of recombinant hEGF (100 ng/ml for 10 Min, RD, Cat #236-EG) and then the EGFR (Y1068) phosphorylation level of cells in each well were measured with MSD Kit (MULTI-SPOT®96 4-Spot HB Prototype EGFR Triplex ANALYTES: pEGFR(Tyr1068), pEGFR(Tyr1173), Total EGFR (Cat # N45ZB-1). The assay is a electrochemiluminescent method (MESO SCALE DISCOVERY) for determining both phosphorylated and total EGFR of cells with an MSD SECTOR® Imager and then the ratio of p-EGFR/total EGFR can be generated by the machine. The percentage of inhibition was used the formula: % inhibition=100×[1−(ratio of sample well−ratio of Min ctrl well)/ (ratio of Max—Ratio of Min ctrl well)]. The $IC_{50}$ values were further calculated as the compounds concentration required for 50% inhibition in best-fit curves using Prism GraphPad 7.0 or Microsoft Xlfit software.

Example 30

Potency Assessment Against WT HER2

A compound's activity of selective inhibition for HER2 wild type amplification can be evaluated with BT474 cell line (ATCC® HTB-20™). The cell line expressed phosphorylated HER2 protein and its proliferation depended on the amplified gene, which could be used for in vitro PD and anti-proliferation assays.

The compounds' inhibition of target modulation were determined as follows: BT474 cells were sorted in 96 well plates (20000 cells/well) with the DMEM medium containing 10% FBS overnight and then treated with tested compounds at a series of concentrations (3 μM, 0.3 μM, 0.1 μM, 0.03 μM, 0.01 μM, 0.003 μM, 0.001 μM, 0.0001 μM. The plates were incubated for 4 h at 37° C. with 5% $CO_2$ and then the HER2 (Y1248) phosphorylation level of cells in each well were measured with MSD Kit (Phospho-ErbB2 (Tyr1248) Assay Whole Cell Lysate Kit: Cat # K151CLD-3). The assay is a electrochemiluminescent method (MESO SCALE DISCOVERY) for determining both phosphorylated and total HER2 of cells with an MSD SECTOR® Imager and then the ratio of p-HER2/total HER2 can be generated by the machine. The percentage of inhibition was got from formula: % inhibition=100×[1−(ratio of sample well−ratio of Min ctrl well)/(ratio of Max−Ratio of Min ctrl well)]. The $IC_{50}$ values were further calculated as the compounds concentration required for 50% inhibition in best-fit curves using Prism GraphPad 7.0 or Microsoft Xlfit software.

The anti-proliferation activity of compounds were determined as following procedure: The BT474 cells were sorted in 384 well plates with the DMEM medium containing 10% FBS and 1M OAA overnight and then dosed with tested compounds at a series of concentrations (30 μM, 10 μM, 3 μM, 0.3 μM, 0.1 μM, 0.03 μM, 0.01 μM, 0.001 μM) on next day. Meanwhile, another cells plate was prepared for measuring G0 value on next day. The dosed plates were incubate for 72h at 37° C. with 5% CO2 and the number of viable cells in each well of G0 or dosed plates were measured by MTS (CellTiter 96® AQueous One Solution Cell Proliferation Assay, Promega) endpoint. This assay is a colorimetric method for determining the number viable cells in the proliferation assay. Detection reagents (5 μl) was dispensed into per well, and the plates were incubated for 2 hrs at room temperature. Then, absorbance at 490 nm and 650 nm (reference wavelength) in each well was measured using the safile II. (Tecan). The percentage of proliferation was got from the formula: % Proliferation=100×(G3 value of sample well-Go value)/(G3 value of DMSO control-Go value). The GI50 values were further calculated as the compounds concentration required for 50% Proliferation in best-fit curves using Genedata Screener® software.

TABLE 2

Potency assessment results for exemplary compounds.

| Compound | HER2 WT Amplification BT474 $IC_{50}$ (nM) | EGFR WT NCI-H838 $IC_{50}$ (nM) | HER2 WT Amplification BT474 $GI_{50}$ (nM) |
|---|---|---|---|
| Compound 1 | 6.86 | >3000 | 24.21 ± 23.96 |
| Compound 2 | 6.17 | n/a | 19.02 ± 1.4 |
| Compound 3 | 26.03 | >3000 | 44.72 ± 4.2 |
| Compound 4 | 7.96 | >3000 | 4.33 ± 0.63 |
| Compound 5 | 6.83 | >3000 | 15.07 ± 8.19 |
| Compound 6 | 19.64 ± 8.76 | 3291.77 ± 1346.12 | 18.69 ± 9.16 |
| Compound 7 | 5.57 | >3000 | 8.36 ± 0.15 |
| Compound 8 | 6.92 | 1800.80 | 7.47 ± 2.99 |
| Compound 9 | 16.19 | 1033.21 | 27.34 ± 14.53 |
| Compound 10 | 7.86 | >3000 | 18.98 ± 2.46 |
| Compound 11 | 13.14 | >3000 | 24.59 ± 4.85 |
| Compound 12 | 7.56 | >3000 | 9.02 |
| Compound 13 | 21.75 | >3000 | 49.78 ± 6.87 |
| Compound 14 | 19.74 | 1388.33 | 26.84 ± 11.49 |
| Compound 15 | 2.55 | >10000 | — |
| Compound 16 | 10.58 ± 2.4 | 3060.46 ± 80.25 | 14.27 ± 13.64 |
| Compound 17 | 43.99 | >3000 | 126.04 ± 9.01 |
| Compound 18 | 12.58 | 514.80 | 8.58 ± 3.55 |
| Compound 19 | 9.56 ± 3.13 | >10000 | 11.52 |
| Compound 20 | 12.59 | >10000 | 41.05 ± 1.55 |
| Compound 21 | 61.3 ± 11.2 | — | 15.87 ± 6.57 |
| Compound 22 | 11.58 ± 10.44 | 2917.74 ± 2321.81 | 18.59 ± 6.51 |
| Compound 23 | 6.17 | >10000 | 11.7 |
| Compound 24 | 9.38 | >10000 | 50.77 |
| Compound 25 | 16.79 | >10000 | 47.24 |

TABLE 2-continued

Potency assessment results for exemplary compounds.

| Compound | HER2 WT Amplification BT474 IC$_{50}$ (nM) | EGFR WT NCI-H838 IC$_{50}$ (nM) | HER2 WT Amplification BT474 GI$_{50}$ (nM) |
|---|---|---|---|
| Compound 26 | 5.84 | >10000 | 14.06 |
| Compound 27 | 10.28 | 5132.19 | 22.06 |
| Compound 28 | 22.39 | 5222.21 | 35.82 |
| ONT380 | 2 | >3000 | 10.77 ± 4.13 |
| Neratinib | 1.96 | 1.73 | 0.71 ± 0.08 |
| Lapatinib | 23.13 | 3.07 | 12.1 ± 2.78 |

Example 31

Blood Brain Barrier Penetration Assay in Rats

In vitro blood, plasma and brain binding assay was carried out with equilibrium dialysis device. Diluted blood (1:1 with DPBS pH7.4), EDTA-anticoagulated plasma, and brain homogenate (1:3 with DPBS pH7.4) were spiked with 5 μM test compound (in triplicate) and dialyzed against equal volume of 150 μL 100 mM PBS buffer (pH7.4) at 37° C. for appropriate equilibration time in a slowly rotated plate. At the end of incubation, a 50 μL aliquot from the receiver side and a 5 μL from the donor chamber were taken. The 5 μL sample was further diluted with 45 μL of blank blood, plasma or brain homogenate. Paired samples were matrix-matched with either buffer or blank matrix, and mixed for 2 min, and then precipitated with 150 μL cold acetonitrile with 100 ng/mL tolbutamide as internal standard. After centrifuging at 4000 rpm for 20 min, supernatant was diluted with 0.1% formic acid aqueous solution and analyzed for LC/MS/MS (API 4000, Applied Biosystems, Foster City). Unbound fraction (fu) of test compound were calculated by the ratio of the buffer side response to the brain homogenate/plasma/blood side response, and unbound fraction (fu,bl, fu,pl and fu,br) of test compound in non-diluted blood and tissue were calculated from measured fu in homogenate and diluted blood with the following equation: fu,bl (fu,br)=(1/D)/[(1/fu−1)+1/D)]. D is dilution factor. (D equates 1 for plasma, 2 for blood, and 4 for brain)

A Short oral absorption (SOA) model is an in-vivo screening model to identify brain penetration of a compound. Six male Han Wistar rats purchased from Beijing Vital River were orally dosed with the compound. At predefined time point post-dose, cerebral spinal fluid (CSF) was collected from cisterna magna, and blood samples (>60 μL/time point/each site) were collected via cardiac puncture, into separate EDTA anti-coagulated tubes, and then immediately diluted with 3-fold volume of water for blood samples, or centrifuged at 4000 g for 10 min to obtain plasma. Brain tissue was harvested and homogenized in 3× volume of 100 mM phosphate buffered saline (pH7.4). All samples were stored at ~−70° C. prior to LC/MS/MS analysis.

Standards were prepared by spiking blank plasma, blood, brain homogenate and artificial CSF. Homogenized brain tissue along with blood/plasma samples were precipitated by adding 3-fold volume of cold acetonitrile containing internal standard, and 10 μL of CSF samples were precipitated with 100 μL of cold acetonitrile containing internal standard. After 2 min vortex and 5 min centrifugation at 14,000 rpm, supernatant was analyzed by LC/MS/MS (API 4000, Applied Biosystems, Foster City). Two sets of standard curves were run at the beginning and end of each batch from blood sample analysis. For brain and CSF samples, one standard curve was analyzed along with test samples.

Total brain levels, expressed as brain/blood ratio ($K_{p,brain}$) were measured by AUC(brain)/AUC(blood or plasma) in rodents after oral administration. Similarly, CSF levels represented by a ratio of CSF/blood exposure ($K_{p,CSF}$) were determined by AUC(CSF)/AUC(blood or plasma). Free fraction of test compound in biological matrix was determined by in vitro blood and brain binding assay.

$K_{p,uu brain}$ and $K_{p,uu CSF}$ was calculated by the following equation:

$$K_{p,uu\ brain} = AUC(\text{brain})/AUC(\text{blood or plasma}) \times (fu_{brain}/fu_{blood/plasma}) \text{ and}$$

$$K_{p,uu\ CSF} = AUC(CSF)/AUC(\text{blood or plasma}) \times (1/fu_{blood/plasma}).$$

TABLE 3

The data of $K_{p,uu\ brain}$ and $K_{p,uu\ CSF}$ for exemplary compounds

| Compound | $K_{p,uu\ brain}$ | $K_{p,uu\ CSF}$ |
|---|---|---|
| Compound 1 | 0.23 | 1.44 |
| Compound 6 | 0.18 | 0.56 |
| Compound 14 | 0.04 | 0.24 |
| Compound 16 | 0.03 | 0.11 |
| Compound 17 | 0.07 | 1.02 |
| Compound 19 | 0.10 | 0.40 |
| Compound 20 | 0.08 | 0.07 |
| Compound 24 | 0.23 | 1.44 |
| Compound 25 | 0.11 | 1.92 |
| Compound 27 | 0.10 | 0.52 |
| Compound 28 | 0.11 | 0.52 |
| Neratinib | AUC(brain) below detection limit | AUC(CSF) below detection limit |

Both $K_{p,uu\ brain}$ and $K_{p,uu\ CSF}$ should be the main parameters measured and optimized in CNS drug discovery (Di L et al., *Journal of Medicinal Chemistry* [2013], 56:2-12). $K_{p,uu\ brain}$, the relationship between concentrations of unbound drug in brain and in blood, predicts drug action on metastatic tumors in brain. Leptomeningeal metastasis (LM) results from metastatic spread of cancer to the leptomeninges, giving rise to central nervous system dysfunction. $K_{p,uu\ CSF}$ represents the distribution of drug in CSF as compared to that in blood, which drives drug response during leptomeningeal metastasis treatment. The assay data in Table 3 for the Compounds of this application as well as data obtained for Neratinib demonstrating the superior brain barrier and CSF barrier penetration properties of the compounds of the present invention, when compared to Neratinib.

While the present disclosure has been particularly shown and described with reference to specific embodiments (some of which are preferred embodiments), it should be understood by those skilled in the art that various changes in form and detail may be made therein without departing from the spirit and scope of the present disclosure as disclosed herein.

What is claimed is:
1. A compound of Formula (Ia):

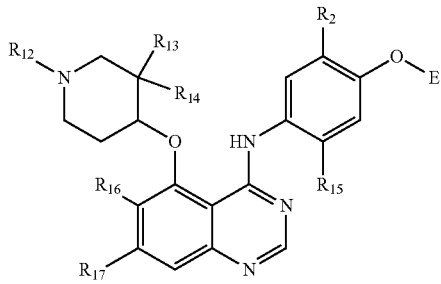

Formula (Ia)

or a pharmaceutically acceptable salt, thereof,
wherein,
$R_2$ is $C_{1-12}$ alkyl;
$R_{12}$ is hydrogen, $C_{1-12}$ alkyl or deuterium substituted $C_{1-12}$ alkyl;
each of $R_{13}$ and $R_{14}$ are independently halogen; $R_{15}$ is hydrogen;
$R_{16}$ and $R_{17}$ are each independently hydrogen or $C_{1-12}$ alkoxyl;
wherein E is

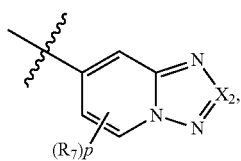

wherein
$X_2$ is CR8 and $R_8$ is hydrogen;
p is 0.

2. The compound of claim 1, selected from the group consisting of

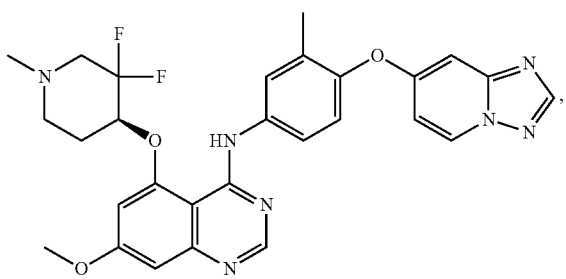

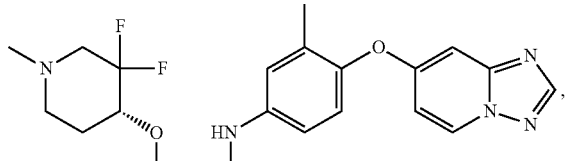

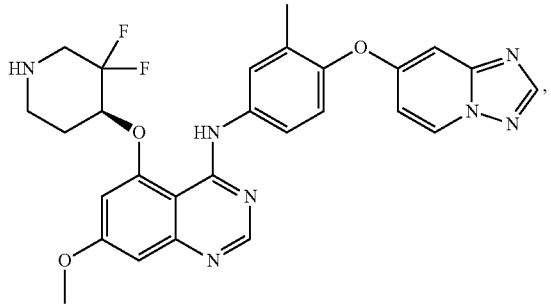

3. The compound of Formula (Ia), or a pharmaceutically acceptable salt thereof, according to claim 1, in crystalline form.

4. A pharmaceutical composition comprising one or more compounds, pharmaceutically acceptable salts thereof according to claim 1, and a pharmaceutically acceptable diluent, excipient or carrier.

5. A compound or a pharmaceutically acceptable salt thereof according to claim 1, in combination with a second therapeutic agent.

6. A compound or a pharmaceutically acceptable salt thereof according to claim 5, wherein the second therapeutic agent is an anti-tumor agent or a HER2 targeted antibody.

* * * * *